(12) United States Patent
Zimanyi

(10) Patent No.: US 10,783,700 B2
(45) Date of Patent: Sep. 22, 2020

(54) PROGRESSIVE LENS SIMULATOR WITH AN AXIAL POWER-DISTANCE SIMULATOR

(71) Applicant: eyeBrain Medical, Inc., Costa Mesa, CA (US)

(72) Inventor: Gergely T. Zimanyi, Berkeley, CA (US)

(73) Assignee: Neurolens, Inc., Costa Mesa, CA (US)

(*) Notice: Subject to any disclaimer, the term of this patent is extended or adjusted under 35 U.S.C. 154(b) by 72 days.

(21) Appl. No.: 15/984,397

(22) Filed: May 20, 2018

(65) Prior Publication Data
US 2019/0355168 A1 Nov. 21, 2019

(51) Int. Cl.
| | |
|---|---|
| A61B 3/11 | (2006.01) |
| G06T 15/10 | (2011.01) |
| G02B 7/04 | (2006.01) |
| G02B 3/14 | (2006.01) |
| G02B 26/00 | (2006.01) |
| H04N 13/383 | (2018.01) |
| G06N 3/08 | (2006.01) |
| G02B 7/02 | (2006.01) |
| G06F 30/20 | (2020.01) |

(52) U.S. Cl.
CPC ............ *G06T 15/10* (2013.01); *G02B 3/14* (2013.01); *G02B 7/021* (2013.01); *G02B 7/04* (2013.01); *G02B 26/004* (2013.01); *G06F 30/20* (2020.01); *G06N 3/08* (2013.01); *H04N 13/383* (2018.05); *G06T 2210/41* (2013.01); *G06T 2215/16* (2013.01)

(58) Field of Classification Search
CPC .... G06F 3/013; G06F 17/275; G06F 17/5009; A61B 3/113; A61B 5/163
USPC ................. 351/209, 210, 221, 246
See application file for complete search history.

(56) References Cited

U.S. PATENT DOCUMENTS

| | | |
|---|---|---|
| 3,583,790 A | 6/1971 | Baker |
| 6,329,989 B1 | 12/2001 | Qi et al. |
| 6,517,201 B2 | 2/2003 | Qi |
| 6,604,826 B2 | 8/2003 | Akiyama et al. |
| 7,039,563 B2 | 5/2006 | Qi |

(Continued)

FOREIGN PATENT DOCUMENTS

IN 00349MU2013 A 11/2014

*Primary Examiner* — Hung X Dang

(57) ABSTRACT

A Progressive Lens Simulator comprises an Eye Tracker, for tracking an eye axis direction to determine a gaze distance, an Off-Axis Progressive Lens Simulator, for generating an Off-Axis progressive lens simulation; and an Axial Power-Distance Simulator, for simulating a progressive lens power in the eye axis direction. The Progressive Lens Simulator can alternatively include an Integrated Progressive Lens Simulator, for creating a Comprehensive Progressive Lens Simulation. The Progressive Lens Simulator can be Head-mounted. A Guided Lens Design Exploration System for the Progressive Lens Simulator can include a Progressive Lens Simulator, a Feedback-Control Interface, and a Progressive Lens Design processor, to generate a modified progressive lens simulation for the patient after a guided modification of the progressive lens design. A Deep Learning Method for an Artificial Intelligence Engine can be used for a Progressive Lens Design Processor. Embodiments include a multi-station system of Progressive Lens Simulators and a Central Supervision Station.

17 Claims, 49 Drawing Sheets

(56) References Cited

U.S. PATENT DOCUMENTS

| | | |
|---|---|---|
| 8,583,406 B2 | 11/2013 | Shinohara et al. |
| 8,717,363 B2 | 5/2014 | Contractor et al. |
| 8,814,354 B2 | 8/2014 | Berthezene et al. |
| 8,944,599 B2 | 2/2015 | Ohta et al. |
| 9,239,472 B2 | 1/2016 | Mousset et al. |
| 9,364,142 B2 | 6/2016 | Hatanaka et al. |
| 9,629,539 B2 | 4/2017 | Qi |
| 9,772,513 B2 | 9/2017 | Qi |
| 9,967,555 B2 | 5/2018 | Qi et al. |
| 10,032,297 B2 | 7/2018 | Qi |
| 2008/0316427 A1 | 12/2008 | Fisher et al. |
| 2012/0019775 A1 | 1/2012 | Tyrin et al. |
| 2013/0222764 A1 | 8/2013 | Thompson et al. |
| 2017/0188813 A1 | 7/2017 | Arnold et al. |
| 2017/0364732 A1* | 12/2017 | Komogortsev .... G02B 27/0093 |
| 2018/0149883 A1 | 5/2018 | Asami et al. |

\* cited by examiner

FIG. 19A

Method 400 of Progressive Lens Simulation with a LDES 300

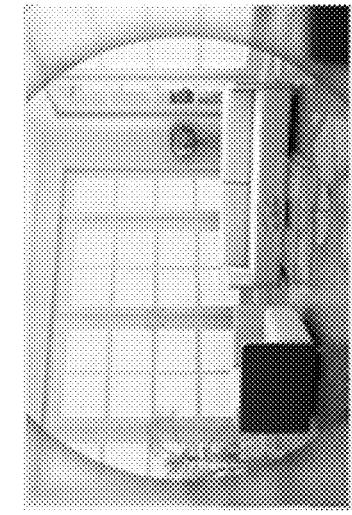
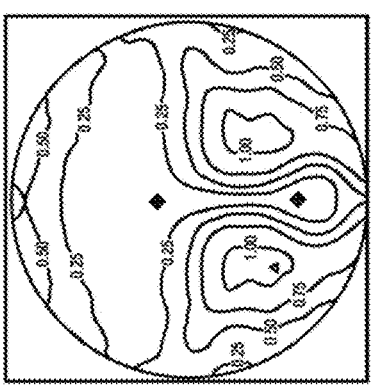
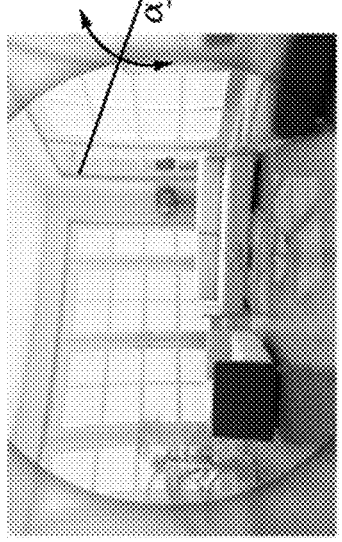

401 — (a) activating a progressive lens design 123 with Design Factors 420 by a Progressive Lens Design Processor 320

402 — (b) generating an image 21 by an Image Generator 121 of a Progressive Lens Simulator PLS 100

403 — (c) generating a Comprehensive PLS 30, simulated from the generated image 21 by the Progressive Lens Simulator PLS 100, utilizing the progressive lens design 123

404 — (d) acquiring a Visual Feedback 430, responsive to the generating of the Comprehensive PLS 30 with the progressive lens design 123

405 — (e) modifying the progressive lens design 123 by the Progressive Lens Design Processor 320 in relation to the Visual Feedback 430

406 — (f) re-generating the Comprehensive PLS 30 with the modified progressive lens design 123 by the Progressive Lens Simulator PLS 100

| Visual Feedback-to-Lens Design Transfer Engine FLE 325 → Visual Feedback 430 / Design Factor 420 | lower nasal quadrant blurry | lower temporal quadrant blurry | nasal progression region has too much swim | optical center too high/low | progression corridor too long/wide | visual inspection direction too jittery | rotate cylinder orientation angle |
|---|---|---|---|---|---|---|---|
| move optical center up/down | | | | | | | |
| increase/decrease progression corridor length | | | | | | | |
| increase/decrease progression corridor width | | | | | | | |
| increase/decrease progression pitch | | | | $VFDF_{ij}$ | | | |
| increase/decrease prism angle | | | | | | | |
| increase/decrease prism progression | | | | | | | |
| rotate cylinder orientation cw/ccw | | | | | | | |
| make contour lines smoother | | | | | | | |
| increase/decrease Zernike coefficient Z40/Z42 | | | | | | | |

Visual Feedback-to-Design Factor matrix VFDF 326

FIG. 22B

Lens Merit factors 460

(a) an improved visual acuity in one of a near and a far vision region (b) a reduced astigmatism in one of a near and a far vision region (c) a reduced swim in one of a near and a far vision region (d) a reduced blur in one of a near and a far vision region (e) a suitable progressive region (f) an alignment of a cylinder (g) a suitable prism (h) a suitable progressive prism

FIG. 24A

Lens Merit factor vector LM 460

$LM_1$: an improved visual acuity in one of a near and a far vision region $LM_2$: a reduced astigmatism in one of a near and a far vision region $LM_3$: a reduced swim in one of a near and a far vision region $LM_4$: a reduced blur in one of a near and a far vision region $LM_5$: a suitable progressive region $LM_6$: an alignment of a cylinder $LM_7$: a suitable prism $LM_8$: a suitable progressive prism

FIG. 24B

PROGRESSIVE LENS SIMULATOR WITH AN AXIAL POWER-DISTANCE SIMULATOR

FIELD OF INVENTION

This invention relates generally to methods and systems for simulating progressive lenses, more specifically to simulate progressive lenses with a guided lens design exploration system.

BACKGROUND

Prescriptions for eyeglasses, or spectacles, are generated today by devices and methods that were developed many decades ago, their foundations going back even farther in time. While these methods and technologies are mature, and served the patient population well, they did not benefit from the remarkable progress of optoelectronics and computational methods that revolutionized so many areas in telecommunications, consumer electronics, and interactive functionalities. Viewing optometry from the vantage point of modern opto-electronics and computer science, several areas of needs and opportunities can be identified. Some of the leading challenges and opportunities are listed and reviewed below.

(1) No trial before purchase: Patients who are asking for a progressive lens prescription are examined today only with single-power, non-progressive lenses, one for distance vision, and one for near vision. Therefore, the patients do not experience the prescribed progressive lenses in their totality before they purchase it. Since the patients do not "test-drive" the progressive lens prescriptions, they discover problems or inconveniences too late, only after the glasses have been provided to them.

(2) Only analog optometric devices are used: The single power lenses and other optical systems used by optometrists today have been developed long time ago. They are analog optical systems, and have not adapted and adopted the many advances of modern optoelectronic technology. This is to be contrasted by the very successful adaptation of optoelectronic technologies into other areas of ophthalmology, such as retinal imaging by Optical Coherence Tomography, aberrometric diagnostic devices, and optical diagnostic devices used in preparation for cataract surgery to determine the appropriate intraocular lenses.

(3) Only two distances tested: These analog lens systems test a patient's vision only at two distances, the near and the distance vision. In contrast, most patients have unique usage patterns, and often need the optimization of their spectacles for three or more distances depending on their individual habits.

(4) Eyes are only tested individually: Most of the diagnostic methods are applied for single eyes, blocking the other eye. Such approaches disregard the coordination between the eyes when they create the visual experiences, as well as the various effects of the vergence that are quite important for the full evaluation of the binocular visual acuity.

(5) Progressive lens prescriptions are under-defined: The design of progressive lenses is a complex process. Different companies have different proprietary optimization algorithms, with many parameters that use different search and optimization strategies. In contrast, the optometrists only determine 2-3 parameters about a patient's vision during an office visit. In a mathematical sense, providing only 2-3 parameters for the design of a progressive lens seriously under-defines the optimization algorithm of the lens design. When the design optimization algorithms have insufficient information, the algorithms can, and often do, stop at designs that are not truly optimal, and they are unable to identify the truly optimal design.

(6) Determining more parameters would increase treatment time per patient: Optometrists could run more tests to determine more parameters. However, doing so would extend the time spent with individual patients. This would have a negative effect on the economic model of the optometrists.

(7) Patients often need to return glasses for adjustments: Patients are unsatisfied with their progressive lenses in a statistically relevant fraction of the cases. Therefore, patients often return to the optometrist office asking for adjustments. It is not uncommon that a progressive lens has to be readjusted 3-4-5 times. The time and cost associated with these return visits seriously impacts the satisfaction of the patient, and undermines the economic model of the optometrist.

(8) Lens design verification groups are small: Lens design algorithms are typically optimized in interaction with a small test group, from less than a hundred to a couple hundred patients. Using only such small test groups for optimizing such a complex problem can lead to lens design algorithms that are not optimal. Subsequent complaints from the larger number of real patients yields feedback from a larger group, but this feedback is incomplete and unidirectional.

(9) Testing images do not reflect patient's actual visual needs: Eye testing uses standardized letters that are rarely reflective of a patient's actual needs. Testing just about never involves images that are relevant for the individual patient.

(10) Peripheral vision rarely tested: Optometrists rarely tests peripheral vision, whereas for some professions, peripheral vision might be a high value component of the overall visual acuity.

(11) Modern search algorithms are not yet utilized: Recent advances that greatly boost the efficiency of search algorithms over complex merit-landscapes, have not yet been adapted to the design of progressive lenses.

(12) Artificial Intelligence is not used: Recent advances in implementing Artificial Intelligence for system improvements also have not found their way yet into optometry.

At least the above dozen problems demonstrate that optometry could greatly benefit in a large number of ways from implementing modern optoelectronic technologies, in a patient-centric, customized manner, that also uses progress in modern computer science.

SUMMARY

To address the above described medical needs, some embodiments of the invention include a Progressive Lens Simulator, comprising: an Eye Tracker, for tracking an eye axis direction to determine a gaze distance, an Off-Axis Progressive Lens Simulator, for generating an Off-Axis progressive lens simulation (Off-Axis PLS); and an Axial Power-Distance Simulator, for simulating a progressive lens power in the eye axis direction, thereby creating a Comprehensive progressive lens simulation from the Off-Axis PLS.

Embodiments also include a method of operating a Progressive Lens Simulator, the method comprising: tracking an eye axis direction by an Eye Tracker to determine a gaze distance; generating an off-axis progressive lens simulation (Off-Axis PLS) by an Off-Axis Progressive Lens Simulator; and creating a Comprehensive progressive lens simulation from the Off-Axis PLS by simulating a progressive lens power in the eye axis direction by an Axial Power-Distance Simulator.

Embodiments further include a Progressive Lens Simulator, comprising: an Eye Tracker, for tracking an eye axis direction to determine a gaze distance; an Integrated Progressive Lens Simulator, for creating a Comprehensive Progressive Lens Simulation (PLS) by simulating a progressive lens power in the eye axis direction, in combination with generating an Off-Axis progressive lens simulation (Off-Axis PLS).

Embodiments also include a Head-mounted Progressive Lens Simulator, comprising: an Eye Tracker, for tracking an eye axis direction to determine a gaze distance; an Integrated Progressive Lens Simulator, for creating a Comprehensive Progressive Lens Simulation (PLS) by simulating a progressive lens power in the eye axis direction, in combination with generating an Off-Axis progressive lens simulation (Off-Axis PLS); wherein the Eye Tracker and the Integrated Progressive Lens Simulator are implemented in a head-mounted display.

Embodiments further include a Guided Lens Design Exploration System for Progressive Lens Simulator, comprising: a Progressive Lens Simulator, for generating a progressive lens simulation for a patient with a progressive lens design; a Feedback-Control Interface, for inputting at least one of control and feedback by the patient, in response to the progressive lens simulation; and a Progressive Lens Design processor, coupled to the Feedback-Control Interface, for receiving the at least one of control and feedback from the patient, and modifying the progressive lens design in response to the receiving, wherein the Progressive Lens Simulator is configured to generate a modified progressive lens simulation for the patient with the modified progressive lens design.

Embodiments also include a method of Progressive Lens Simulation, comprising: (a) activating a lens design with a Progressive Lens Design Processor; (b) generating an image by an Image Generator of a Progressive Lens Simulator; (c) generating a Comprehensive PLS, simulated from the generated image by the Progressive Lens Simulator, utilizing the lens design; (d) acquiring a visual feedback via a Feedback-Control Interface, responsive to the generating of the Comprehensive PLS with the lens design; (e) modifying the lens design by the Progressive Lens Design Processor in relation to the visual feedback; and (f) re-generating the Comprehensive PLS with the modified lens design by the Progressive Lens Simulator.

Embodiments further include a Deep Learning Method for an Artificial Intelligence Engine for a Progressive Lens Design Processor, comprising: activating a Visual Feedback-Design Factor Neural Network for a Progressive Lens Design Processor; receiving as input a visual feedback vector into the Visual Feedback-Design Factor Neural Network; outputting a design factor vector with the Visual Feedback-Design Factor Neural Network in response to the inputting; wherein coupling matrices of the Visual Feedback-Design Factor Neural Network of the Progressive Lens Design Processor were trained by performing a deep learning cycle.

Embodiments also include a Supervised Multi-station system of Progressive Lens Simulators, comprising: a set of Progressive Lens Simulators, individually including an Eye Tracker, for tracking an eye axis direction to determine a gaze distance; an Off-Axis Progressive Lens Simulator, for generating an Off-Axis progressive lens simulation (Off-Axis PLS); and an Axial Power-Distance Simulator, for simulating a progressive lens power in the eye axis direction, thereby creating a Comprehensive progressive lens simulation from the Off-Axis PLS; and a Central Supervision Station, in communication with the Progressive Lens Simulators, for providing supervision for an operation of the individual Progressive Lens Simulators.

BRIEF DESCRIPTION OF THE DRAWINGS

FIGS. 19A-B illustrate methods of Progressive Lens Simulation in some detail.

FIGS. 22A-B illustrate a Visual Feedback-to-Design Factor matrix of a Visual Feedback-to-Lens Design Transfer Engine.

FIGS. 24A-B illustrate Lens Merit factors.

DETAILED DESCRIPTION

Figure 1:
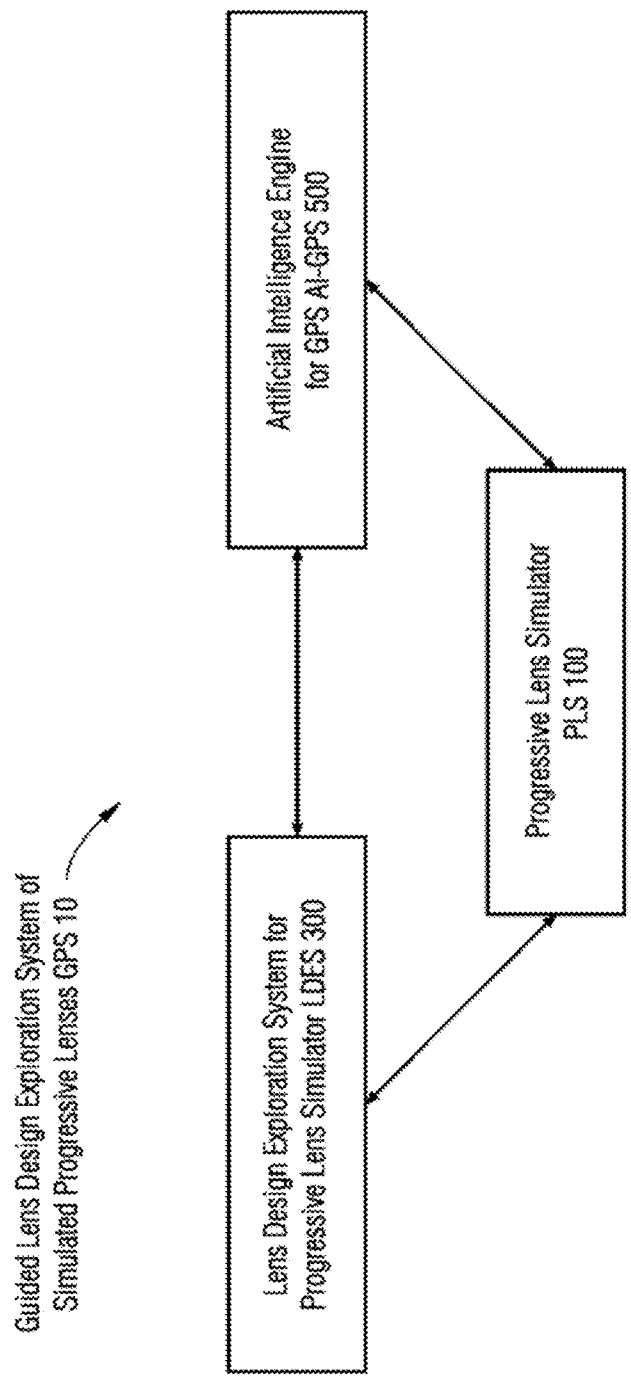
FIG. 1 illustrates a Guided Lens Design Exploration System of Simulated Progressive Lenses (GPS).

The systems and methods described in the present patent document address the above articulated medical needs at least in the following aspects. These aspects are organized in a contrasting format to the previously described challenges of the state of the art.

(1) No trial before purchase: In embodiments, the visual experience of progressive lenses is simulated by a Progressive Lens Simulator. This system empowers the patient to actively and interactively explore and experience progressive lenses with different designs in real time. The patient can explore as many simulated progressive lens designs as she or he wishes before settling on a particular design. In short, the patient can explore, "test drive", and "try on" the progressive lens before purchasing it.

(2) Only analog optometric devices are used: Embodiments use modern digital optoelectronic technology instead of analog optical technologies.

(3) Only two distances tested: The patient can explore the performance of the various progressive lens designs at as many distances as he or she wishes by virtue of modern optoelectronic designs.

(4) Eyes are tested individually: The patient can explore the visual experience with the simulated progressive lenses with both eyes simultaneously. This approach allows the lens design selection process to include and optimize for the patient's experience of the effects of vergence.

(5) Progressive lens prescriptions are under-defined: The patient can explore the many possible progressive lens designs exhaustively. The search can concentrate on many particular aspects of the performance of the lens. Monitoring the search process in detail provides an extensive amount of data about the patient's vision for the advanced lens design software. The acquisition of this larger amount of data turns the lens design process from under-defined to appropriately defined in a mathematical sense. The exploration process can be continued until the lens design software concludes that it has sufficient data to zoom in on the most optimal lens design.

(6) Determining more parameters would increase treatment time per patient: The selection process of the best progressive lens design with the here-described embodiments may take longer, or even substantially longer than the duration of a typical office visit today. This may be perceived as an economic "excessively high costs" argument against the described system. However, much of the search is guided by smart software and thus does not require the active presence of the optometrist. Rather, the optometrists play a supervisory role and thus can supervise even a greater number of patients per day with these Progressive Lens Simulators than with the traditional methods.

(7) Patients often need to return glasses for adjustments: Since the patients explore all relevant and possible progressive lens designs in real time, the here-described Progressive Lens Simulator system minimizes the patient complaints and returns. This dramatically improves patient satisfaction and greatly boosts the economic model of the optometrists.

(8) Lens design verification groups are small: The search data are collected from all participating optometrist offices. Therefore, the progressive lens design software will have access to the recorded search patterns, patient behaviors, and eventual patient choices from the test group of millions of patients. Access to such a huge and rapidly growing database will be used to rapidly and efficiently improve the progressive lens design algorithms.

(9) Testing images do not reflect patient's actual visual needs: The Progressive Lens Simulators offer to patients the testing of their vision on any images they choose. A promising implementation is presenting use-relevant images that are relevant for and simulate the patient's actual activities.

(10) Peripheral vision rarely tested: The digital image-projection system can present both central and peripheral images for a full characterization of a patient's vision.

(11) Modern search algorithms are not yet utilized: The Guidance System for Patient Exploration in some embodiments uses modern search techniques that were developed to explore complex, multiply interdependent and constrained merit-landscapes.

(12) Artificial Intelligence is not used: Artificial Intelligence Engines are used for constantly improving and upgrading the system's software block-by-block.

The here-described systems can only yield positive outcomes, because they can be first used to determine the traditional progressive lens prescription with the traditional procedure. Subsequently, the Progressive Lens Simulator can perform various advanced searches by here-described embodiments, and guide the patient to the advanced progressive lens prescription best suited for him/her. Finally, the Progressive Lens Simulator can simulate the traditional progressive lens experience, followed by the advanced progressive lens experience, and alternate back-and-forth so that the patient can compare the two progressive lens experiences to make her/his final choice. Since the patient can always return to and select the traditional progressive lens design, the overall outcome of the process cannot be worse than the traditional process, only better.

This patent document describes many embodiments, techniques and methods. It also describes more than a dozen advantages over existing traditional systems. Thus, the described advantages are not limiting for all embodiments. Indeed, embodiments which possess only one or a few of the advantages are already novel over existing systems. Also, several other, not-yet-listed advantages exist that make the system novel. Moreover, several of the described aspects can be combined in various embodiments for additional synergetic advantages.

Figure 2:
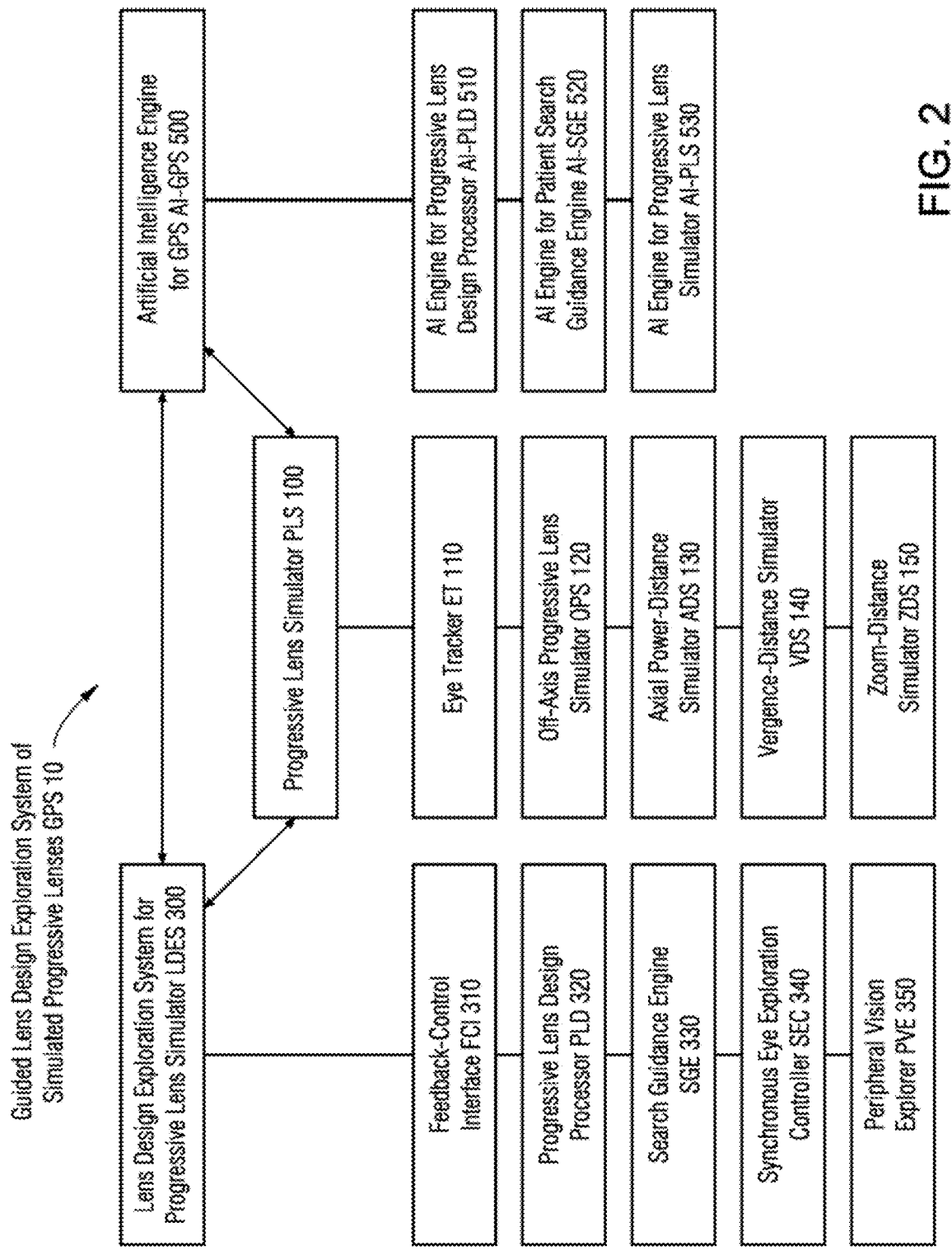
FIG. 2 illustrates the Guided Lens Design Exploration System of Simulated Progressive Lenses (GPS) in some detail.

FIG. 1 and FIG. 2 illustrate the Guided Lens Design Exploration System of Simulated Progressive Lenses (GPS) 10 on a high, system level. Embodiments of the GPS 10 possess one or more of the above described features and advantages, as follows.

(1) Patients can explore and "try on" many different progressive lens designs before selecting one for purchase.

(2) Embodiments use modern digital optoelectronic technology.

(3) Patients can test their vision at as many distances as they wish.

(4) The two eyes of the patients can be tested synchronously, thus factoring their vergence into the overall visual experience.

(5) The eventually selected progressive lens designs and prescriptions are well-defined because a sufficient number of parameters are determined.

(6) Since patients are exploring the progressive lens designs on their own, guided by a smart software, the demand on the time of the optometrists actually decreases relative to present systems, as the optometrists are expected only to supervise the patients' exploration.

(7) Since patients select their own design, glasses are returned for adjustments much less frequently.

(8) Lens design verification groups are large and ever expanding.

(9) Testing images reflect patient's actual visual needs.

(10) Patients' peripheral vision is tested as extensively as the patients desire.

(11) Cutting edge search algorithms are utilized to guide the patient exploration.

(12) Artificial Intelligence is used to continuously upgrade and improve both the lens design and the patient guidance systems.

These system level concepts of the GPS 10 are described in general in FIGS. 1-2, and subsequently in detail in FIGS. 3-36. In particular, FIGS. 3-15 describe many embodiments of Progressive Lens Simulators that generate life-like Comprehensive Progressive Lens Simulations of as many progressive lens designs as the patient wishes to explore. FIGS. 16-29 describe guidance systems and methods that guide the patients in their exploration of the progressive lens designs. FIGS. 30-35 describe Artificial Intelligence systems and methods to train and improve the Progressive Lens Simulators. Finally, FIG. 36 describes a supervised Multi-station GPS system.

FIG. 1 illustrates that the Guided Lens Design Exploration System of Simulated Progressive Lenses (GPS) 10 can include a Progressive Lens Simulator (PLS) 100, for simulating various progressive lens designs; a Lens Design Exploration System for Progressive Lens Simulator (LDES) 300, for intelligently guiding the exploration of the many possible progressive lens designs by the patient; and an Artificial Intelligence Engine for GPS (AI-GPS) 500, for monitoring the lens design exploration process by the patients, in order to discover and extract possible improvements of the GPS 10 system, followed by actually implementing of the discovered improvements. These three major building blocks of the fully integrated GPS 10 system can be all coupled to each other for efficient communication. [In the rest of the specification, sometimes only the abbreviating acronyms will be used for reference and brevity.]

FIG. 2 illustrates elements of these three main building blocks PLS 100, LDES 300 and AI-GPS 500 in some detail. The Progressive Lens Simulator PLS 100 can include an Eye Tracker (ET) 110, for tracking the direction of an axis, or gaze, of the patient's eyes, as well as the eye movements. The Eye Tracker 110 can determine the distance of the target the patient is looking at from the vergence of the axes of the two eyes. Several Eye Tracker designs are known in the art and can be adapted and implemented in this PLS 100. The PLS 100 can further include an Off-Axis Progressive Lens Simulator (OPS) 120, for simulating the off-axis visual experience of a selected Progressive Lens design. This experience is quite complex, as the effective optical power of progressive lenses changes with the angle relative to the optical axis.

The PLS 100 can further include an Axial Power-Distance Simulator (ADS) 130, that simulates a combination of the distance of the viewed image and the axial power of the progressive lens. Since the PLS 100 simulates progressive lenses, the optical power varies substantially over the lens surface. In multistage embodiments, the PLS 100 simulates this with a combination of simulating the most important axial power with the ADS 130, and the off-axis power with the separate OPS 120. In integrated embodiments, the PLS 100 simulates the spatially varying optical power with an Integrated Progressive Lens Simulator IPLS 200.

The PLS 100 can further include a Vergence-Distance Simulator (VDS) 140 that simulates the viewing distance in a different manner. The VDS 140 can present the images for the two eyes not dead ahead, but moved closer to each other, in order to create the visual experience of the target image being at a closer viewing distance. Finally, a Zoom-Distance Simulator (ZDS) 150 can simulate a change of the viewing distance (changed by the PLS 100 from a first distance to a second distance) by zooming the image in or out. Doing so can further increase the sense of reality of the visual experiences generated by the PLS 100 for the patients.

The GPS 10 can include the Guided Lens Design Exploration System for Progressive Lens Simulator (LDES) 300, to guide the exploration of the large number of possible progressive lens designs by the patient with an efficient and informed strategy. The LDES 300 can include a Feedback-Control Interface (FCI) 310. This FCI 310 can be used by the patient to enter feedback and control signals for the PLS 100, in order to express preferences and provide feedback on the simulated progressive lens designs 123. In some embodiments, the LDES 300 can include a Progressive Lens Design Processor (PLD) 320. The PLD 320 can create the specific progressive lens design based on measurements of the patient's eyes; based on the patient's input, feedback, and control signals, and on lens design algorithms. The created specific progressive lens designs can be communicated by the PLD 320 to the PLS 100 to create the corresponding progressive lens visual experience for the patient.

The LDES 300 can further include a Search Guidance Engine (SGE) 330. The patient often, or even typically may not know how to change the design of the progressive lens to improve its optical performance. The patient typically only senses that the last change of the design made the visual experience better or worse. Or, the patient can articulate what improvements she/he is looking for. But since the progressive lens design can be modified in many different ways to bring about such changes, a guidance system to affect the desired change in an informed and strategic manned can be useful and in fact necessary. Providing such guidance is one of the functions of the SGE 330. The SGE 330 can receive a desired improvement or preference from a patient, and then suggest in return to the patient how to translate the requested improvement into a change of the lens design.

Some embodiments of the LDES 300 can further include a Synchronous Eye Exploration Controller (SEC) 340, that oversees and controls the visual experience of the two eyes synchronously, and plays an important role in integrating desired design improvements from the two eyes. Finally, the LDES 300 can also include a Peripheral Vision Explorer (PVE) 350, that evaluates the patient's vision in the peripheral zones, and feeds back this information into the simulation of the progressive lenses by the PLS 100.

Finally, the Artificial Intelligence Engine for GPS (AI-GPS) 500 can be included into some embodiments of the GPS 10, for monitoring the performance of the components of the PLS 100 and the LDES 300, and for developing suggested adjustments to improve the performance of the managed components of the GPS system 10. In some detail, the GPS 10 can include an Artificial Intelligence (AI) Engine for the Progressive Lens Design Processor (AI-PLD) 510, to monitor and improve the performance of the PLD 320. Other embodiments can include an AI engine for the Search Guidance Engine (AI-SGE) 520. Finally, some embodiments of the GPS 10 can include an AI Engine for the Progressive Lens Simulator (AI-PLS) 530. Each of the three AI engines 510/520/530 can be configured to monitor the functioning of the corresponding system blocks PLD 320, SGE 330, and PLS 100, and then perform AI-based training cycles to improve the performance of these blocks. In some embodiments, these AI engines are implemented by neural networks.

The above, system-level description of the GPS 10 is now expanded with the detailed description of a number of specific embodiments in more detail. For clarity, the presentation of these embodiments is organized into titled sections.

1. Progressive Lens Simulator with an Axial Power-Distance Simulator

Figure 3:
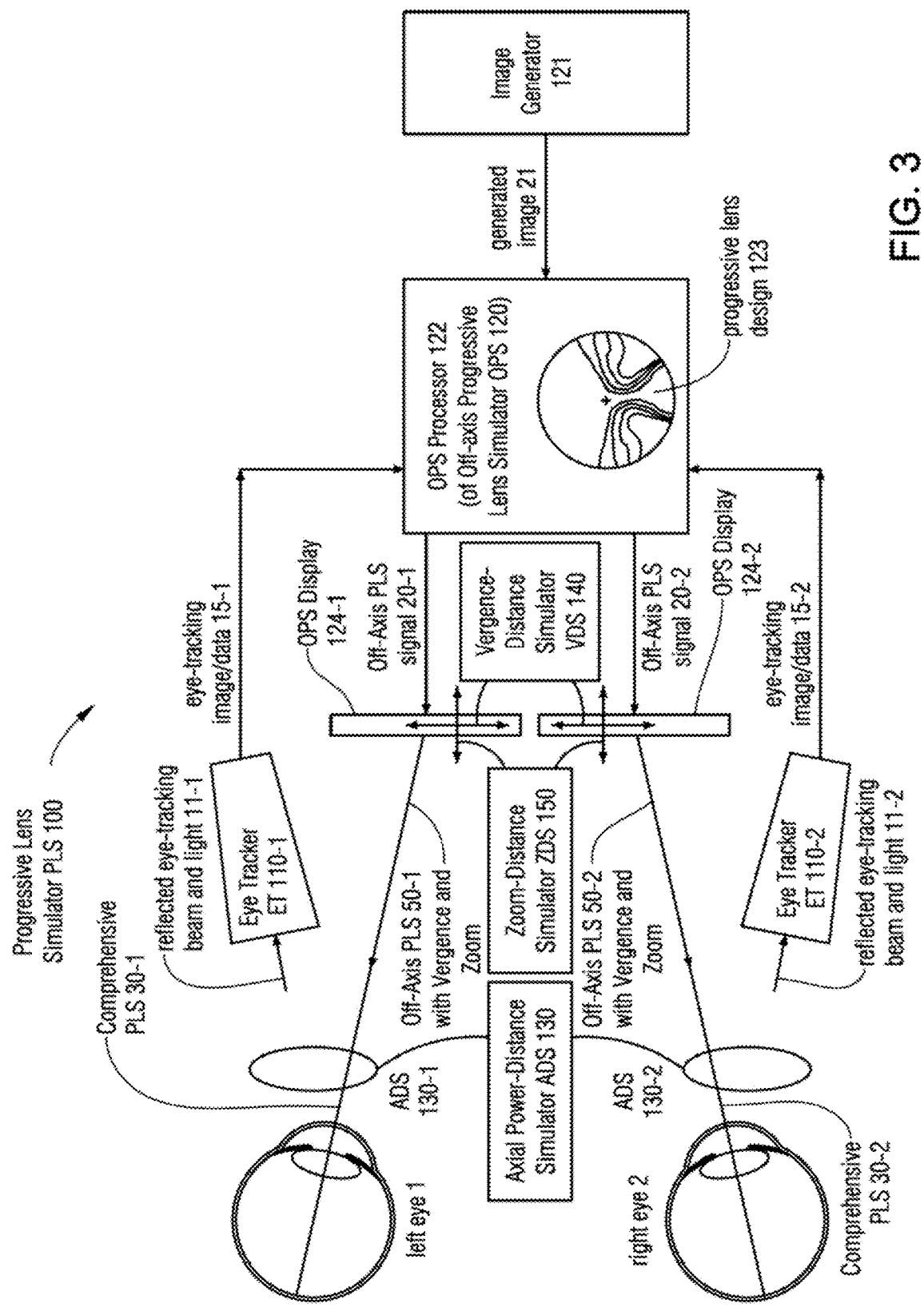
FIG. 3 illustrates a Multistage embodiment of a Progressive Lens Simulator.
Figure 4:
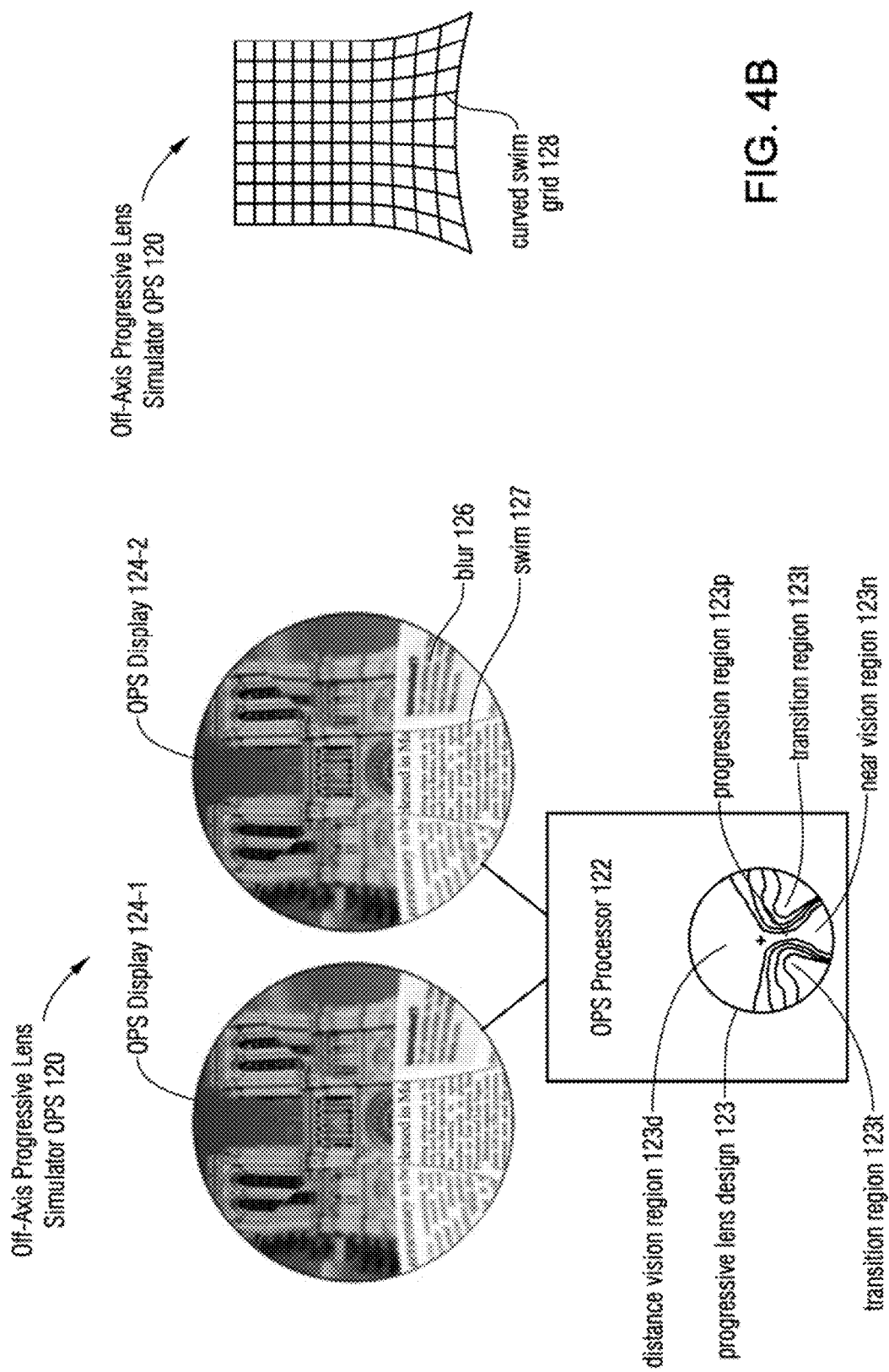
FIGS. 4A-B illustrate an Off-Axis Progressive Lens Simulator OPS.

FIG. 3 illustrates a Multistage embodiment of a Progressive Lens Simulator PLS 100, comprising: an Eye Tracker (ET) 110, for tracking an eye axis direction to determine a gaze distance, an Off-Axis Progressive Lens Simulator (OPS) 120, for generating an Off-Axis progressive lens simulation (Off-Axis PLS) 50 according to a progressive lens design 123; and an Axial Power-Distance Simulator (ADS) 130, for simulating a progressive lens power in the eye axis direction, thereby creating a Comprehensive progressive lens simulation 30 from the Off-Axis PLS 50. The eye axis direction is sometimes referred to as a visual axis.

In some embodiments, the Off-Axis Progressive Lens Simulator OPS 120 can include an Image Generator 121, for generating an image 21; an Off-Axis Progressive Lens Simulator Processor, or OPS processor, 122, for transforming the generated image 21 into Off-Axis PLS signals 20-1 and 20-2 according to according to the progressive lens design 123; and Off-Axis Progressive Lens Simulator Displays 124-1/124-2, for displaying the Off-Axis Progressive Lens Simulation (Off-Axis PLS) 50 according to the Off-Axis PLS signal 20. Here and in the following, many items X are included in the GPS 10 pairwise, one for each eye. They will be typically labeled as items X-1 and X-2. Sometimes, for brevity, the collection of items X-1 and X-2 will be simply referred to as X.

In some PLS 100, the Off-Axis Progressive Lens Simulator Display 124 includes a pair of Off-Axis Progressive Lens Simulator Screens 124-1 and 124-2, each displaying an Off-Axis PLS 50-1 and 50-2, the two PLS together providing a stereoscopic Off-Axis PLS 50 for a first/left eye 1 and a second/right eye 2.

In some PLS 100, the Off-Axis Progressive Lens Simulator Display 124 includes a single stereoscopic alternating Off-Axis Progressive Lens Simulator Screen 124, controlled by an image-alternator, for alternating the displaying the Off-Axis PLS 50-1 for the first eye 1, and subsequently PLS 50-2 for the second eye 2, with suitable stereoscopic adjustments. This rapidly alternating display on left eye/right eye images, with synchronized image-alternation, i.e. blocking the image for the non-targeted eye, allows the use of a single screen to generate stereoscopic images and viewing experience. This image-alternating technology has mechanical embodiments involving shuttering or rotating wheels, opto-electronic embodiments involving rapid polarization changes, and liquid crystal embodiments to block the images. Any one of these embodiments can be utilized in the stereoscopic alternating Off-Axis Progressive Lens Simulator Screen 124.

FIG. 4A illustrates that the progressive lens design 123 includes characteristic regions of a typical progressive lens. These include: a distance vision region 123$d$ in the upper portion of the progressive lens with a distance vision optical power OPd, a near vision region 123$n$ in the lower portion of the progressive lens, typically nasally shifted, having a stronger, near vision optical power OPn, and a progression region 123$p$, sometimes also called a channel, where the progressive optical power OPp progressively and smoothly interpolates between OPd and OPn. The progressive lens design 123 also includes a transition region 123$t$, typically on both sides of the channel/progression region 123$p$, where the front and back surfaces of the lens are shaped to minimize optical distortions arising from the optical power progressing in the channel 123$p$.

FIG. 4A illustrates that in the Progressive Lens Simulator PLS 100, the Off-Axis Progressive Lens Simulator Processor 122 can be configured (1) to receive the generated image 21 from the Image Generator 121; and (2) to transform the generated image 21 into the Off-Axis PLS signal 20 by introducing a locally varying blur 126, representative of the progressive lens design 123. This blur 126 is caused by the optical power of the progressive lens design locally varying in the transition region 123$t$ and in the channel, or progressive region 123$p$, causing the light rays from an object point not getting focused into a single, well-defined image point.

Analogously, in some embodiments of the PLS 100, the OPS Processor 122 can be configured (1) to receive the generated image 21 from the Image Generator 121; and (2) to transform the generated image 21 into the Off-Axis PLS signal 20 by introducing a locally varying curvature, or swim 127, representative of the progressive lens design 123.

FIG. 4B illustrates the swim 127 with a square grid as the imaged object. A typical progressive lens design 123 bends and curves the originally rectilinear lines of the square grid into a curved swim grid 128. These two effects are demonstrated in FIG. 4A: the transition regions of a regular image develop the blur 126 by the typical progressive lens design 123, and the straight lines get bent by the swim 127.

The OPS Processor 122 can perform a detailed ray tracing computation of light emanating from the generated image 21 through the progressive lens design 123 to quantitatively produce this blur 126 and swim 127. In alternate embodiments, wavefront propagation methods can be used by the OPS Processor 122. Generating the correct blur 126 and swim 127 are key functions of the OPS Processor 122 to generate the life-like Off-Axis Progressive Lens Simulation (PLS) 50 at least because of the followings. When a patient evaluates the visual experience of the particular progressive lens design 123, the primary positive experience is the customized increase of the optical power from OPd in the distance region to OPn in the near region, while the primary negative experience is "the price of the positives", the concomitant blur 126 and swim 127, induced by the power progression. The GPS 10 simulates different progressive lens designs 123 for a patient. The search for the optimal progressive lens design 123 is performed by the patient evaluating the balance of the positives against the negatives of the Comprehensive Progressive Lens Simulations 30 of the individual simulated designs 123, eventually identifying his/her most preferred design 123. The OPS Processor 122 crucially helps this search process by the most life-like simulation of the blur 126 and swim 127 of the designs 123. In some PLS 100, at least two of the Image Generator 121, the Off-Axis Progressive Lens Simulator Processor 122, and the Off-Axis Progressive Lens Simulator Display 124 can be integrated.

Figure 5:
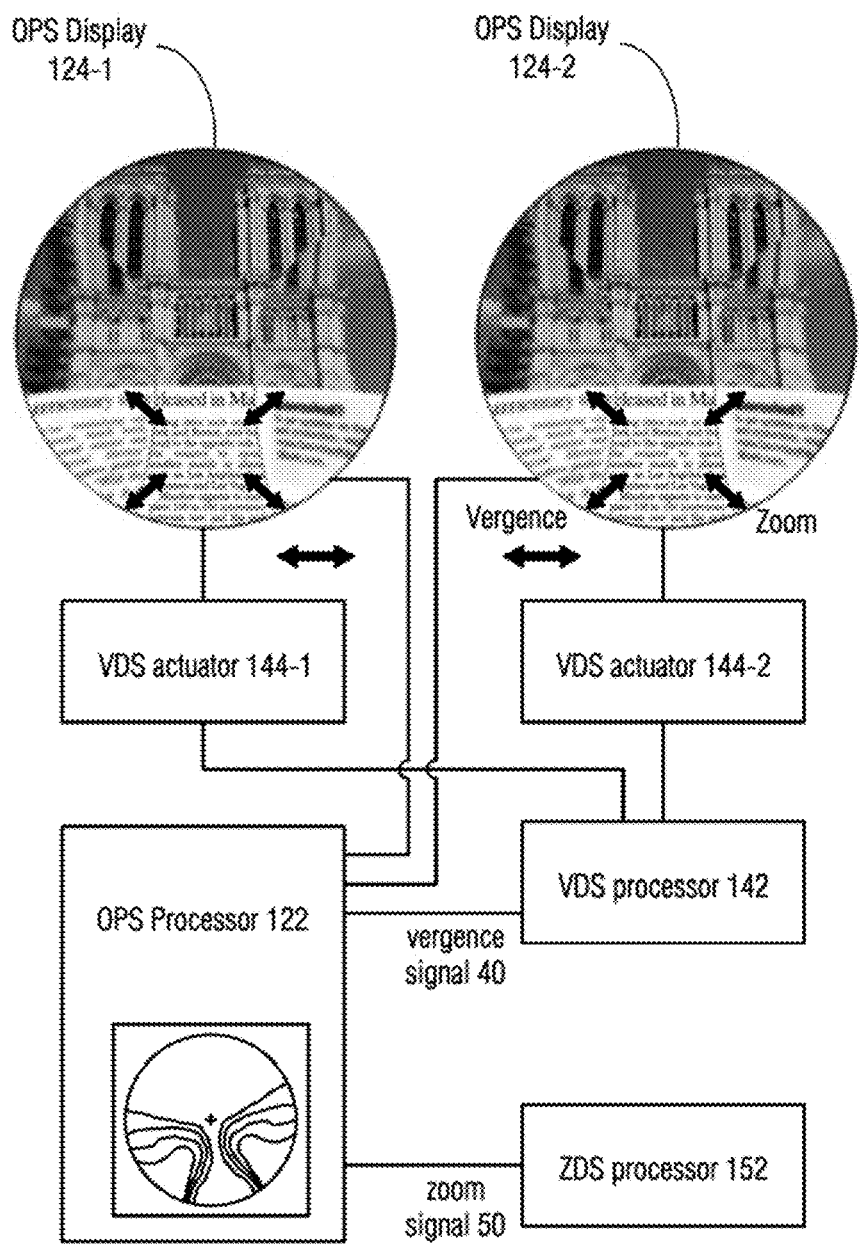
FIG. 5 illustrates a Progressive Lens Simulator with a Vergence-Distance Simulator VDS and a Zoom-Distance Simulator ZDS.

FIG. 3 and FIG. 5 further illustrate that the PLS 100 can include a Vergence-Distance Simulator VDS 140, for simulating a vergence for the displayed Off-Axis PLS 50 at the gaze distance, as determined by either the Eye Tracker 110, or intended by an operator. The utility of the VDS 140 was outlined earlier. The life-like visual experience of the Comprehensive PLS 30 can be further enhanced by moving the Off-Axis Progressive Lens Simulations PLS 50-1 and 50-2, and thereby the Comprehensive PLS 30-1 and 30-2 closer to each other when the eyes focus on a closer gaze distance. This can happen when the patient decides to lower and inwardly rotate her/his visual axis, intending to look through the near vision region 123*n* of the simulated progressive lens design 123. Another situation is when an operator, or a computer controller of GPS 10, decides to present a Comprehensive PLS 30 that corresponds to a closer gaze distance, to test the near vision of a patient. Simulating the vergence corresponding to a gaze distance correctly enhances the life-like visual experience to a remarkable degree.

The Vergence-Distance Simulator VDS 140 can be configured to simulate the vergence for the displayed Off-Axis PLS 50 at the gaze distance by (1) moving a screen of the Off-Axis Progressive Lens Simulator Display 124 dominantly laterally, or by (2) shifting the displayed Off-Axis PLS 50 on the Off-Axis Progressive Lens Simulator Display 124 dominantly laterally. In the latter embodiment, the Off-Axis PLS 50 is typically displayed only on a portion of the OPS display 124, thus leaving room to electronically moving the image of the Off-Axis PLS 50 laterally. Some PLS 100 includes the combination of (1) and (2). Other solutions can be used as well, such as rotating mirrors in the optical path of the Off-Axis PLS 50.

FIG. 5 illustrates that in some embodiments of the PLS 100, the VDS 140 can include a VDS processor 142, optionally coupled to the OPS Processor 122 to receive a vergence signal 40 and to control the Vergence Simulation. The VDS processor 142 can be coupled to vergence VDS actuators 144-1 and 144-2. In some embodiments, these VDS actuators 144-1 and 144-2 can mechanically move the OPS displays 124-1 and 124-2 laterally.

FIG. 3 and FIG. 5 also illustrate that some PLS 100 can include a Zoom-Distance Simulator ZDS 150, to further increase the life-like visual experience of the Comprehensive PLS 30 by zooming the Comprehensive PLS 30 in accord with the changes of the gaze distance. This ZDS 150 can be activated when a patient decides to move his/her gaze relative to the progressive lens design 123. For example, the patient moves his/her gaze from the distance vision region 123*d* to the near visions region 123*n* of the progressive lens design, in order to look at a near object. The ZDS 150 can increase the life-like experience of this move by zooming in on the near object. As shown in FIG. 5, the PLS 100 can include a ZDS processor 152, coupled to the OPS Processor 122 to receive or send a zoom signal 50. In some cases, the ZDS processor 152 can be notified by the Eye Tracker 110 that the patient turned his/her gaze direction lower and inward, as part of a process of switching to looking at a nearby portion of the overall generated image 21, for example to look at a foreground object. In response, the ZDS processor 152 can notify the OPS Processor 122 via the zoom signal 50 to zoom in on the nearby portion of the generated image 21, for example, on the foreground object.

With modern opto-electronic techniques, the above described simulators can be integrated to various degrees. In some PLS 100, at least one of the Off-Axis Progressive Lens Simulator Processor 122, the Off-Axis Progressive Lens Simulator Display 124, and the Axial Power-Distance Simulator ADS 130 can include at least one of the Vergence-Distance Simulator 140 and the Zoom-Distance Simulator 150. In some cases, only the VDS processor 142 or the ZDS processor 152 can be included.

Next, the description turns to various embodiments of the Axial Power-Distance Simulator ADS 130. In general, the ADS 130 can be an adjustable optical system that has an adjustable optical refractive power. This adjustable optical refractive power of the ADS 130 can be adjustable to be consistent with the gaze distance, determined by the Eye Tracker 110. In other embodiments, the adjustable optical power of the ADS 130 can be adjusted to an intended gaze distance, such as when the patient, or an operator of the GPS 10 decides to explore and test vision at a different distance.

In some embodiments, the ADS 130 uses optical elements such as lenses and mirrors whose optical power is adjustable, but whose position is fixed. In other embodiments, the ADS 130 can use optical elements whose position is also adjustable to simulate a vergence corresponding to the eye axis direction, or visual axis. A simple embodiment of the ADS can include a pair of adjustable lenses or mirrors that are laterally translatable, or rotatable, to increase the life-likeness of the simulation of the vergence.

Figure 6A:
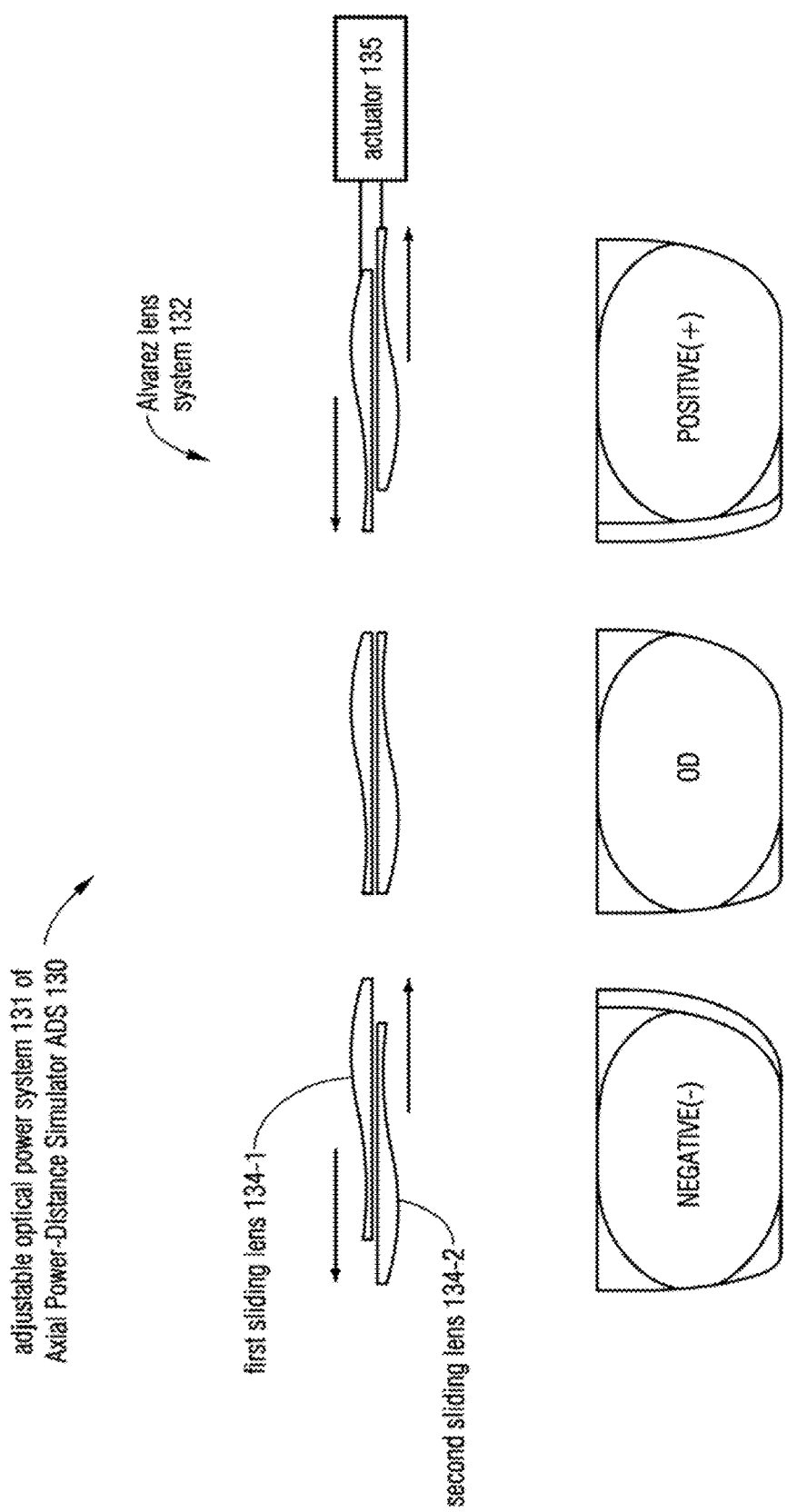
FIGS. 6A-B illustrate embodiments of an Axial Power-Distance Simulator ADS.
Figure 6B:
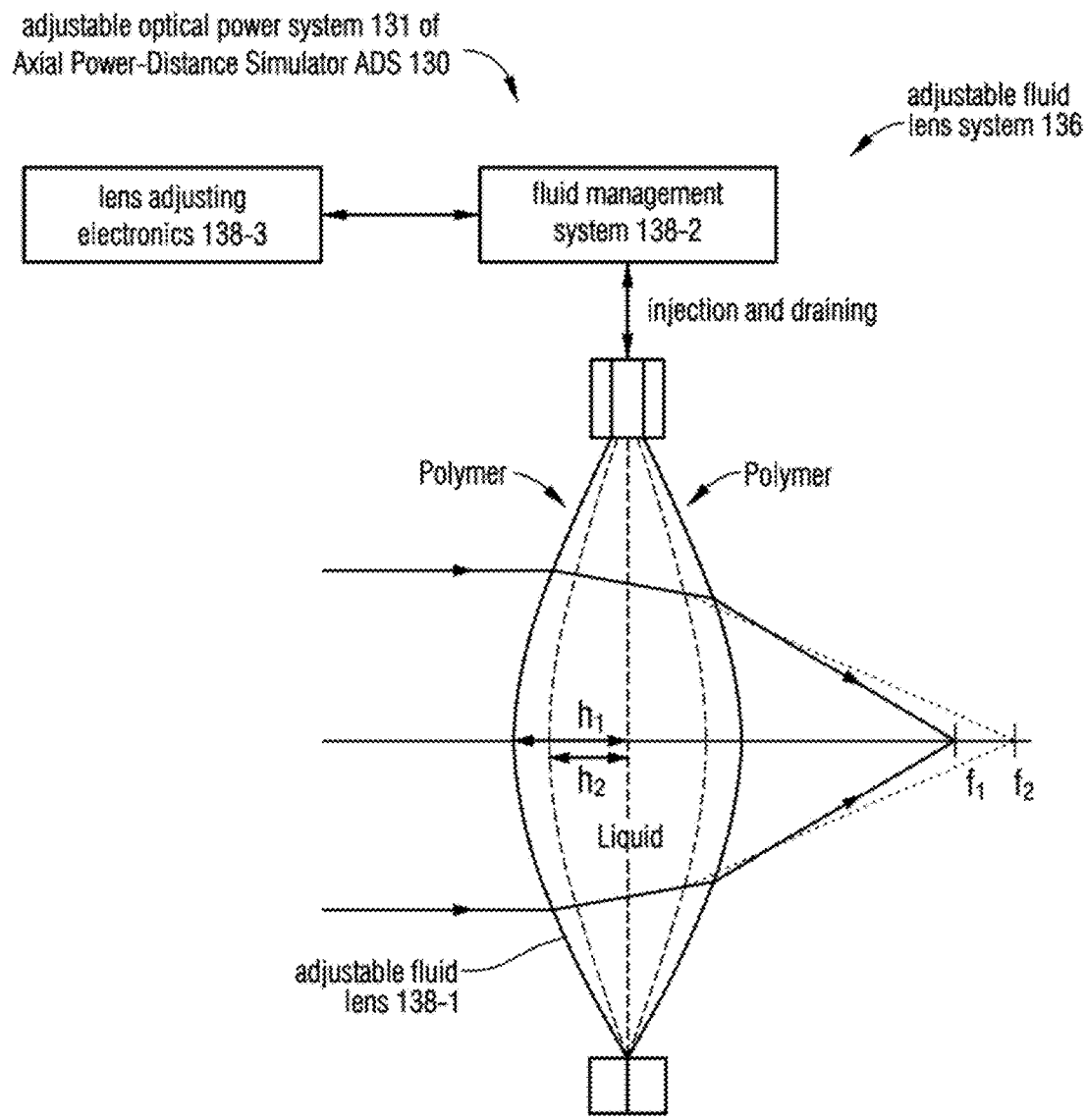

FIGS. 6A-B illustrate specific embodiments of ADS 130. FIG. 6A illustrates an ADS 130 that includes an Alvarez lens system 132. The Alvarez lens system 132 can include at least two (sliding) lenses 134-1 and 134-2 for each eye, at least one of the two lenses 134 having laterally varying curvature; and one or more actuators 135, for sliding at least one of the lenses 134 laterally relative to the other lens, thereby changing an optical refractive power of the Alvarez lens system 132 in a central region. The actuator 135 is only shown once to avoid clutter. In embodiments of the Alvarez lens system 132 the optical (refractive) power in a central region can be changed by 2 Diopters (2D) or more, without introducing substantial aberrations. The diameter of the central region can be 2, 2.5, 3 cm, or more than 3 cm. Adding 2D optical power to the ADS 130 changes the perceived image distance from far away to 1/2D=50 cm. Therefore, the ability to change the optical power by 2D is typically sufficient to change the axial optical power from OPd of the distance vision region 123*d* to OPn of the near vision region 123*n*, thereby simulating the entire range of interest. As described before, one function of the ADS 130 is to simulate the gaze distance to the object, the other function is to simulate the axial optical power of the progressive lens design 123. Different ADS 130 can integrate and implement these two functions differently.

FIG. 6B illustrates another embodiment of the ADS 130: an adjustable fluid lens system 136 that includes a pair of adjustable fluid lenses 138-1, with optical refractive power that is controlled by an amount of fluid in the fluid lenses 138-1 (only one lens shown); a fluid-management system 138-2, for adjusting the amount of fluid in the fluid lenses 138-1; and lens-adjusting electronics 138-3, for controlling the pair of adjustable fluid lenses 138-1 and the fluid-management system 138-2 to adjust the optical refractive power of the ADS 130. As shown, the adjustable fluid lens 138-1 can include a deformable rounded polymer skin that contains a liquid. The fluid management system 138-2 can inject or drain fluid from the lens 138-1. Doing so changes a center height from $h_1$ to $h_2$. By the basic law of lenses, this height change changes the focal length of the lens 138-1 from $f_1$ to $f_2$, as shown, adjusting its optical refractive power.

Many other embodiments of the ADS 130 exist, including a shape-changing lens, an index-of-refraction-changing lens, a variable mirror, a deformable optic, an aspheric lens with adjustable aperture, a liquid crystal optical element, an adjustable reflective optical element, an adjustable opto-electronic element, and an optical system with an optical component with adjustable relative position.

Figure 7:
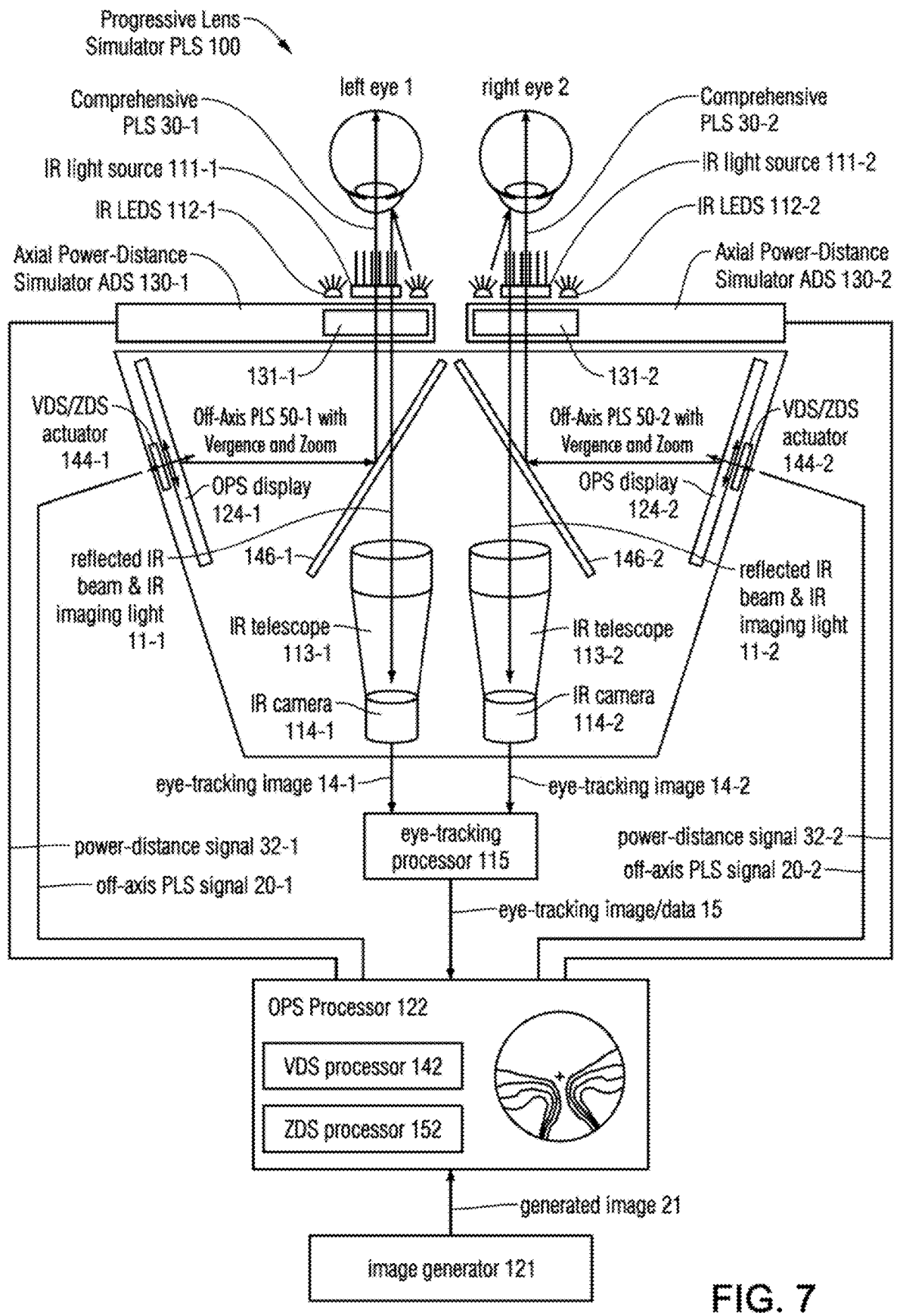
FIG. 7 illustrates a Multistage embodiment of a Progressive Lens Simulator.

FIG. 7 illustrates an embodiment of the PLS 100 in more detail. Most of the elements of the PLS 100 of FIG. 7 are specific embodiments of the general PLS 100 of FIG. 3, and will not be repeated here. Next, additional features of FIG. 7 are called out as follows.

In the PLS 100 of FIG. 7, the Eye Tracker 110 can include infrared light emitting diodes, or IR LEDs, 112-1 and 112-2, positioned close to a front of the PLS 100, to project infrared eye-tracking beams on the first eye 1 and the second eye 2; as well as infrared light sources 111-1 and 111-2, to illuminate the first eye 1 and the second eye 2 with an infrared imaging light. The infrared eye-tracking beams and the infrared imaging light get both reflected from the eyes 1 and 2, as reflected IR beam and IR imaging light 11-1 and 11-2.

The Eye Tracker 110 can further include infrared (IR) telescopes 113-1 and 113-2, with infrared (IR) cameras 114-1 and 114-2, to detect the infrared eye-tracking beams and the infrared imaging light 11-1 and 11-2, reflected from the eyes 1 and 2. The IR cameras 114-1 and 114-2 then generate the eye-tracking images 14-1 and 14-2, and send them to the eye-tracking processor 115. The eye-tracking processor 115 can process and analyze these eye-tracking images to generate eye-tracking image/data 15-1 and 15-2, or jointly 15. In some detail, the IR beams of the IR LEDs 112 are reflected as Purkinje reflections, or Purkinje spots, that reflect from the various surfaces of the eye, starting with the cornea. Tracking these Purkinje spots delivers pin-point information to track the eye position and orientation. The IR light source 111, on the other hand, generates a wide-angle IR light that can be used to image the entire frontal region of the cornea. The Eye Tracker 110 can use both the pin-point information from the reflected Purkinje spots, and the wide-angle image from the reflected imaging light (together referenced as 11) to develop the comprehensive eye-tracking image/data 15.

In the embodiment of FIG. 3 the Eye Tracker 110 directly sends eye-tracking image/data 15 into the OPS Processor 122. In the embodiment of FIG. 7, there is an intervening eye-tracking processor 115, separate from the OPS Processor 122. Several analogous variations have been contemplated for the various embodiments of PLS 100.

In operation, the OPS Processor 122 can receive the generated image 21 from the image generator 121, adjust it to generate the Off-Axis Progressive Lens Simulation signals 20-1 and 20-2, and send these Off-Axis PLS signals 20 to the OPS Displays 124-1 and 124-2, so that the OPS Displays 124 generate the Off-Axis PLS 50-1 and 50-2.

As shown, in some embodiments, the VDS processor 142 and the ZDS processor 152 can be integrated in the OPS Processor 122. In these embodiments, the Off-Axis PLS signal 20 also includes vergence and zoom components. The vergence component can instruct the VDS actuators 144-1 and 144-2 to laterally move, or rotate, the OPS Displays 124-1 and 124-2, in order to simulate the needed vergence. In these embodiments, the Off-Axis PLS 50 includes Vergence and Zoom, as indicated.

FIG. 7 illustrates that the PLS 100 can further include infrared-transmissive visible mirrors 146-1 and 146-2, one for each eye, to redirect the Off-Axis PLS 50-1 and 50-2, from the OPS display 124-1 and 124-2 to the eyes 1 and 2. With this reflection, the Off-Axis PLS 50-1 and 50-2 are redirected into the main optical pathway of the PLS 100, in the direction of the eyes 1 and 2. The Off-Axis PLS 50-1 and 50-2 are finally going through the Axial Power-Distance Simulator ADS 130-1 and 130-2. In this PLS, the ADS 130-1 and 130-2 include adjustable optical power systems 131-1 and 131-2, that can be an Alvarez lens system 132, an adjustable fluid lens system 136, or any of the other adjustable optical elements, described earlier. The ADS 130 transform the Off-Axis PLS 50 into the Comprehensive Progressive Lens Simulation PLS 30, for the patient's eyes.

It is noted that the infrared-transmissive visible mirrors 146-1 and 146-2 reflect visible light, while transmitting infrared light. Therefore, mirrors 146 are configured to reflect the Off-Axis PLS 50 towards the eyes, while transmitting the reflected infrared eye tracking beam and the infrared imaging light 11-1 and 11-2, from the eyes.

In the described embodiment of the PLS 100, the OPS Display screens 124-1 and 124-2 can be positioned peripheral to the main optical pathway of the PLS 100, while the infrared telescopes 113-1 and 113-2 of the Eye Tracker 110 can be positioned in the main optical pathway, as shown. In other embodiments, the positioned can be reversed. The mirrors 146 can be IR reflective and visible transmissive, in which case the IR telescopes 113 can be positioned peripherally, while the OPS Displays 124 can be positioned in the main optical pathway, in effect trading places.

Figure 8:
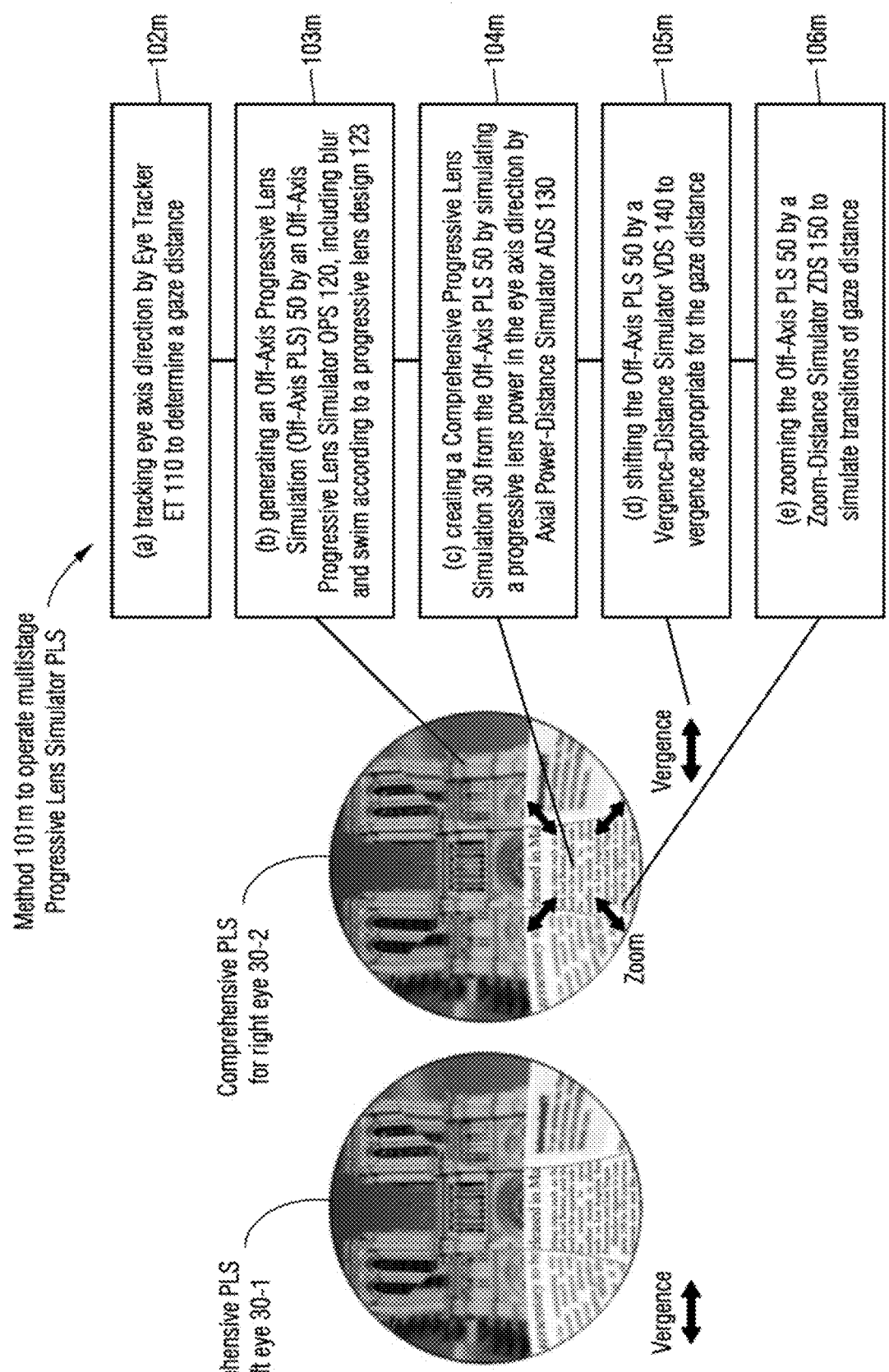
FIG. 8 illustrates a Method to operate a Multistage embodiment of a Progressive Lens Simulator.

2. Method of Operating a Progressive Lens Simulator with an Axial Power-Distance Simulator FIG. 8 illustrates a method 101m of operating a multistage embodiment of the Progressive Lens Simulator PLS 100. Here the label "m" refers to the multistage embodiment of the PLS 100. The method 101m can include the following steps.

(a) tracking 102m of an eye axis direction by an Eye Tracker 110 to determine a gaze distance of the eye;

(b) generating 103m an Off-Axis Progressive Lens Simulation (Off-Axis PLS) 50 by an Off-Axis Progressive Lens Simulator OPS 120, including blur and swim, according to a progressive lens design 123;

(c) creating 104m a Comprehensive Progressive Lens Simulation (Comprehensive PLS) 30 from the Off-Axis PLS 50 by simulating a progressive lens power in the eye axis direction by an Axial Power-Distance Simulator ADS 130;

(d) shifting 105m the Off-Axis PLS 50 by a Vergence-Distance Simulator VDS 140 to vergence appropriate for the gaze distance; and (e) zooming the Off-Axis PLS 50 by a Zoom-Distance Simulator ZDS 150 to simulate transitions of gaze distance.

Various aspects of these steps have been described before in relation to the PLS 100 embodiments of FIGS. 1-7.

The generating 103m of an Off-Axis PLS 50 can include the following.

(a) generating an image 21 by an Image Generator 121;

(b) transforming the generated image 21 into an Off-Axis PLS signal 20 by an Off-Axis Progressive Lens Simulator Processor 122 according to the progressive lens design 123; and (c) displaying an Off-Axis PLS 50 according to the Off-Axis PLS signal 20 by an Off-Axis Progressive Lens Simulator Display 124.

Various aspects of these steps have been described before in relation to the PLS 100 embodiments of FIGS. 1-7.

As described earlier, the displaying can include providing a stereoscopic Off-Axis PLS 50-1 and 50-2 for the first eye 1 and the second eye 2 by a pair of Off-Axis Progressive Lens Simulator Displays, or Screens 124-1 and 124-2.

In other embodiments, the displaying can include alternating the displaying the Off-Axis PLSs 50-1 and 50-2 for the first eye 1, and subsequently for the second eye 2, with suitable stereoscopic adjustments, by a stereoscopic alternating Off-Axis Progressive Lens Simulator Screen 124, that is controlled by an image-alternator.

In some embodiments, as shown in FIGS. 4A-B, the transforming can include receiving the generated image 21 from the Image Generator 121 by the Off-Axis Progressive Lens Simulator Processor 122; and transforming the generated image 21 into the Off-Axis PLS signal 20 by introducing a locally varying blur 126, representative of the progressive lens design 123.

In some embodiments, as shown in FIGS. 4A-B, the transforming can include receiving the generated image 21 from the Image Generator 121 by the Off-Axis Progressive Lens Simulator Processor 122; and transforming the generated image 21 into the Off-Axis PLS signal 20 by introducing a locally varying curvature, or swim, 127, representative of the progressive lens design 123.

In some embodiments, at least two of the Image Generator 121, the Off-Axis Progressive Lens Simulator Processor 122, and the Off-Axis Progressive Lens Simulator Display 124 can be integrated.

In some embodiments, as shown in FIG. 5, the method 101*m* can further include shifting 105*m* the Off-Axis PLS 50 by a Vergence-Distance Simulator VDS 140 to a vergence appropriate for the gaze distance.

In some embodiments, the simulating a vergence can include moving a screen of the Off-Axis Progressive Lens Simulator Display 124 dominantly laterally; and shifting the displayed Off-Axis PLS 50 on the Off-Axis Progressive Lens Simulator Display 124 dominantly laterally.

In some embodiments, as shown in FIG. 5, the method 101*m* can further include zooming 106*m* the Off-Axis PLS 50 by a Zoom-Distance Simulator 150 to simulate transitions of the gaze distance.

In some embodiments, at least one of the Off-Axis Progressive Lens Simulator Processor 122, the Off-Axis Progressive Lens Simulator Display 124, and the Axial Power-Distance Simulator ADS 130 can include at least one of the Vergence-Distance Simulator VDS 140 and the Zoom-Distance Simulator ZDS 150.

In some embodiments, the simulating a progressive lens power (within the creating 104*m*) can include adjusting an optical refractive power of an adjustable optical power system 131 of the Axial Power-Distance Simulator ADS 130.

In some embodiments, the adjusting can include adjusting the optical refractive power of the Axial Power-Distance Simulator ADS 130 to be consistent with the determined gaze distance. In some embodiments, the adjusting can include adjusting the Axial Power-Distance Simulator 130 to simulate a vergence corresponding to the eye axis direction.

In some embodiments, as shown in FIG. 6A, the adjustable optical power system 131 of the Axial Power-Distance Simulator ADS 130 can include an Alvarez lens system 132 that includes at least two lenses for an eye 134-1 and 134-2, at least one of the two lenses having laterally varying curvature, and one or more actuators 135. I these embodiment, the adjusting can include sliding at least one of the lenses 134-1 laterally relative to the other lens 134-2 by the one or more actuators 135, thereby changing an optical refractive power of the Alvarez lens system 132 in a central region.

In some embodiments, as shown in FIG. 6B, the adjustable optical power system 131 of the Axial Power-Distance Simulator ADS 130 can include an adjustable fluid lens system 136 that includes a pair of adjustable fluid lenses 138-1, with refractive power that is controlled by an amount of fluid in the fluid lenses; a fluid management system 138-2, for adjusting the amount of fluid in the fluid lenses; and lens adjusting electronics 138-3, for controlling the pair of adjustable fluid lenses 138-1 and the fluid management system 138-2. In these embodiments, the adjusting can include adjusting the amount of fluid in the fluid lenses 138-1 by the fluid management system 138-2 under the control of the lens adjusting electronics 138-3, thereby changing the optical refractive power of the adjustable optical power system 131. In some embodiments, the adjustable optical power system 131 can include a shape-changing lens, an index-of-refraction-changing lens, a variable mirror, a deformable optic, an aspheric lens with adjustable aperture, a liquid crystal optical element, an adjustable reflective optical element, an adjustable opto-electronic element, and an optical system with an optical component with adjustable relative position. As before, aspects and elements of this method 101*m* have been described earlier in relation to FIGS. 1-7.

3. Integrated Progressive Lens Simulator

In this section, another embodiment of the Progressive Lens Simulator 100 will be described. Numerous elements of this embodiment have been already described in relation to FIGS. 1-8 and will not be repeated, only referred to where needed.

Figure 9:
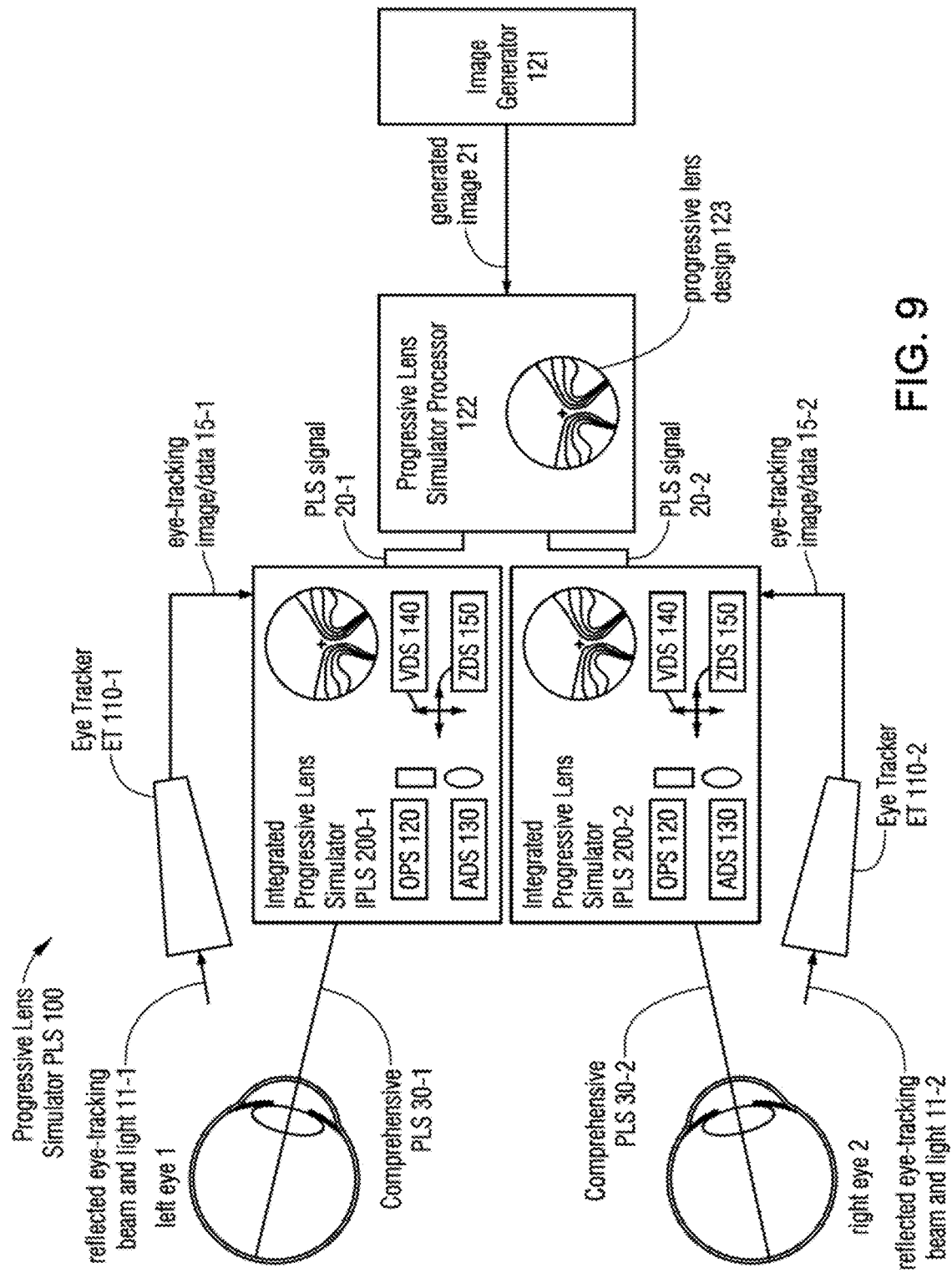
FIG. 9 illustrates an Integrated Progressive Lens Simulator.

FIG. 9 illustrates a Progressive Lens Simulator 100 that includes an Eye Tracker 110, for tracking an eye axis direction to determine a gaze distance; an Integrated Progressive Lens Simulator (IPLS) 200, for creating a Comprehensive Progressive Lens Simulation (Comprehensive PLS) 30 according to a progressive lens design 123 by simulating a progressive lens power in the eye axis direction, in combination with generating an Off-Axis progressive lens simulation (Off-Axis PLS) 50. On a general level, embodiments of the IPLS 200 can perform some, or all, of the functions of some, or all, of the OPS 120, the ADS 130, the VDS 140 and the ZDS 150 of the previously described multistage PLS 100, each referenced with a representative symbol.

In some embodiments, the PLS 100 can include an Image Generator 121, for generating an image 21; and a Progressive Lens Simulator Processor 122, for transforming the generated image 21 into a Comprehensive PLS signal 20-1 and 20-2 according to the progressive lens design 123, and for coupling the generated PLS signal 20-1 and 20-2 into the Integrated Progressive Lens Simulator 200 for creating the Comprehensive PLS 30-1 and 30-2. In some embodiments, the Image Generator 121 and the Progressive Lens Simulator Processor 122 can be integrated into the IPLS 200.

Just as the multistage PLS 100 could include a single OPS display 124, or a pair of OPS displays 124-1 and 124-2, the PLS 100 of FIG. 9 can also include a single IPLS 200, or a pair of IPLS 200-1 and 200-2, as shown, for providing a stereoscopic Comprehensive PLS 30-1 and 30-2 for the first eye 1 and for the second eye 2.

In the single IPLS 200 embodiments, the IPLS 200 can be a stereoscopic alternating Integrated Progressive Lens Simulator 200, controlled by an image-alternator, for alternating the generating the Comprehensive PLS 30-1 for the first eye 1, and subsequently 30-2 for the second eye 2, with suitable stereoscopic adjustments.

In some embodiments, similarly to FIGS. 4A-B, the Progressive Lens Simulator Processor 122 can be configured to receive the generated image 21 from the Image Generator 121; and to create an Off-Axis PLS signal-component of the Comprehensive PLS signal 20 by introducing a locally varying blur 126 into the generated image 21, representative of the progressive lens design 123.

In some embodiments, similarly to FIGS. 4A-B, the Progressive Lens Simulator Processor 122 can be configured to receive the generated image 21 from the Image Generator 121; and to create an Off-Axis PLS signal-component of the Comprehensive PLS signal 20 by introducing a locally varying curvature, or swim, 127 into the generated image 21, representative of the progressive lens design 123.

In some embodiments, similarly to FIG. 5, the Progressive Lens Simulator PLS 100 can include a Vergence-Distance Simulator VDS 140, for simulating a vergence for the displayed Comprehensive PLS 30 at the gaze distance. In some embodiments, the VDS 140 is integrated into the IPLS 200. In some cases, the Vergence-Distance Simulator VDS 140 can be configured to simulate a vergence for the Comprehensive PLS 30 at the gaze distance by at least one of moving the Integrated Progressive Lens Simulator 200-1 and 200-2 dominantly laterally, and shifting the created Comprehensive PLS 30 on the Integrated Progressive Lens Simulator 200-1 and 200-2 dominantly laterally.

In some embodiments, similarly to FIG. 5, the Progressive Lens Simulator PLS 100 can include a Zoom-Distance Simulator 150, for zooming the Comprehensive PLS 30 to represent a change in the gaze distance. In some embodiments, the Integrated Progressive Lens Simulator PLS 200 can include at least one of the Vergence-Distance Simulator 140 and the Zoom-Distance Simulator 150.

The Integrated Progressive Lens Simulator 200 can be configured to simulate a primary function of the ADS 130: the optical power of the progressive lens design 123 in the eye axis direction by creating the Comprehensive PLS 30 with light rays having a vergence related to the gaze distance. As described before, the simulated optical power can be selected by combining the simulation of the distance of the viewed object with the simulation of the axial power of the progressive lens design 123.

Various embodiments of the IPLS 200 will be described next, in relation to FIGS. 10-13. A shared aspect of these embodiments is that they simulate a further aspect of the Comprehensive PLS 30: the (di)vergence of the light rays, emanating from the viewed object according to the gaze distance. The (di)vergence is often thought of as an important component of the overall visual experience, used by our brain to analyze and perceive the viewed images. An aspect of the embodiments in FIGS. 1-8 was that the Comprehensive PLS 30 of the PLS 100 was generated by flat OPS Displays 124, thus generating flat wavefronts. These flat wavefronts do not fully represent the true viewing, or gaze, distance. In contrast, FIGS. 10-13 illustrate embodiments of the IPLS 200 that at least have the capacity to generate the Comprehensive PLS 30 with a non-flat wavefront, the light rays diverging from every image point, thereby representing the viewing, or gaze distance more faithfully, more life-like.

Figure 10:
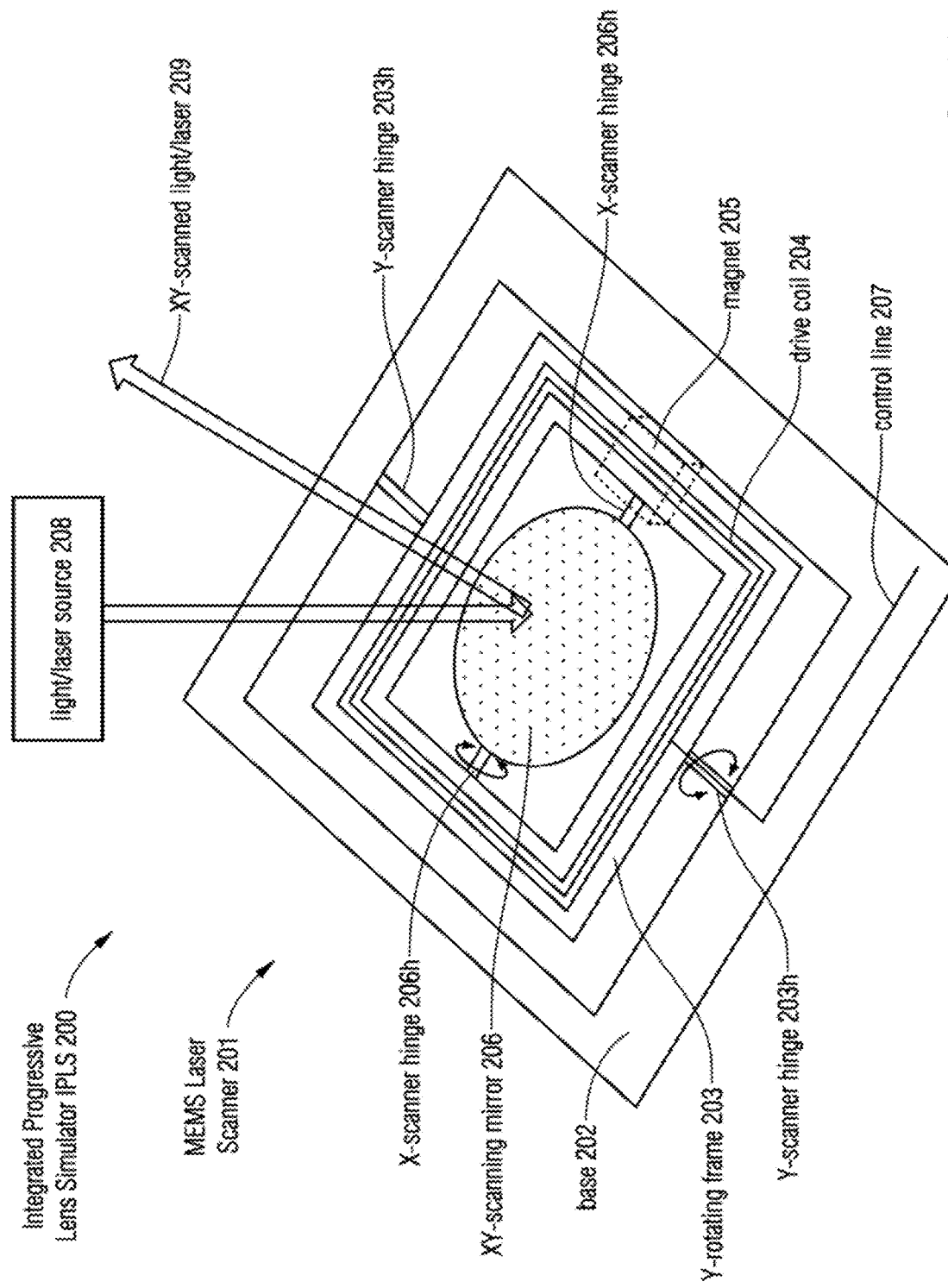
FIG. 10 illustrates a MEMS Laser Scanner.

FIG. 10 illustrates that the IPLS 200 can include a Micro Electro Mechanical System (MEMS) Laser Scanner 201 that includes a light, or laser source 208, for generating and projecting a light; and a XY scanning mirror 206, for reflecting and scanning the projected light as an XY-scanned light 209. In this IPLS 200 the light source 208 can be an LED, a collection of different color LEDs, a laser, a collection of different color lasers, and a digital light projector. The MEMS Laser Scanner 201 can include a base 202, such as a frame, and a first/Y-scanner hinge system 203h, to rotate a Y-rotating frame 203. The Y-rotating frame 203 can support a drive coil 204 that is energized through a control line 207. When a current is flowing from the control line 207 to the Y-rotating frame 203, it induces a magnetic field in the drive coil 204. A magnet 205, positioned under the Y-rotating frame 203 exerts a torque on the energized drive coil 204, thereby rotating the Y-rotating frame 203.

The IPLS 200 can further include a second/X-scanner hinge system 206h, optionally embedded in the first/Y-scanner hinge system 203, for reflecting and scanning the projected light by the XY-scanning mirror 206 in two spatial dimensions as the XY-scanned light 209. This X-scanner hinge system 206h can be driven by various embodiments of electro-mechanical actuators. The scanning speed of the MEMS Laser Scanner 201 can be high enough so that it projects the Comprehensive PLS 30 with a high enough refresh rate that the patient perceives it as realistic. Helpfully, the images used in evaluating vision, are typically static, or only slowly moving, thus the demands on the refresh rates and therefore scanning rates are lower than, e.g. in fast-action video games or live TV.

Figure 11A:
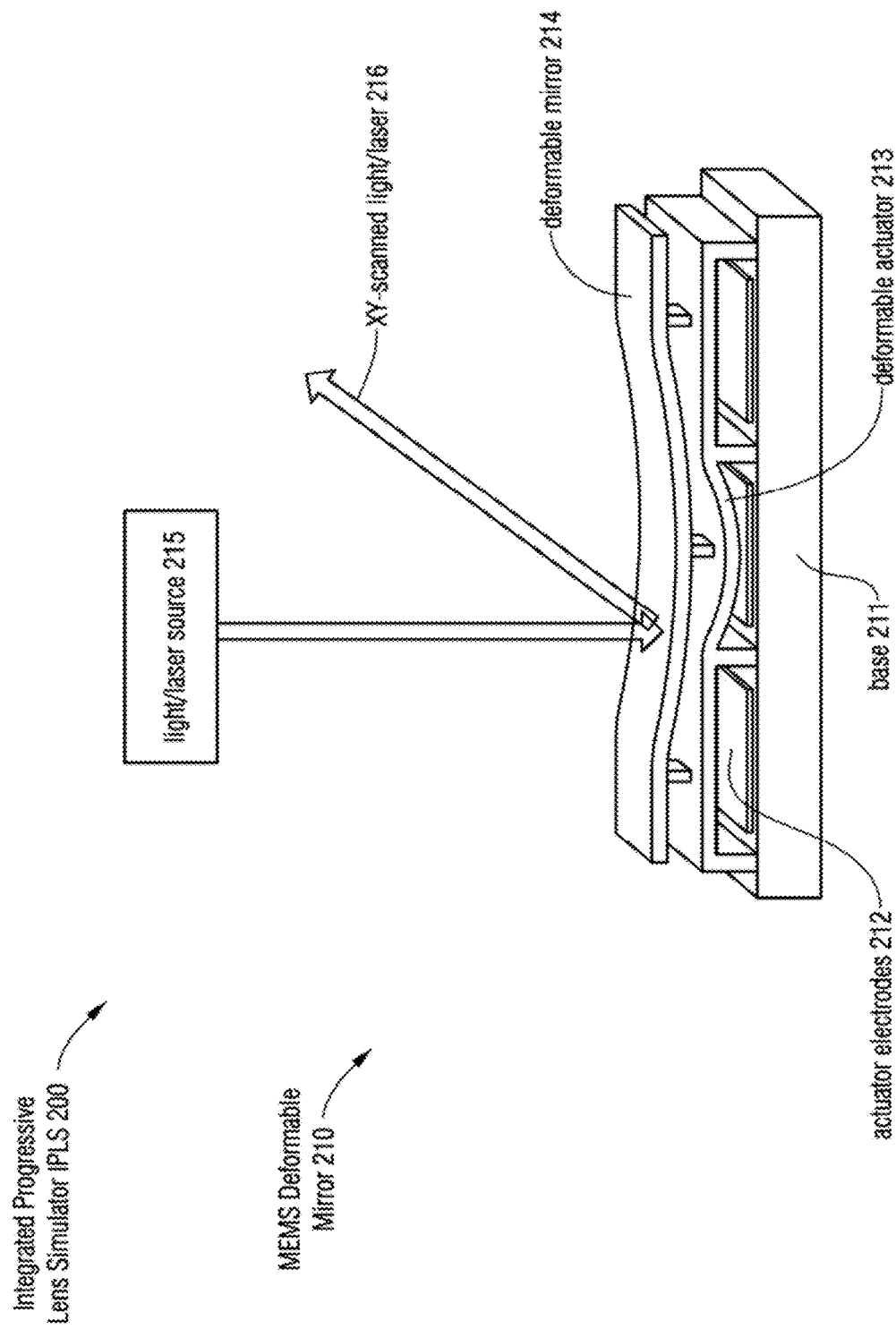
FIGS. 11A-B illustrate a MEMS Deformable Mirror, and a MEMS Actuated Mirror Array.

FIG. 11A illustrates another embodiment of the IPLS 200. This IPLS 200 includes a Micro Electro Mechanical System (MEMS) Deformable Mirror 210 that includes a light/laser source 215, for generating and projecting a light; and a deformable mirror 214, for reflecting and scanning the projected light into an XY-scanned light 216. The light/laser source 215 can be an LED, a collection of different color LEDs, a laser, a collection of different color lasers, or a digital light projector. The deformable mirror 214 can include a base 211, actuator electrodes 212, and an array of actuators 213, for deforming the deformable mirror 214 in a segmented manner. In the shown IPLS 200, the actuators 213 are deformable as well. Each segment of the deformable mirror 214 can redirect the XY-scanned light/laser 216, as the light is scanned across the deformable mirror 214.

Figure 11B:
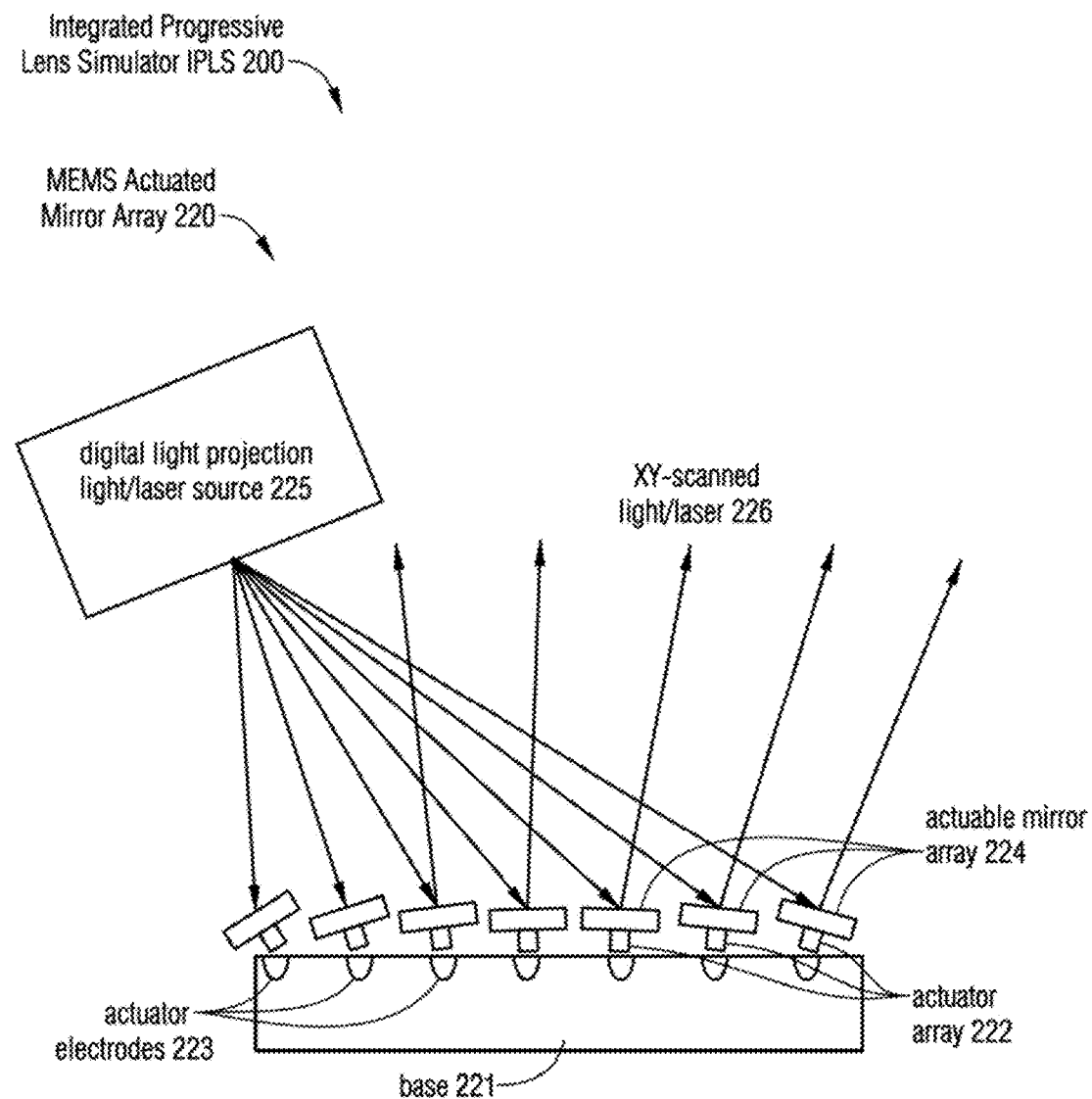

FIG. 11B illustrates another embodiment of the IPLS 200 that includes a Micro Electro Mechanical System (MEMS) Actuated Mirror Array 220, with a light/laser/digital light source 225, for generating and projecting a light. The light source 225 can include at least one of a LED, an LED group, a laser, a laser group, a scanning light source, and a digital light projector. The MEMS Actuated Mirror Array 220 can include a base 221, supporting an actuator array 222, actuator electrodes 223, to carry control signals for the actuators 222, and an array of actuable mirrors 224, for actuably reflecting the light from the laser/light source 225 into a XY-scanned light/laser 226.

In the embodiments of FIGS. 11A and 11B the light can be provided in a scanned manner, or in a simultaneous manner, illuminating all mirror segments in FIG. 11A, or all actuable mirrors in FIG. 11B essentially simultaneously. The latter embodiments can use a digital light projector 225, for example.

Figure 12A:
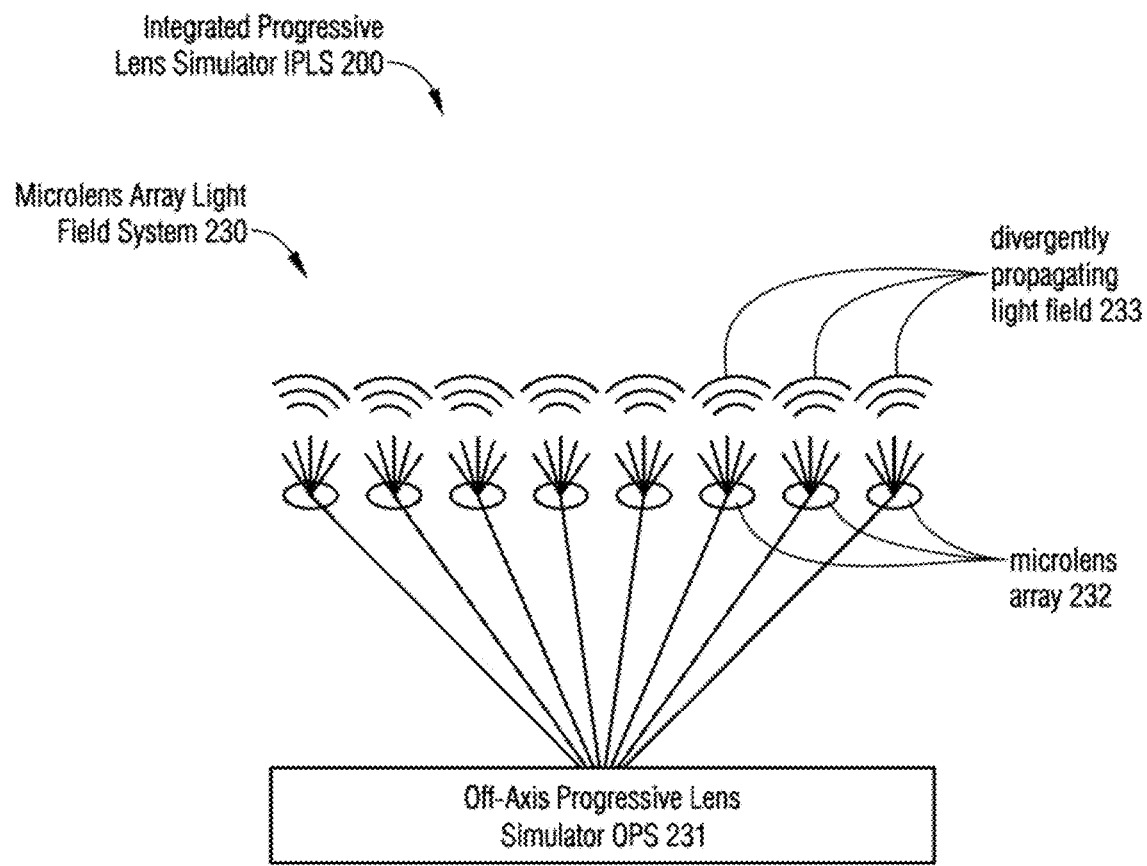
FIGS. 12A-D illustrate a Microlens Array, a MEMS Curved Mirror Array, a LED projector Array, and a Deformable display embodiment of the IPLS.

FIG. 12A shows an IPLS 200 that includes a Microlens Array Light Field System 230 that includes an Off-Axis Progressive Lens Simulator 231, for the generating the Off-Axis PLS 50. This Off-Axis Progressive Lens Simulator 231 can be the Off-Axis PLS 120 from FIGS. 1-7. The Microlens Array Light Field System 230 can also include a microlens array 232, for receiving the generated Off-Axis PLS 50, and for transmitting it as a divergently propagating light field 233, to simulate a progressive lens power in the eye axis direction, a vergence related to the gaze distance, or a combination of these two, as described earlier. Microlens arrays are favored in related opto-electronic systems, such as virtual reality goggles, to create very life-like visual experiences by generating light fields with non-flat wavefronts.

Figure 12B:
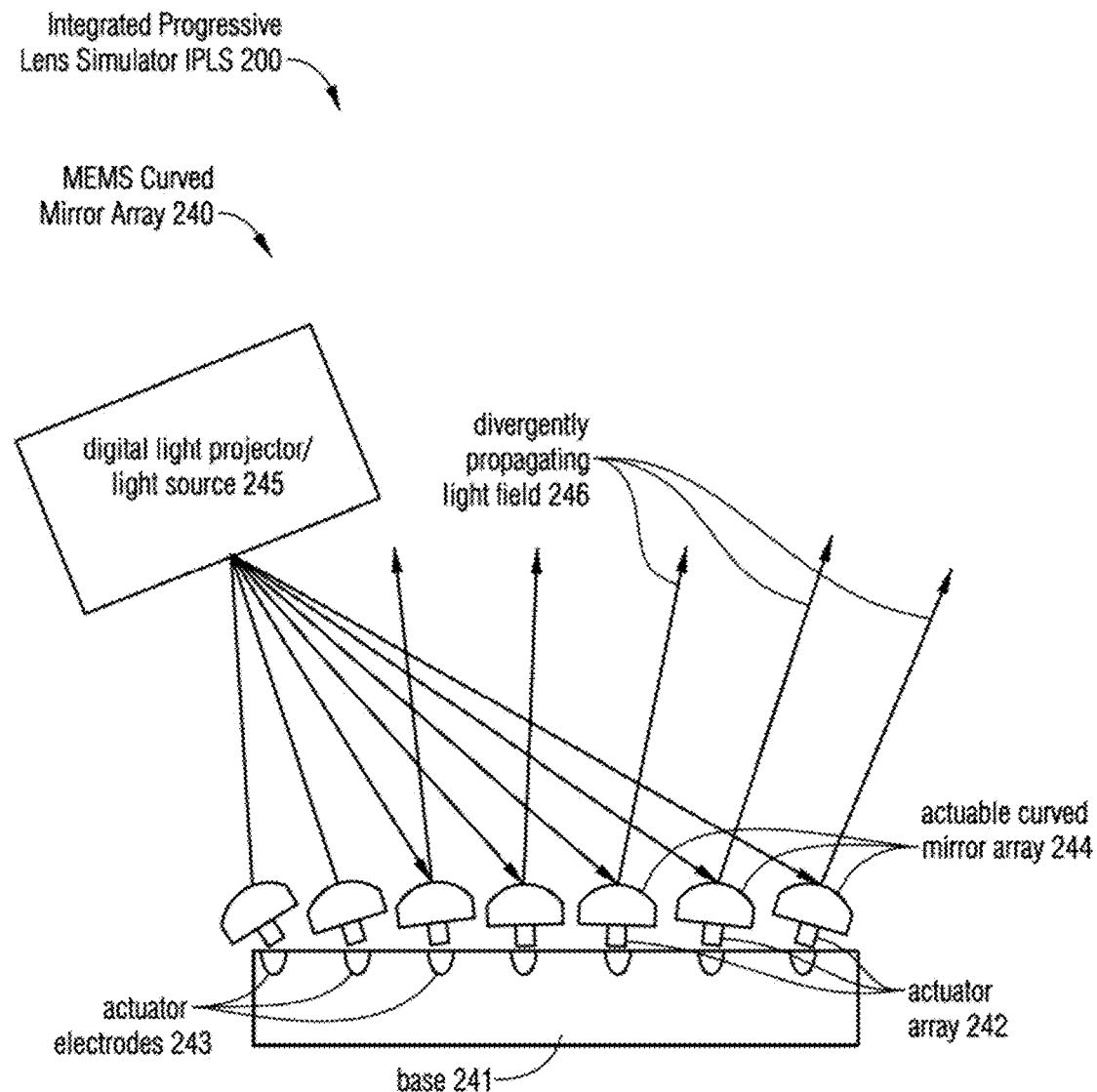

FIG. 12B illustrates another embodiment of the IPLS 200. This IPLS 200 is analogous to the IPLS 200 in FIG. 11B with one difference: it utilizes curved mirrors in place of the flat mirrors of the IPLS 200 of FIG. 11B. As such, this IPLS 200 includes a Micro Electro Mechanical System (MEMS) Curved Mirror Array 240, including a digital light projector, or light source 245, for generating and projecting a light, the light source 245 including at least one of a LED, an LED group, a laser, a laser group, a scanning light source, and a digital light projector. The IPLS 200 further includes a base 241, an actuator array 242, controlled by actuator electrodes, and an array of actuable curved mirrors 244, for reflecting the light to generate a vergence related to the gaze distance; wherein the curved mirrors 244 include at least one of fixed mirrors and actuable mirrors. The light, reflected from the curved mirrors forms a divergently propagating light field 246. In some embodiments, the curvature of the actuable curved mirrors 244 can be modified according to the gaze distance, to further increase the life-like divergence of the wavefront.

Figure 12C:
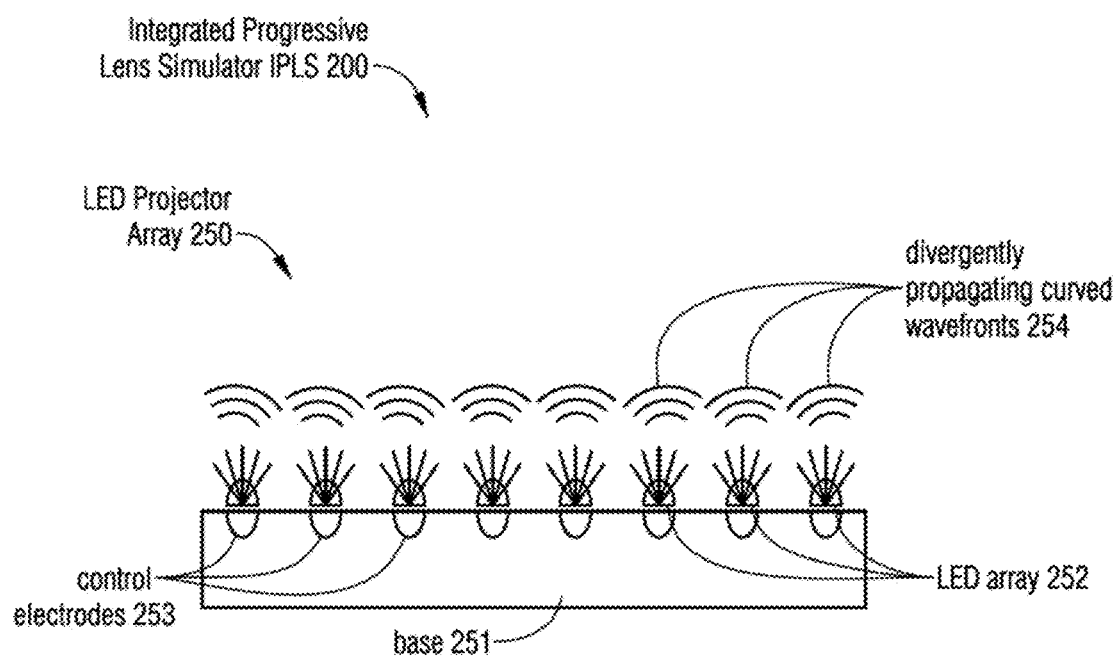

FIG. 12C illustrates yet another embodiment of the IPLS 200 that includes a LED Projector Array 250 that includes a base 251, a LED array 252, controlled by control electrodes 253, for creating the Comprehensive PLS 30 with a divergently propagating curved wavefront 254, for the simulating the progressive lens power in the eye axis direction, in combination with generating the Off-Axis progressive lens simulation.

Figure 12D:
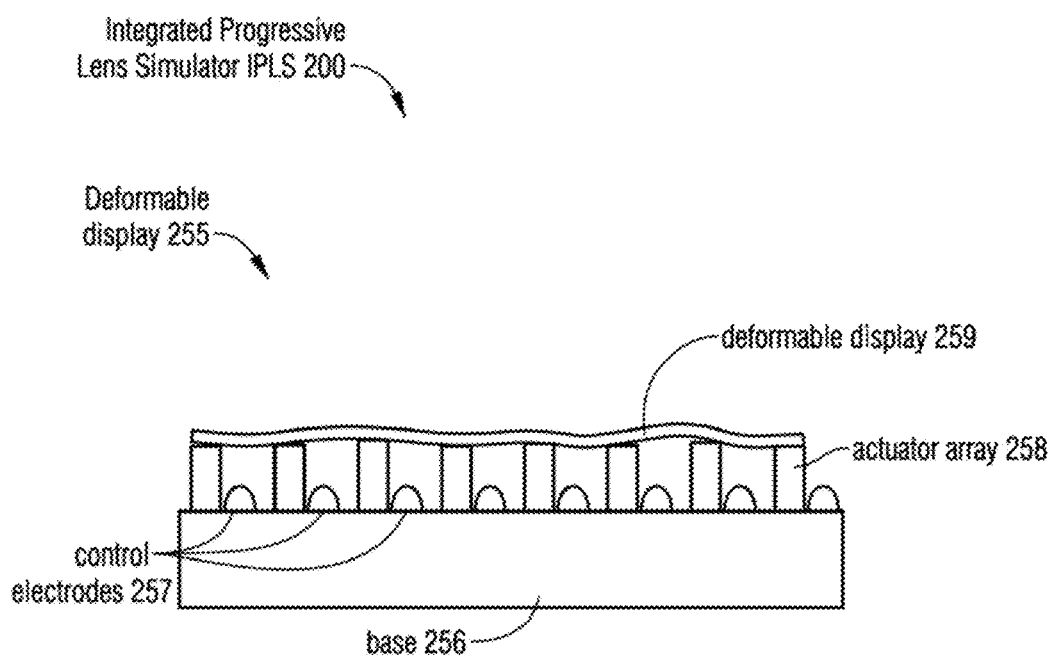

FIG. 12D illustrates yet another embodiment of the IPLS 200 that includes an actuated deformable display 259. As with other embodiments, this one can also be formed on a base, or substrate 256. A set of control electrodes 257 may carry control signals to control actuators of an actuator array 258. The deformable display 259 can be deformably disposed on top of the actuator array 258. The deformable display 259 can be an OLED display, and any soft, flexible, or deformable equivalents. The actuators 258 can deform the display 259 by expanding and contracting in a vertical, normal direction. An aspect of this Deformable display 255 embodiment is that it is capable of emitting a non-flat wavefront, thus improving the life-like divergence of the emitted wavefront.

Figure 13:
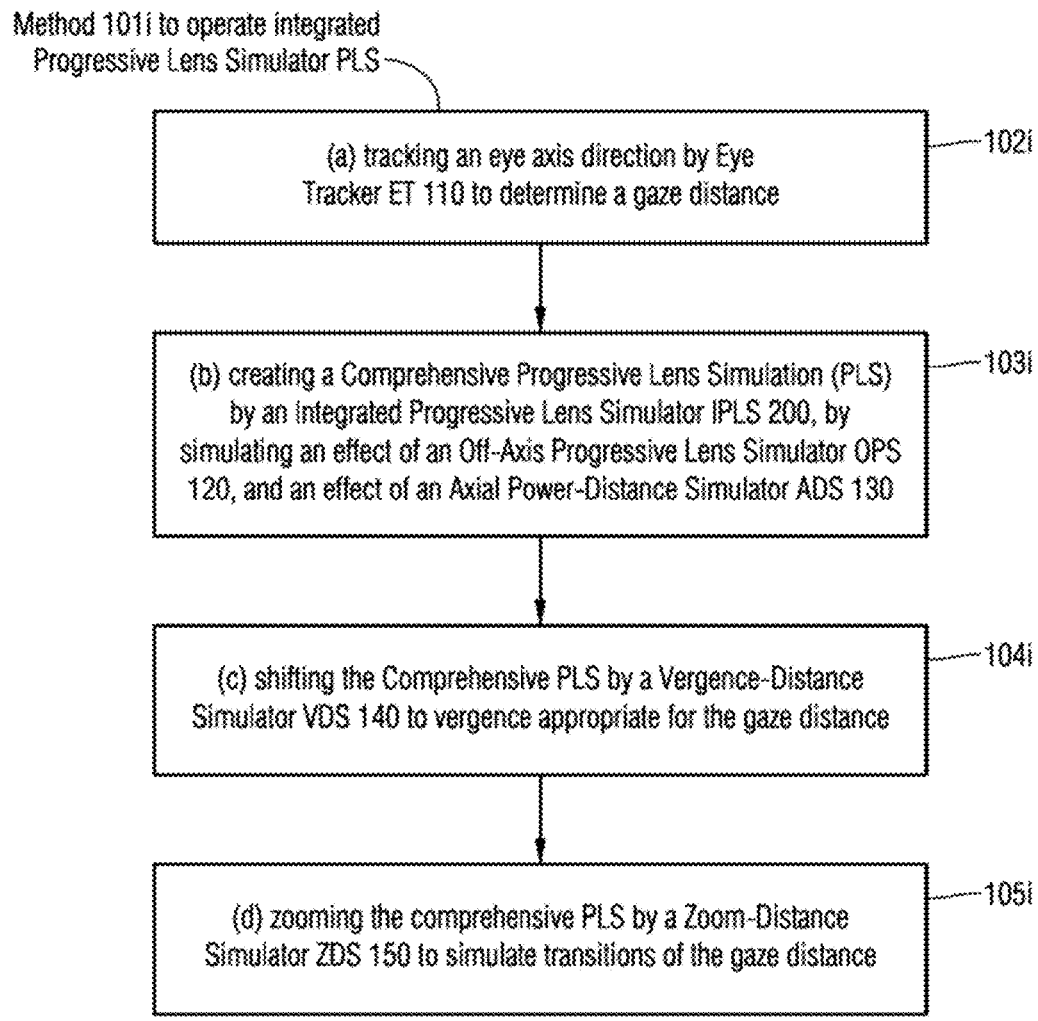
FIG. 13 illustrates a method of operating an Integrated Progressive Lens Simulator.

FIG. 13 illustrates a method 101*i* of operating the Progressive Lens Simulator 100. Here the label "i" refers to the PLS 100 being integrated, such as the IPLS 200. The method 101*i* can include the following steps.

(a) tracking 102*i* an eye axis direction by Eye Tracker ET 110 to determine a gaze distance;

(b) creating 103*i* a Comprehensive Progressive Lens Simulation (PLS) by the Integrated Progressive Lens Simulator IPLS 200, by simulating an effect of an Off-Axis Progressive Lens Simulator OPS 120, and an effect of an Axial Power-Distance Simulator ADS 130;

(c) shifting 104*i* the Comprehensive PLS by a Vergence-Distance Simulator VDS 140 to vergence appropriate for the gaze distance; and (d) zooming 105*i* the comprehensive PLS by a Zoom-Distance Simulator ZDS 150 to simulate transitions of the gaze distance.

4. Head-Mounted Progressive Lens Simulator

Figure 14:
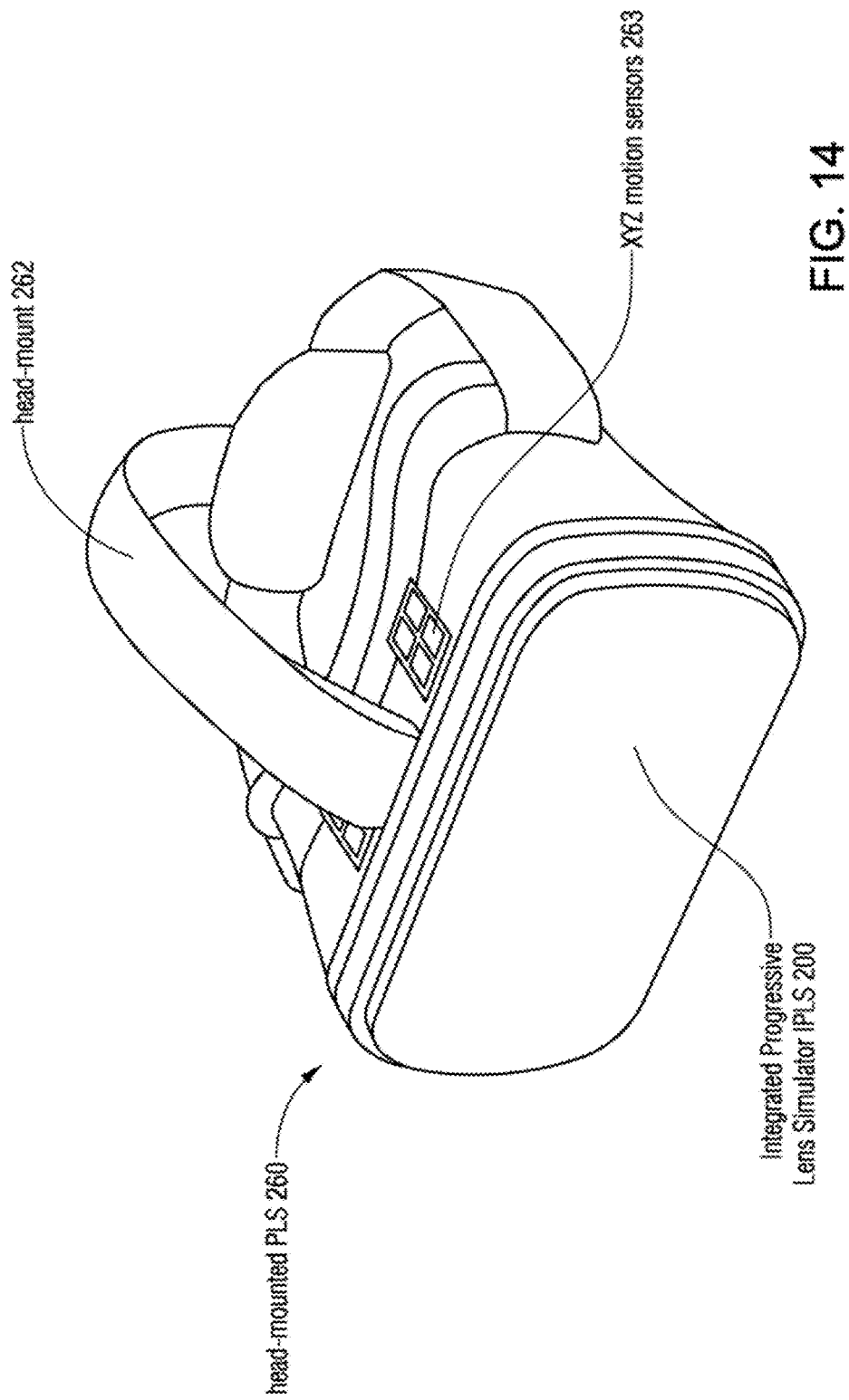
FIG. 14 illustrates a head-mounted Integrated Progressive Lens Simulator.

FIGS. 14-15 illustrate a head-mounted PLS 260, secured to a patient's head by a head-mount 262. The head-mounted PLS 260 can include an Integrated Progressive Lens Simulator (IPLS) 200 and XYZ position or motion sensors 263. The IPLS 200 can be any of the IPLS 200 embodiments described in relation to FIGS. 9-13. Some embodiments of the head-mounted PLS 260 can include any embodiment of the PLS 100.

In some detail, embodiments of the PLS 100 can include an Eye Tracker 110, for tracking an eye axis direction to determine a gaze distance; and the Integrated Progressive Lens Simulator 200, for creating a Comprehensive Progressive Lens Simulation (PLS) 30 by simulating a progressive lens power in the eye axis direction, in combination with generating an Off-Axis progressive lens simulation (Off-Axis PLS) 50. In these embodiments, the Eye Tracker 110 and the Integrated Progressive Lens Simulator 200 can be implemented in a head-mounted display, virtual reality viewer, or goggles. Next, two specific embodiments of the head-mounted PLS 260 are described in more detail.

Figure 15A:
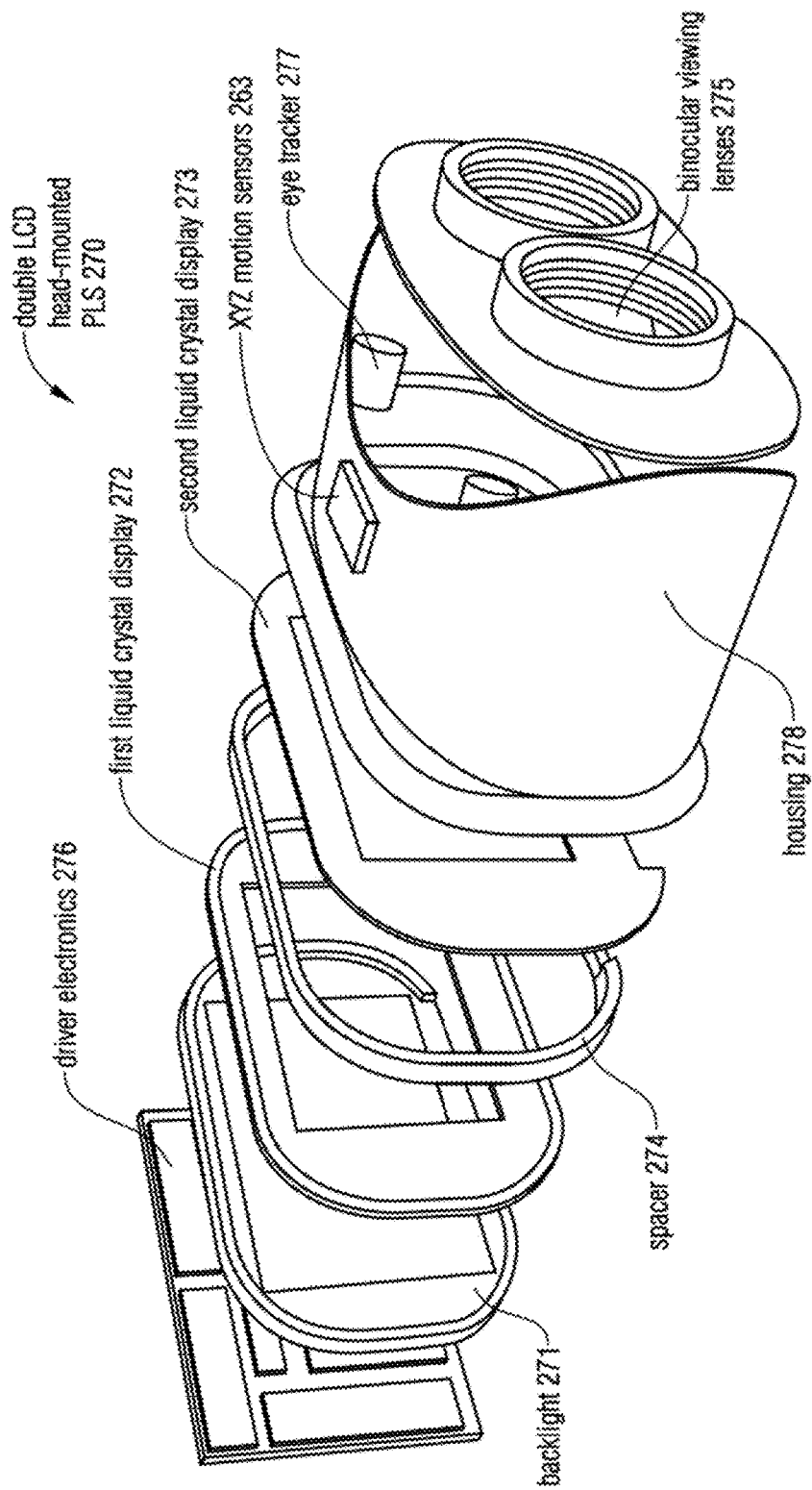
FIGS. 15A-B illustrate embodiments of Head-mounted Integrated Progressive Lens Simulators.

FIG. 15A illustrates a double LCD head-mounted PLS 270, as an embodiment of the head-mounted PLS 260. The double LCD head-mounted PLS 270 can include a backlight 271; a first liquid crystal display 272, positioned in front of the backlight 271; a second liquid crystal display 273, spaced apart from the first liquid crystal display 271 by a spacer 274, for together simulating a progressive lens design 123 by creating a light field effect, and thereby a Comprehensive PLS 30. The double LCD head-mounted PLS 270 can further include binocular viewing lenses 275, and eye tracker 277 that can be an embodiment of the Eye Tracker 110. Because of the extreme spatial constraints, the eye tracker 277 can be configured to track the eye movements from high angles. In other embodiments, an IR reflective visible transmissive mirror can be used as part of the eye tracker 277, in analogy with the similar mirrors 146 in the embodiment of FIG. 7. Finally, the above elements can be energized and controlled by a driver electronics 276. The elements 271-276 together can be thought of as forming the IPLS 200.

The field of virtual reality goggles is rapidly expanding. These goggles are more and more capable of generating life-like visual experiences, and therefore their technology can be promisingly implemented and adapted for use in embodiments of the head-mounted PLS 260 to create the Comprehensive PLS 30.

In particular, the light field effect generated by the head-mounted PLS 260 can be three dimensional, or four dimensional. The latter (4D) technology also represents the depth of focus perception, making objects that are in front or behind the object plane blurrier. Doing so further enhances the life-likeness of the visual perception.

Some embodiments of the PLS 100 can use not only XYZ position sensors but XYZ motion sensors 263. Picking up not only the position and direction of the head-mounted PLS 260/270, but also sensing a motion of a wearer of the head-mounted PLS 260/270 can be integrated into the control software that runs on the driver electronics 276, or in a separate computer. The XYZ motion sensor 263, or motion sensors can include at least one of an accelerometer, a gyroscope, and a magnetometer. These can all contribute to sensing the motion, position and direction of the user's gaze.

Figure 15B:
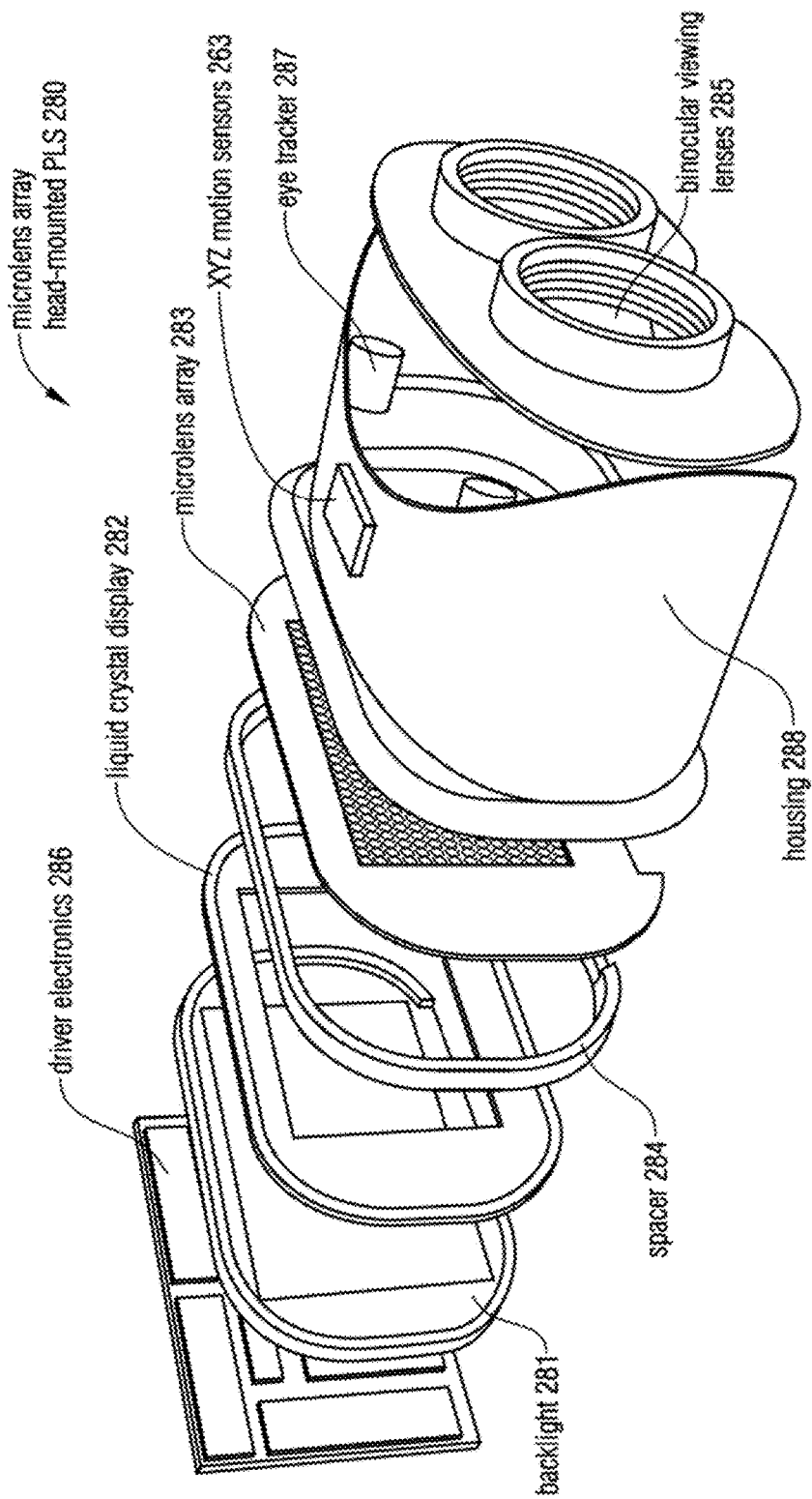

FIG. 15B illustrates another, related embodiment of the head-mounted PLS 260: a microlens array head-mounted PLS 280. The microlens array head-mounted PLS 280 can include a backlight 281; a liquid crystal display 282, positioned in front of the backlight 281; and a microlens array 283, spaced apart from the liquid crystal display 282 by a spacer 284, for together simulating a progressive lens design 123 by creating a light field effect, and thereby creating a Comprehensive PLS 30. As discussed earlier in the context of FIG. 12A, microlens arrays can create light field effects and non-flat wavefronts particularly effectively, thereby increasing the life-likeness of the visual experience of the Comprehensive PLS 30. The light field effect can be three dimensional or four dimensional.

The microlens array head-mounted PLS 280 can further include binocular viewing lenses 285; and an eye tracker 287. As before, the eye tracker 287 can be an embodiment of the Eye Tracker 110. In some cases, the eye tracker 287 has to be able to work at high angles, or with the help of an IR reflective, visible transmissive mirror, similar to the mirror 146 in FIG. 7. Finally, the above elements can be energized and controlled by a driver electronics 286. The elements 281-286 together can be thought of as forming the IPLS 200.

This embodiment can further include at least one XYZ position, direction, or motion sensor 263, for sensing a position, direction, or motion of a wearer of the head-mounted PLS 280. This sensor can sense the position, the direction, or the motion of the head-mounted PLS 280, thereby aiding the generation of the Comprehensive PLS 30.

All embodiments of FIGS. 14 and 15A-B can further include a housing 278/288 for accommodating the Eye Tracker 277/287, and the Integrated Progressive Lens Simulator 200. Also, some of the computers used in the PLS 100 and IPLS 200, such as the Progressive Lens Simulator Processor 122, can be implemented in a self-standing computer, separate from the head-mount. The self-standing computer can communicate with the head-mounted PLS 260/270/280 via a wired connection, or via a Bluetooth connection.

Finally, in some embodiments, head-mounted PLS 260/270/280 can involve augmented reality glasses, wherein the Comprehensive Progressive Lens Simulation 30 is generated from an image viewed via the augmented reality glasses.

5-6. Guided Lens Design Exploration System and Method for a Progressive Lens Simulator As mentioned in the introductory part, FIGS. 3-15 describe Progressive Lens Simulators 100 that generate Comprehensive Progressive Lens Simulations 30, in order to enable the patients to explore many progressive lens designs 123 via high quality, life-like visual experiences. A class of these PLS 100 systems can be operated by the optometrists in the traditional manner, using only verbal feedbacks from the patients. In this section, additional classes of systems are described, that empower the patient to control and to manage the exploration of as many progressive lens designs as they desire under their own control.

FIGS. 16-29 illustrate that important additional systems can be employed in some embodiments of GPS 10 to control, to manage and to accelerate the exploration of a substantial number of progressive lens designs. These GPS 10 systems can be managed and controlled by the patient, by an optometrist, or a vision technician. In these embodiments, the patient can provide feedback and optionally control signals in response to the Comprehensive Progressive Lens Simulation 30 of a progressive lens design 123. As described in the early sections, this feature is a powerful departure from existing optometry systems, at least for the listed dozen reasons.

Figure 16:
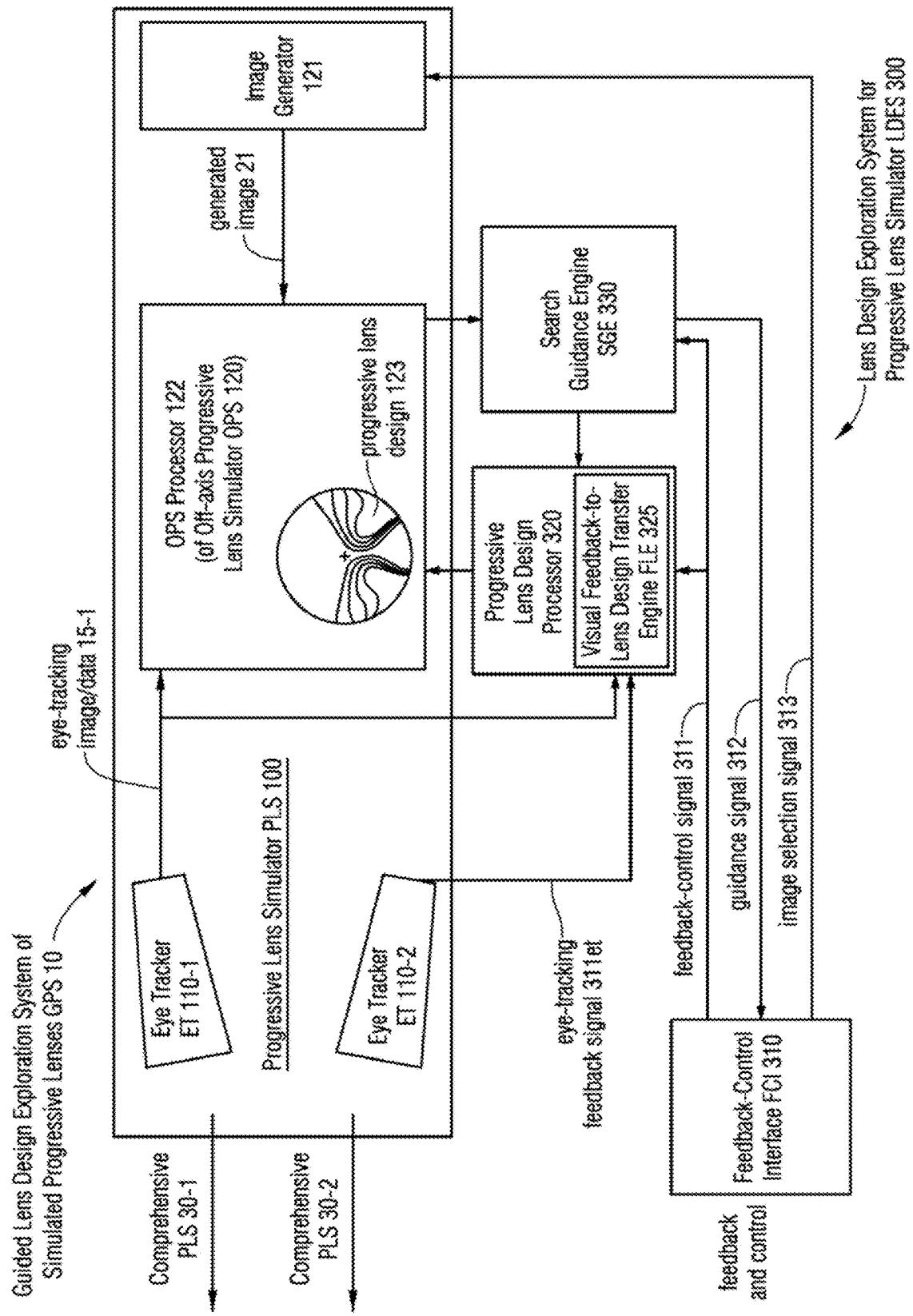
FIG. 16 illustrates a Progressive Lens Simulator with a Lens Design Exploration System.

FIG. 16 illustrates that in embodiments, a PLS 100 can be combined with a Lens Design Exploration System for Progressive Lens Simulator (LDES) 300. This combined system includes the Progressive Lens Simulator 100, for generating a Comprehensive Progressive Lens Simulation 30 utilizing a progressive lens design 123 with Design Factors 420 for a patient, and for receiving a Visual Feedback 430 in response to the Comprehensive Progressive Lens Simulation (PLS) 30. Several embodiments of the PLS 100 have been described in relation to FIGS. 3-15. Any one of those embodiments, and any of their combinations can be used in the description below.

The LDES 300 can further include a Progressive Lens Design processor 320, coupled to the Progressive Lens Simulator 100, for modifying the progressive lens design 123 in response to the Visual Feedback 430, and transmitting the modified progressive lens design 123 to the Progressive Lens Simulator 100 to generate a modified Comprehensive Progressive Lens Simulation 30 for the patient with the modified progressive lens design 123. The progressive Lens Design Processor 320 can be part of, or even integrated into, the OPS 120.

The LDES 300 can further include a Feedback-Control Interface 310, coupled to the Progressive Lens Design processor 320, for receiving the Visual Feedback 430 from an operator, selected from the group consisting of a joystick, a touchpad, a mouse, an audio interface, an external tablet GUI, and an internal visual-interface GUI, and forwarding the received Visual Feedback in the form of a feedback-control signal 311 to the Progressive Lens Design processor 320. Other embodiments may include the Eye tracker 110, coupled to the Progressive Lens Design processor 320, for receiving a Visual Feedback 430 in a form of an objective patient vision measurement. In other embodiments, other systems can provide objective feedbacks, including Purkinje-spot based imagers, Scheimpflug systems, and OCT systems.

Also, the Progressive Lens Design Processor 320 can base some of its calculations of eye modeling. This may involve imaging some of the ophthalmic layers in the eye, and then building an eye model like the widely used Holladay model.

Several modes of operation of the embodiments of the LDES 300 have been contemplated regarding the feedback.

(1) Some LDES 300 are operated by the patient himself/herself. The PLS 100 generates the Comprehensive PLS 30 for the patient, who evaluates the visual experience and directly enters a subjective feedback into the FCI 310.

(2) In other embodiments of LDES 300, the Visual Feedback may only be indirect. The patient may only express a verbal feedback, such as the last modification made the visual experience of the Comprehensive PLS 30 better or worse, and a trained operator, technician, or the optometrist herself/himself may enter a control signal 311 via the FCI 310.

(3) Other LDES 300 can be based on objective patient feedback and do not require an active, or subjective, patient feedback. For example, the Eye Tracker 110 can monitor the patient's eye movements and draw conclusions from the monitoring. E.g. if the jitter of the patient's eye increases, or the patient struggles to focus in response to a modification of the Comprehensive PLS 30, then the Eye Tracker 110 may report this to the Progressive Lens Design Processor 320 of the LDES 300. In response, a software of the Progressive Lens Design Processor 320 may conclude that the modification was undesirable, and undo the modification, or try a different one.

(4) Finally, in some embodiments of LDES 300, the objective patient feedback, or objective patient vision measurement, such as the rapidity of the patient's eye movement, or inability to focus, may be monitored not by a computer software but by the operator of the LDES 300, such as the optometrist herself/himself without an express, or subjective cooperation of the patient. In such embodiments, the monitoring operator can enter the feedback or control into the FCI 310 that transforms it into a feedback-control signal 311.

The combination of the PLS 100 and LDES 300, described next, can be operated in any of the above four modes, or in some combination of these modes. Sometimes the patient, technician, optometrist, or some combination of more than one of these possible sources providing a feedback or a control input together will be referred to as "the operator". Also for this reason, the inputs into the FCI 310, and the signal 311 outputted by FCI 310 can be feedback, control, and any combination of feedback and control input and feedback and control signals. These possibilities and combinations will be inclusively referred to as feedback-control input and feedback-control signal 311.

Figure 17C:
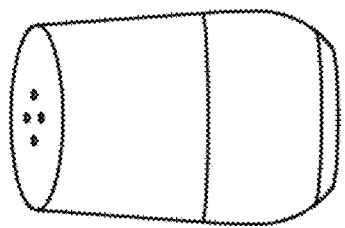
FIGS. 17A-F illustrate embodiments of patient controllers.
Figure 17F:
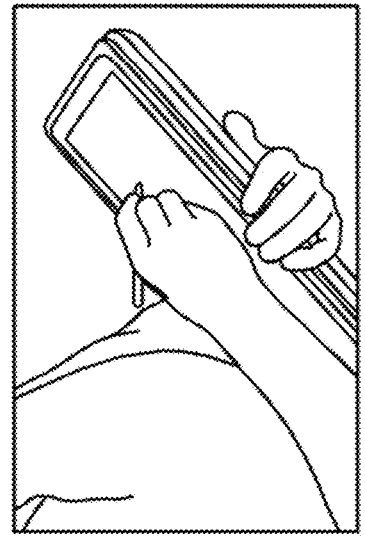
Figure 17B:
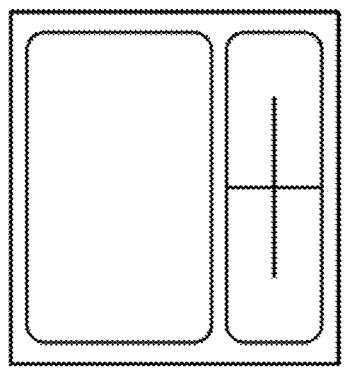
Figure 17E:
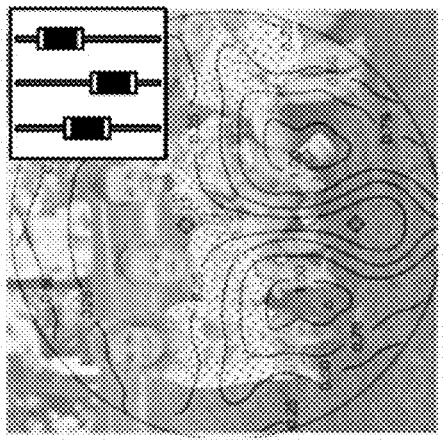
Figure 17A:
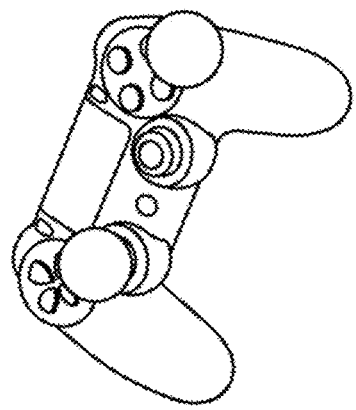
Figure 17D:
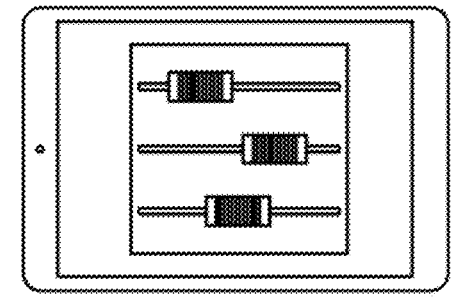

FIGS. 17A-F illustrate that the Feedback-Control Interface FCI 310, where an operator can enter a feedback or control input, can have numerous embodiments. These include a (twin) joystick FCI 310-1 in FIG. 17A, a touchpad-mouse FCI 310-2 in FIG. 17B, an audio interface FCI 310-3 in FIG. 17C, an external tablet GUI (Graphical User Interface) FCI 310-4 in FIG. 17D, and an internal visual-interface GUI FCI 310-5, possibly overlaid with the visual experience of the Comprehensive PLS 30 in FIG. 17E. As mentioned in the second embodiment of the LDES 300, in some cases the patient can only provide a subjective feedback which then can be used by an operator, or technician to actually enter an input into an indirect FCI 310-6. FIG. 17F symbolically illustrates such combined operator modes. In analogous embodiments, the optometrist can enter an input into a tablet, an iPad, a fixed terminal or a GUI of the LDES 300.

It is a non-obvious, challenging task to "translate" the feedback into an actionable command on how to modify the progressive lens design 123 in response to the feedback. Several embodiments will be described next to carry out this translation, in response to the feedback, or "Visual Feedback". The method of exploring and changing the progressive lens design in response to a Visual Feedback in general will be referred to as a method 400 of Progressive Lens Simulation. Several embodiments of this method will be described next.

Figure 18A:
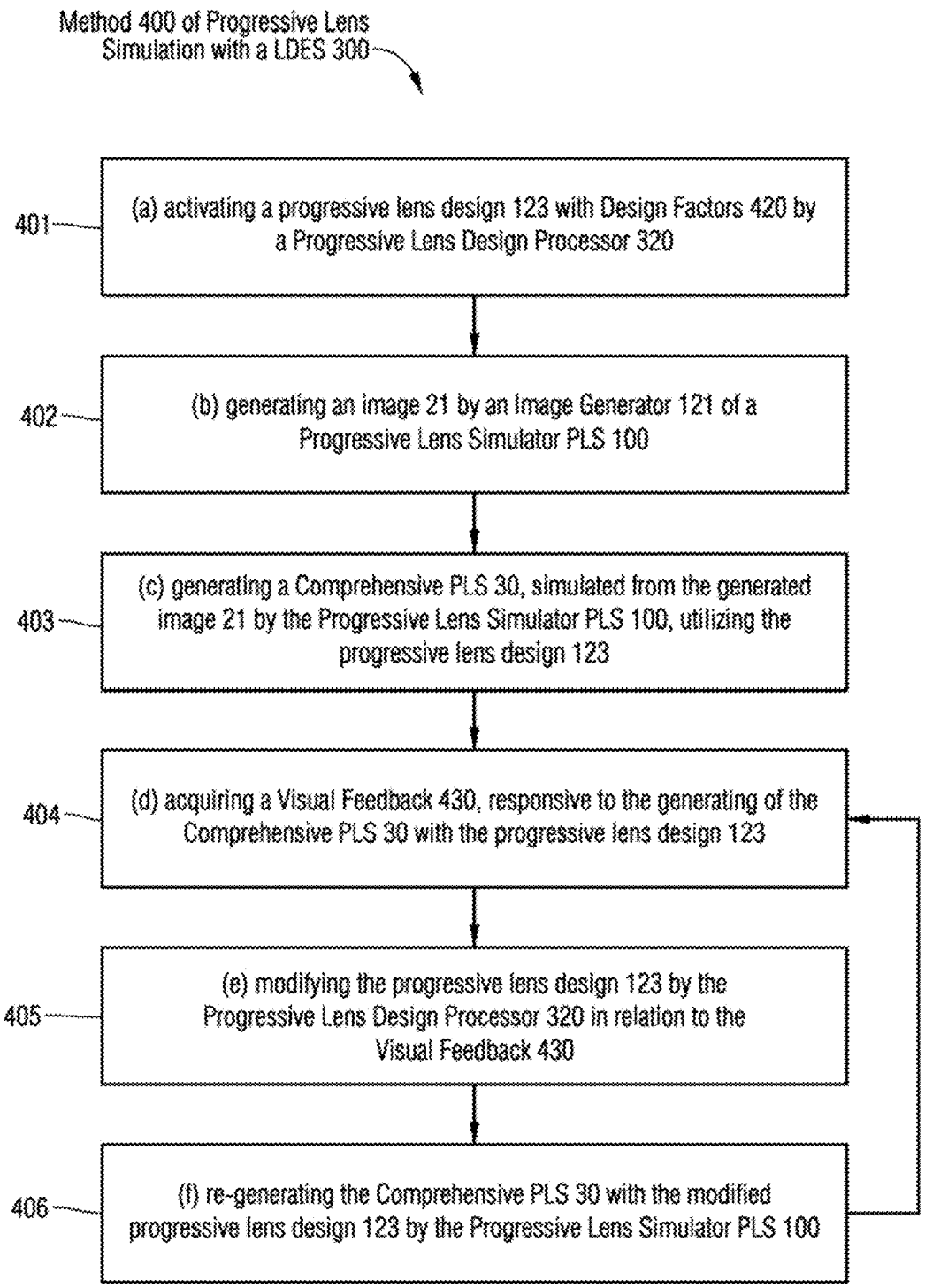
FIGS. 18A-B illustrate methods of Progressive Lens Simulation in some detail.

FIG. 18A illustrates the method 400 of Progressive Lens Simulation, comprising:

(a) activating 401 a progressive lens design 123 with Design Factors 420 by a Progressive Lens Design Processor 320;

(b) generating 402 an image 21 by an Image Generator 121 of a Progressive Lens Simulator 100;

(c) generating 403 a Comprehensive Progressive Lens Simulation (PLS) 30, simulated from the generated image 21 by the Progressive Lens Simulator 100, utilizing the progressive lens design 123;

(d) acquiring 404 a Visual Feedback 430, responsive to the generating of the Comprehensive PLS 30 with the progressive lens design 123;

(e) modifying 405 the progressive lens design 123 by the Progressive Lens Design Processor 320 in relation to the Visual Feedback 430; and (f) re-generating 406 the Comprehensive PLS 30 with the modified progressive lens design 123 by the Progressive Lens Simulator 100.

The method 400 can typically involve repeating steps (d)-(e)-(f) until the Visual Feedback 430 indicates a satisfactory outcome of the method.

The activating 401 the progressive lens design 123 with a Progressive Lens Design Processor 320 can be in response to a progressive lens design selection based on a preparatory measurement. The generating the image 21 by an Image Generator 121 can be in response to an image selection. Embodiments of the activating 401 are broadly understood. The activating 401 of the progressive lens design 123 can include recalling the progressive lens design 123 from a memory, or from a storage medium. The activating 401 can also include that the Progressive Lens Design Processor 320 computes or models the progressive lens design 123 from some model parameters. Whichever way the progressive lens design 123 is activated, the Progressive Lens Simulator 100 can be generating 403 a Comprehensive Progressive Lens Simulation PLS 30 from the generated image 21 by utilizing the activated progressive lens design 123.

Figure 18B:
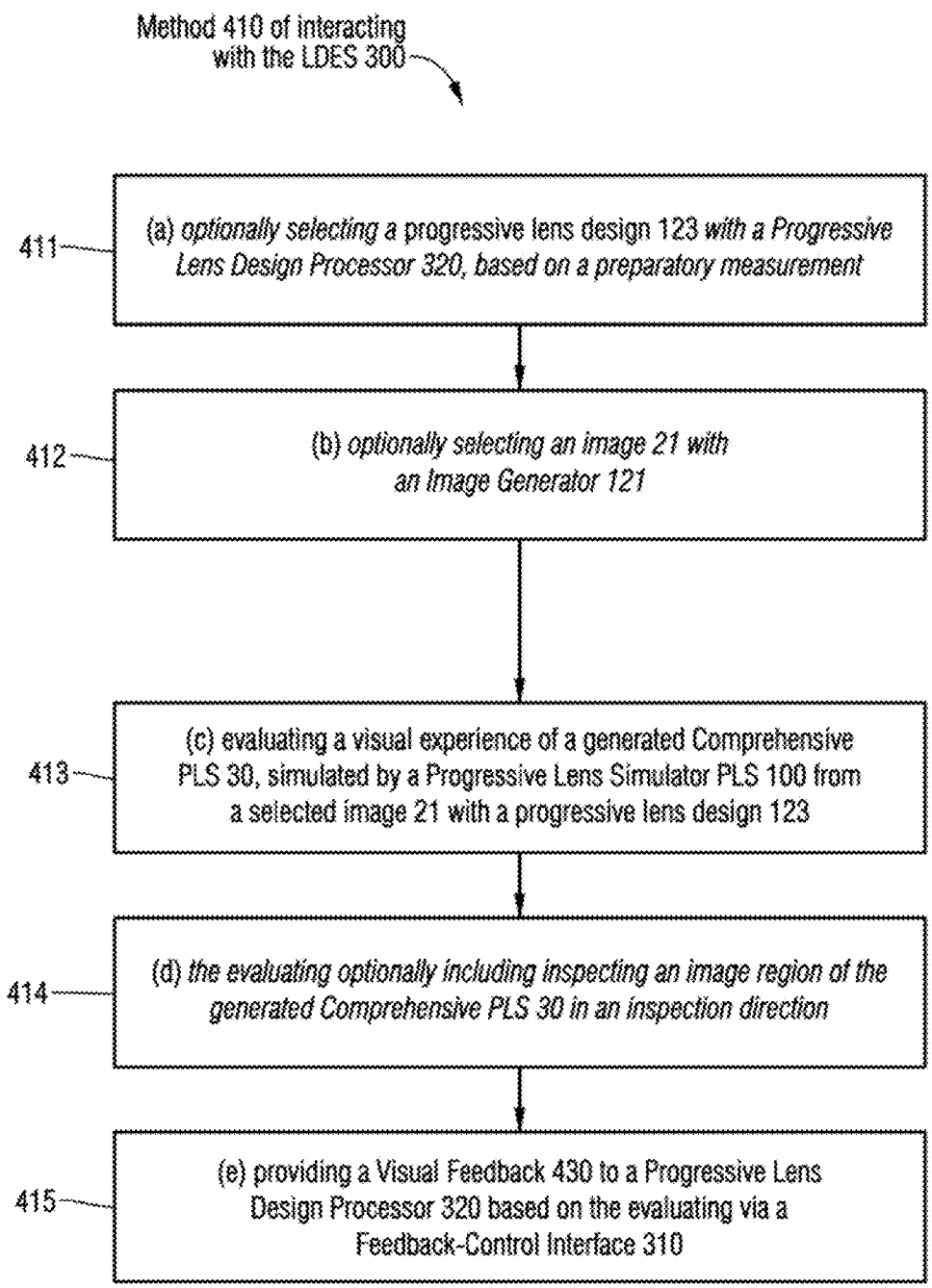

The above steps of the method 400 are typically performed by the PLS 100 and the LDES 300. FIG. 18B illustrates steps of a method 410 of an operator interacting with the LDES 300 to carry out the method 400. The method 410 can include the following steps.

(a) optionally selecting 411 a progressive lens design 123 with a Progressive Lens Design Processor 320, based on a preparatory measurement;

(b) optionally selecting 412 an image 21 with an Image Generator 121;

(c) evaluating 413 a visual experience of a generated Comprehensive PLS 30, simulated by a Progressive Lens Simulator PLS 100 from a selected image 21 with a progressive lens design 123;

(d) the evaluating optionally including inspecting 414 an image region of the generating a Comprehensive PLS 30 in an inspection direction; and (e) providing 415 a Visual Feedback 430 to a Progressive Lens Design Processor 320 based on the evaluating via a Feedback-Control Interface 310.

Figure 19B:
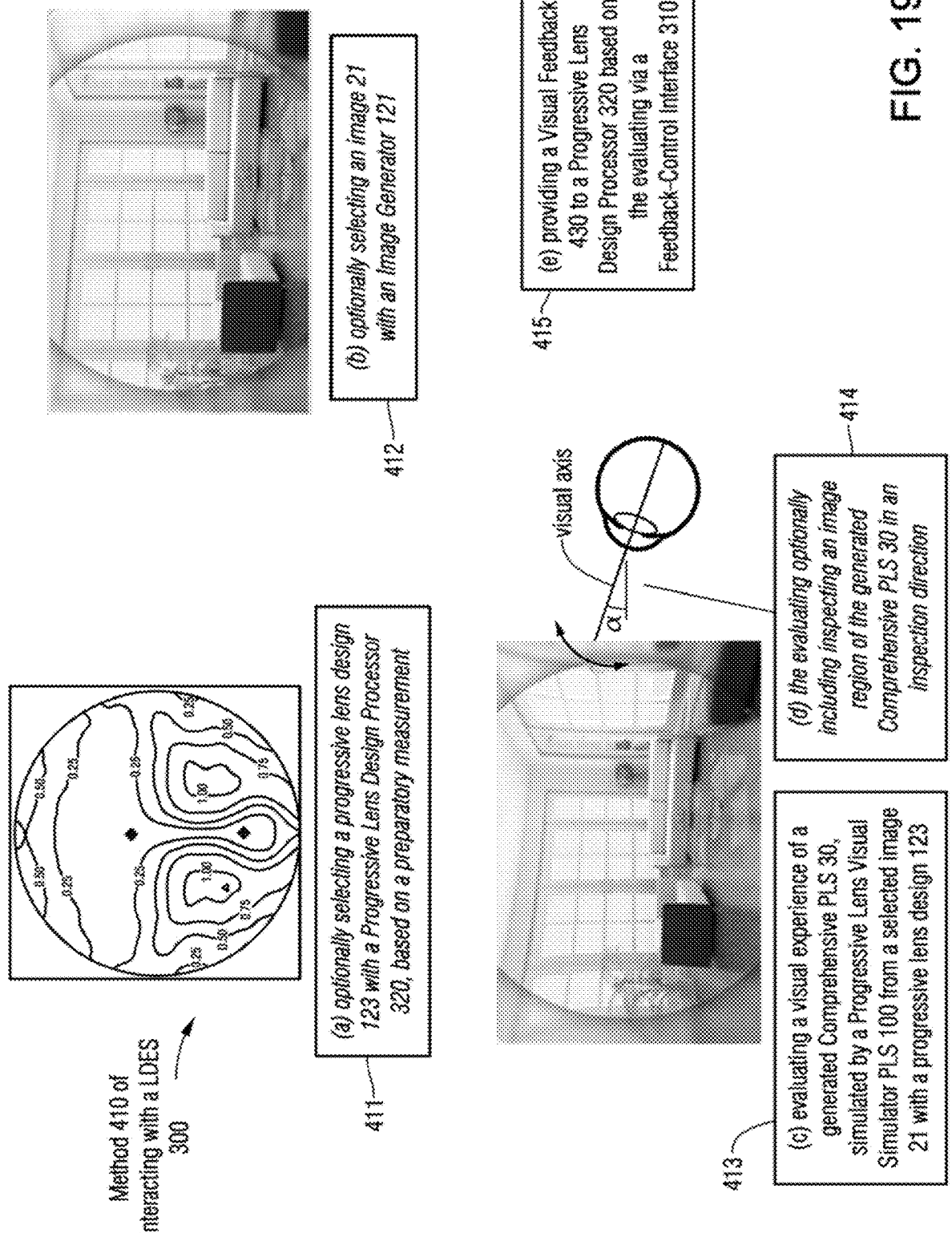

FIGS. 19A-B illustrate the method steps that were described in FIGS. 18A-B. FIG. 19A illustrates the steps of the method 400 in some detail that were described in relation to FIG. 18A. For the activating step 401, the progressive lens design 123 is illustrated with a progressive lens design 123 defined by contour lines. For the generating an image step 402, a generated image 21 is shown. For the generating the comprehensive PLS step 403, it is shown that generating the Comprehensive PLS 30 from the generated image 21 can involve introducing a blur 126 into the peripheral regions of the image 21, and introducing a swim 127 by bending the straight lines of the image 21, both based on detailed optical calculations. The acquiring step 404 can involve a measurement of a jitter of an angle α of the visual axis of the eye as shown: excessive jitter may indicate excessive discomfort with the Comprehensive PLS 30 of the progressive lens design 123.

FIG. 19B illustrates the steps of the method 410, executed by an operator of the PLS 100–LDES 300 system. The steps of the method 410 are shown in relation to the steps of the method 400 that are executed by the combined PLS 100–LDES 300 system itself. These steps once again closely correspond to the steps described in FIG. 18B.

Figures 20A, 20B:
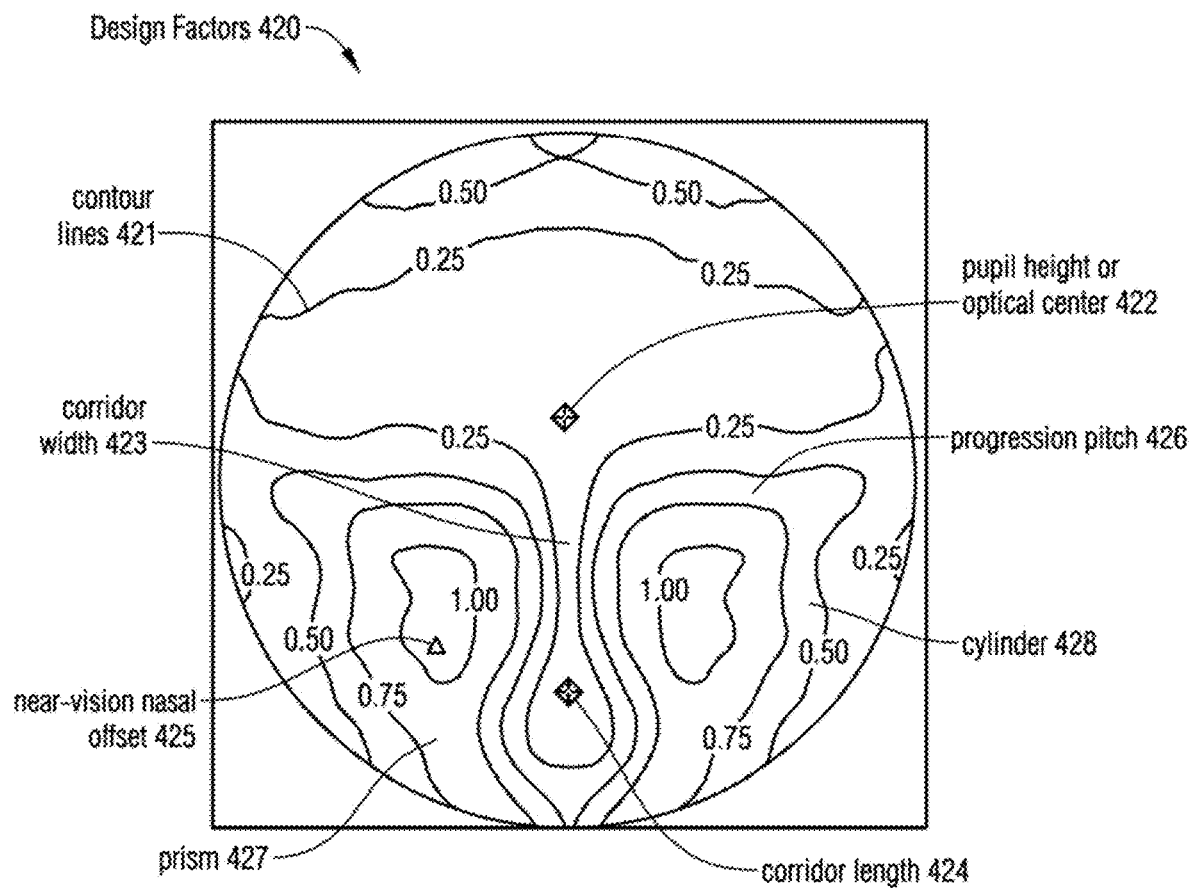
FIGS. 20A-B illustrate Design Factors.

FIGS. 20A-B illustrate Designs Factors 420. A large number of design factors can be used, and different lens manufacturers often have their own specialized set of Design Factors. By way of example, Designs Factors 420 may include contour lines 421, pupil height or optical center 422, corridor, or channel width 423, corridor length 424, near-vision nasal offset 425, progression pitch 426, prism, or prism angle 427, cylinder orientation 428, progressive prism, Zernike coefficients, and many-many others. With the ever-strengthening influence of the Schneider free-form lens manufacturing technology, any encoding of the lens topographic, contour or height map can be used as design factors.

Some design factors can be supplemented by preparatory measurements by the optometrist. One example is that the optometrist can observe the glass-positioning height, where the patient is wearing the glasses on her/his nose. The optometrist can shift the height of the optical center 422 Design Factor to account for the patient's individual glass-positioning height.

FIG. 20B illustrates that the collection of these individual design factors $DF_1, DF_2, \ldots, DF_k$ together can be thought of as defining a Design Factor Space. In this Design Factor Space, the specific progressive lens design can be represented with a Design Factor vector DF. The exploration of the progressive lens designs 123 can then be thought of as a guided wandering of the Design Factor vector DF through a series of iterations DF(1), DF(2), . . . , until the optimal Design Factor vector DF(final) is reached. (For clarity, the subscripts 1, 2, . . . k, refer to the individual Design Factors as components of the DF vector, whereas the indices 1, 2, . . . n in brackets refer to the number of iterative steps during the course of the iterative exploration of the progressive lens designs 123.)

Figures 20C, 20D:
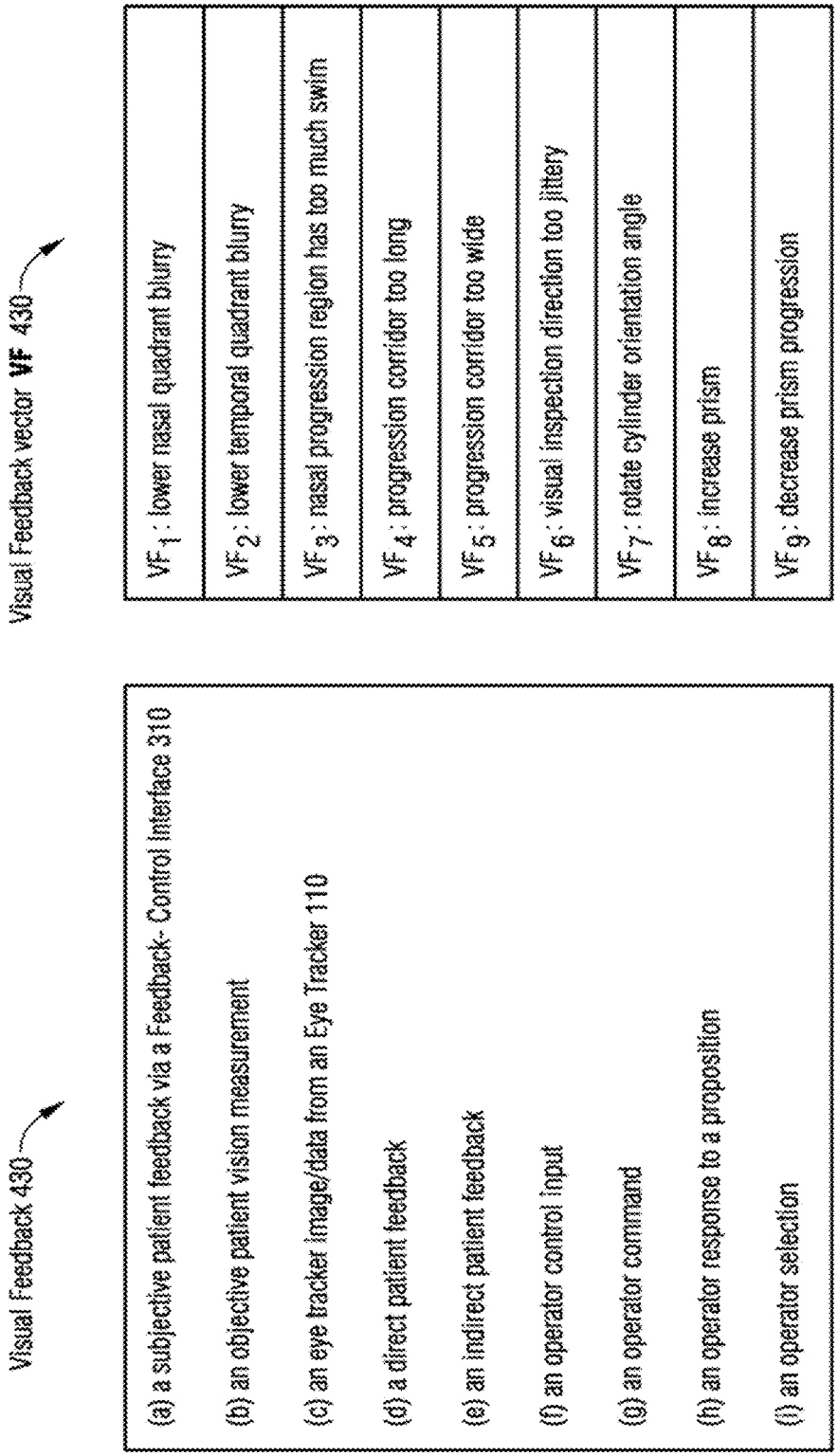
FIGS. 20C-D illustrate Visual Feedbacks.

FIGS. 20C-D illustrate the analogous organization of the Visual Feedback 430. These Visual Feedbacks 430 can be of different types or classes, including the followings.

(a) A subjective patient feedback via a Feedback-Control Interface;
(b) an objective patient vision measurement;
(c) an eye tracker image/data from an Eye Tracker;
(d) a direct patient feedback;
(e) an indirect patient feedback;
(f) an operator control input;
(g) an operator command;
(h) an operator response to a proposition; and
(i) an operator selection.

The term "Visual Feedback" is used broadly in this document. It can include subjective feedbacks, like the patient expressing a subjective evaluation of the visual experience. It can be an objective feedback, like a measurement of a jitteriness of the patient's visual axis. It can be a direct feedback directly entered by the patient into the FCI 310. It can be an indirect feedback, the patient verbally stating an experience or preference and an operator entering the corresponding feedback into the FCI 310. The feedback can come from a single operator, such as the patient, or from more than one operator, such as the patient entering a partial visual feedback and the operator entering another complementary feedback. Also, the Visual Feedback 430 can be simply a feedback, or a control, or command input, where the operator translated the visual experience into a control, command, selection, or response.

In each of the above classes, there can be a large number of specific Visual Feedbacks 430. To expand by examples, the subjective Visual Feedbacks can include the patient subjectively perceiving the lower nasal quadrant blurry, the lower temporal quadrant blurry, the nasal progression region has too much swim, progression corridor too long, progression corridor too wide. The subjective Visual Feedback 430 can include requests, commands, or other control input, such as the patient requesting rotate cylinder orientation angle, increase prism, and decrease prism progression. The objective Visual Feedback 430 can include the optometrist observing that the patient's visual inspection direction, or visual axis, being too jittery, or the patient having difficulty focusing on the presented object, and inputting a corresponding feedback-control input into the FCI 310. All of these possibilities are included in the scope of "Visual Feedback 430".

FIG. 20D illustrates that the individual Visual Feedbacks $VF_1, VF_2, \ldots, VF_l$ can be thought of as forming a Visual Feedback vector VF 430, in analogy to the Design Factor vector DF. In various embodiments, the length of the DF vector may not be equal to the length of the VF vector. In this approach, in each iteration of the progressive lens exploration by the method 400, a new Visual Feedback vector VF(n) is received from an operator, patient, or measurement system, such as the Eye tracker 110, and in response, the combined PLS 100–LDES 300 system modifies the Design Factor vector DF.

FIG. 16 shows that in several embodiments of the Lens Design Exploration System 300 for a Progressive Lens Simulator 100, the Progressive Lens Design Processor 320 includes a Visual Feedback-to-Lens Design Transfer Engine FLE 325, that plays an important role in modifying the progressive lens design 123 in response to the Visual Feedback 430.

An important role of this Visual Feedback-to-Lens Design Transfer Engine FLE 325 is to "translate" the received Visual Feedback 430 into a modification of the Design Factors 420. In an example, if the patient inputs the Visual Feedback 430 that "lower nasal region too blurry" into the Feedback Control Interface 310, it is a non-obvious task to translate this specific Visual Feedback 430 into which Design Factors to change to what degree to reduce the blurriness in the lower nasal region. A large amount of optical modelling, ray-tracing, patient-testing, and refinement are needed to establish that which set of Design Factors 420 need to be modified to what degree to respond to the various Visual Feedbacks 430. This complex knowledge is embodied, managed and carried out in the Visual Feedback-to-Lens Design Transfer Engine FLE 325.

Figure 21:
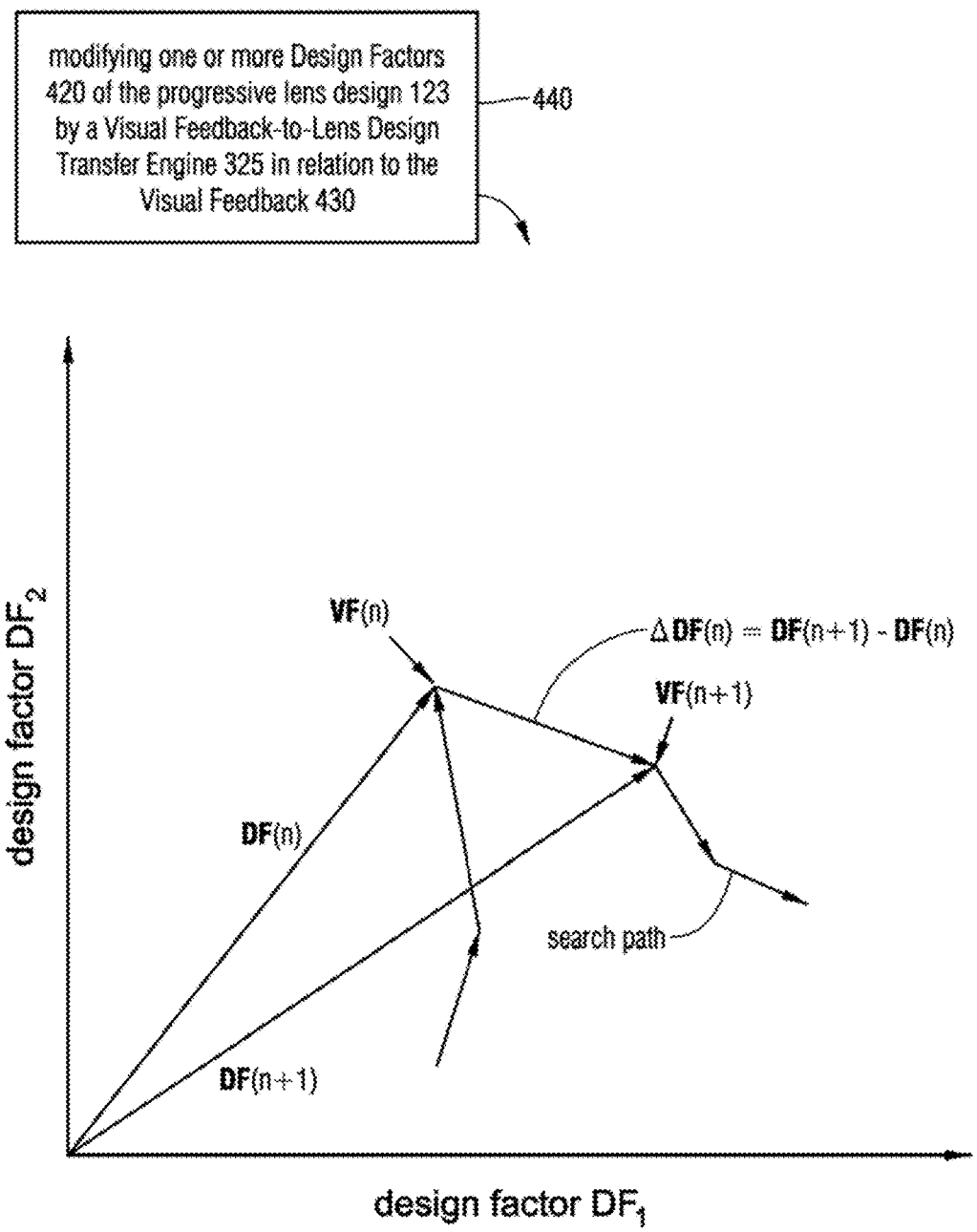
FIG. 21 illustrates a modifying of a Design Factor based on Visual Feedback in the Design Factor space.

FIG. 21 illustrates the usefulness of the above-introduced vector concepts to visualize the exploration of progressive lens designs. The Design Factors $DF_1, DF_2, \ldots, DF_n$ define a multi-dimensional Design Factor space. A specific progressive lens design 30 is represented by a specific Design Factor vector $DF=(DF_1, DF_2, \ldots, DF_k)$ in this space. The PLS 100 generates an initial Comprehensive PLS 30 for the patient, using a specific progressive lens design 123, now represented by a Design Factor vector DF(1). The PLS 100 then acquires a Visual Feedback vector $VF(1)=(VF_1, VF_2, \ldots, VF_l)$, responsive to the Comprehensive simulation of the Progressive Lens DF(1). The LDES 300 system modifies the Design Factor vector DF(1) into DF(2) in response to the Visual Feedback vector VF(1). FIG. 21 illustrates this process via the n-th iteration. The LDES 300 modifies the Design Factor vector DF(n) into DF(n+1) in response to the Visual Feedback vector VF(n) by adding:

$$\Delta DF(n) = DF(n+1) - DF(n) \quad (1)$$

Visibly, the ΔDF(n) increment vectors form a search path in the Design Factor space. As the combined PLS 100 and LDES 300 system performs the method 400, in interaction with an operator, patient, or optometrist according to the method 410, this search path converges to a customized optimal Design Factor vector DF 420 that best suits the patient's needs.

Figure 22A:
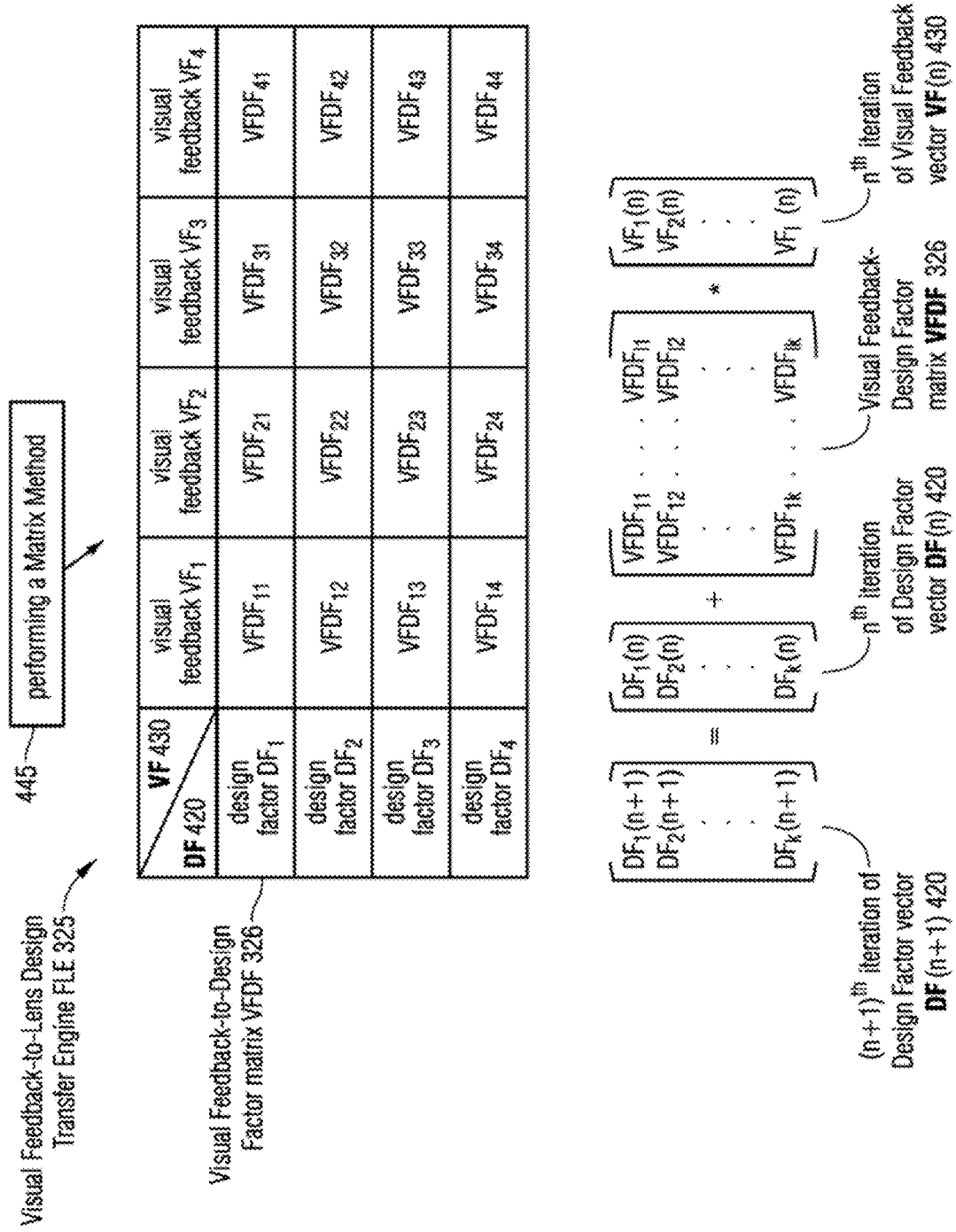

FIGS. 22A-B illustrate the case, when the relationship is approximately locally linear between the Visual Feedback vector VF 430 and the Design Factor vector DF 420. In such cases, the Visual Feedback-to-Lens Design Transfer Engine 325 can utilize a Visual Feedback-to-Design Factor matrix VFDF 326 for the modifying the progressive lens design by a Matrix Method. (Matrices and vectors are referenced with boldface.)

FIG. 22A illustrates a 4×4 representation of the VFDF matrix 326. The equation below is the extended form of the above Eq. (1). As discussed earlier, in general the length "k" of the DF vector 420 is not equal to the length "l" of the VF vector 430, so often the VFDF matrix 326 is a non-square, rectangular matrix.

The elements of the VFDF matrix 326 represent how to translate the elements of the Visual Feedback vector 430 into a change of the Design Factor vector 420. Typically, more than one element of the DF vector 420 need to be changed in a correlated manner. These correlations that translate the inputted Visual Feedback vector VF 430 into a design factor vector DF 420 constitute the elements of the VFDF matrix 326.

FIG. 22B illustrates this translation by an example. The VFDF matrix 326 is a 7×9 matrix in this embodiment. Visibly, the Visual Feedback vector VF 430 includes subjective patient feedbacks, like the patient indicating that the optical center too high, as well as objective feedbacks, like the Eye tracker 110 measuring that the visual inspection direction, or visual axis of the patient is too jittery. As an example, if the patient's Visual Feedback is "lower temporal quadrant blurry", that can be represented with a binary Visual Feedback vector 430 of VF=(0,1,0,0,0,0,0), or with a quantitative expression x, representing how blurry the image is VF=(0,x,0,0,0,0,0), e.g. determined by an observing optometrist. If the non-zero elements in the second column of the VFDF matrix 326 are $VFDF_{32}$ and $VFDF_{72}$, that means that the best response to the above Visual Feedback is to modify the Design Factor vector DF 420 with ΔDF=VFDF*VF=(0,0,$VFDF_{32}$,0,0,0,$VFDF_{72}$,0,0), i.e. to increase or decrease the progression corridor width by $VFDF_{32}$, depending on the sign of $VFDF_{32}$; and to rotate the cylinder clockwise or counter-clockwise $VFDF_{72}$, depending on the sign of $VFDF_{72}$. A wide variation of related and analogous embodiments exists, including the size of the VFDF matrix 326, and the choice of factors both in the DF vector 420 and the VF vector 430.

Figure 23A:
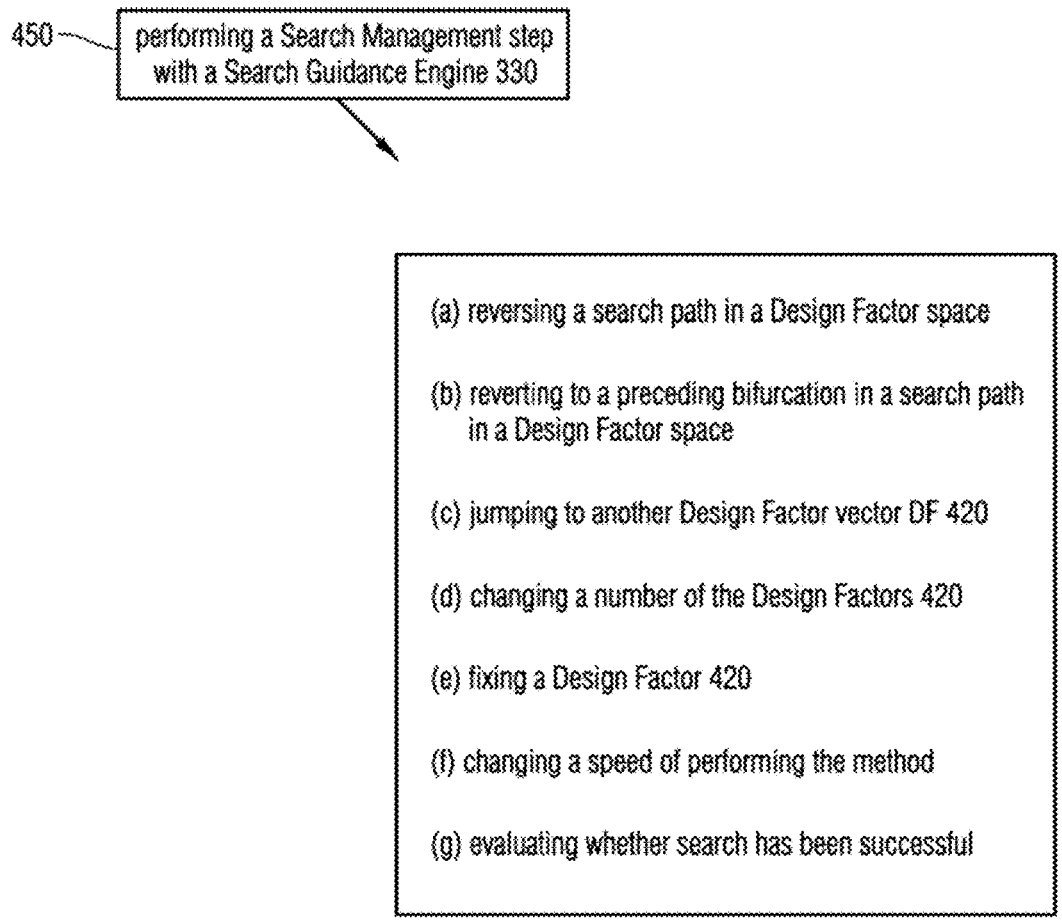
FIGS. 23A-B illustrate a Search Management method, with an interactive aspect.

FIG. 23A illustrates that in many instances, the exploration of the progressive lens designs 123 may require non-local and non-linear steps, which therefore are not well represented by a VFDF matrix 326. For example, the patient's exploration may end up in a region of the Design Factor space, where the patient keeps giving the Visual Feedback 430 that no change is improving the visual experience. In simple terms, that the search got stuck in a dead-end, and likely the optimal solution is in a far away, distinct region of the Design Factor space that cannot be easily reached. In such cases, the patient's search may be best assisted by a large jump to another region in the Design Factor space, or by some other robust move. In general, such moves will be referred to as performing Search Management steps 450. To facilitate such non-local and/or non-linear moves, the Lens Design Exploration System 300 can include a Search Guidance Engine SGE 330, coupled to the Progressive Lens Design Processor 320, for performing a Search Management step 450, including at least one of (a) reversing a search path in a Design Factor space;

(b) reverting to a preceding bifurcation in a search path in a Design Factor space;

(c) jumping to another Design Factor vector;

(d) changing a number of the Design Factors;

(e) fixing a design factor;

(f) changing a speed of performing the method; and (g) evaluating whether search has been successful.

Figure 23B:
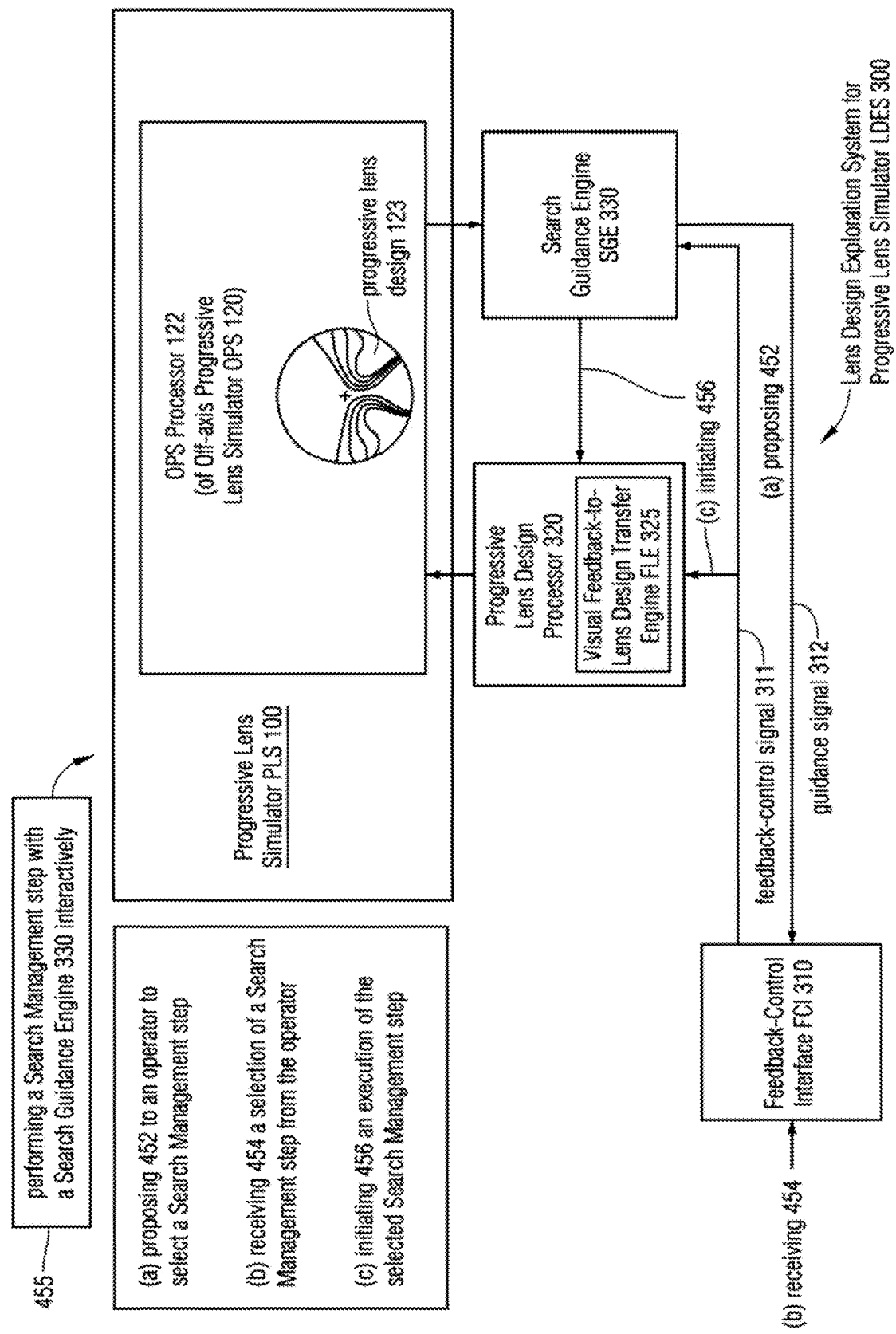

FIG. 23B illustrates that these Search Management steps 450 can be carried out in an interactive manner in some embodiments. In such embodiments, the Search Guidance Engine 330 may be coupled to the Feedback-Controller interface 310, for performing the Search Management step interactively 455 by (a) proposing to an operator to select a Search Management step 450;

(b) receiving a selection of a Search Management step 450 from the operator; and (c) initiating an execution of the selected Search Management step 450. The initiating 455(c) may involve the Search Guidance Engine 330 instructing the Progressive Lens Design Processor 320 to carry out the selected Search Management step 450.

In these embodiments, the Search Guidance Engine SGE 330 may not simply carry out a Search Management step 450 on its own directive, such as fixing a Design Factor. Instead, it may interactively propose a contemplated Search Management step 450 to the patient and act only upon receipt of a response. By way of an example, the SGE 300 may prompt the patient via the FCI 310: "Should we fix the location of the optical center, and restrict the search to the remaining Design Factors?" in the step 455(a), then receive the selection from an operator, e.g. "Yes" in step 455(b), and initiate carrying the selection, such as reduce the number of Design Factors by one, thereby reducing the dimensions of the Design Factor space by one in step 455(c). In some embodiments, the Search Guidance Engine 330 may offer alternatives: "should we go back to a preceding bifurcation in a search path in a Design Factor space, or should we reverse the search path?", and carry out the responsive wish of the patient or the operator.

In some embodiments, the Search Management method 455 can involve (d) the patient storing a selected first lens design 123;

(e) continuing the Lens Design Exploration by any embodiment of the method 400; for example, by reversing the search path by step 450(a), or reverting to a preceding bifurcation by step 450(b);

(f) selecting a subsequent second lens design 123; and (g) comparing the stored first lens design with the second lens design.

In some embodiments, the Search Guidance Engine SGE 330 may be integrated with the Progressive Lens Design Processor 320.

An aspect of the described embodiments that rely on subjective Visual Feedbacks 430 is that the exploration is not guided by objective merits and measures. In practice, this can, and does, reduce the repeatability of the exploration.

When the same patient repeats the same lens design exploration at a later time, it has been observed that she/he sometimes arrives at different lens designs: a potentially unsatisfying outcome.

Repeatability and the soundness of the lens selection can be enhanced by PLS 100 systems acquiring and prioritizing objective Visual Feedbacks 430. One such objective Visual Feedback 430 has been already described by the Eye tracker 110 measuring a jitter of the visual axis. Another class of objective Visual Feedbacks 430 can be generated by integrating diagnostic systems into the PLS 100. Such systems may include Purkinje-spot-based imaging systems, OCT systems, Scheimpflug imaging systems, wavefront analyzers, corneal topographers, slit lamps, and related other systems.

Another class of improvements can be introduced by using eye models to evaluate, organize and analyze the diagnostic measurements. Several eye models are known in ophthalmology, often used in preparation for cataract surgery, such as the Holladay and Hoffer models.

The next class of embodiments provides an improvement in this direction. These embodiments define a quantitative metric that can prove quite useful to make the lens design exploration more effective, and lead to repeatable outcomes.

FIGS. 24A-B introduce the concept of objective, quantitative measures and metrics to assist the exploration of the progressive lens designs 123. Such objective measures are already used by the designers of progressive lenses. However, presently these measures are used by computer programs separately from the patient's exploration, much after the patient visits the optometrist's office. Typically, the computer code performs the lens design search separated from the patient by hundreds, or thousands, of miles and hundreds, or thousands, of hours. In typical cases today, an optometrist determines a couple vision correction parameters in her office, for example, the optical powers for the near and distance vision regions, and then sends these parameters to a progressive lens designer. Weeks later, the progressive lens designer runs a computer code that computes a contour map that optimizes the lens performance with the sent optical powers. This optimization uses some quantitative measures to characterize the lens' performance, typically developed by the lens design company.

However, in today's practice, this optimization is not interactive; the patient is simply given the end product. There is no visual feedback from the patient during the design process, and no chance for the patient to indicate that the computer-designed progressive lens is far from optimal for the patient's specific needs. Thus, if the patient decides that the visual experience with the progressive lens is unsatisfactory, then he returns the lens and a time consuming, inefficient back-and-forth process starts between the lens designing company and the patient, typically shipping the glasses back-and-forth, and involving additional grinding of the lens, often taking many weeks, and wasting valuable time from all involved.

The here-described embodiments in general offer a substantive improvement over this state of the art by simulating a progressive lens design 123 in real time in steps 401-403, then acquiring a Visual Feedback 430 from the patient in real time in step 404, and modifying the progressive lens design 123 in real time in step 405, performing all these steps iteratively. The now-described embodiments offer a further improvement by introducing objective lens merit factors 460 and weave these lens merit factors 460 into the modifying the progressive lens design step 405 of the method 400.

These lens merit factors 460 can include:
(a) an improved visual acuity in one of a near and a far vision region;
(b) a reduced astigmatism in one of a near and a far vision region;
(c) a reduced swim in one of a near and a far vision region;
(d) a reduced blur in one of a near and a far vision region;
(e) a suitable progressive region;
(f) an alignment of a cylinder;
(g) a suitable prism; and
(h) a suitable progressive prism.

Many-many more Lens Merit factors can be developed, including more technical ones, such as the integral of a measure of an astigmatism over a vision region, or the coefficient of a Zernike polynomial of the lens, possibly narrowed to a region.

FIG. 24B shows that, as before, these Lens Merit Factor 460 can be thought of as a Lens Merit vector LM 460, with components $LM=(LM_1, LM_2, \ldots, L_m)$. In some cases, these individual Lens Merit factors can be combined into a single global Lens Merit with suitable weight factors. For example, this single combined Lens Metric can be $|LM|$, the overall length, or magnitude of the LM vector, combined from the sum of the squares of the individual components: $|LM|=[\Sigma_i LM_i^2]^{1/2}$. To simplify the notation in the below complex discussion, the labels 420, 430 and 460 are sometimes suppressed for the DF, VF and LM vectors.

Figure 25:
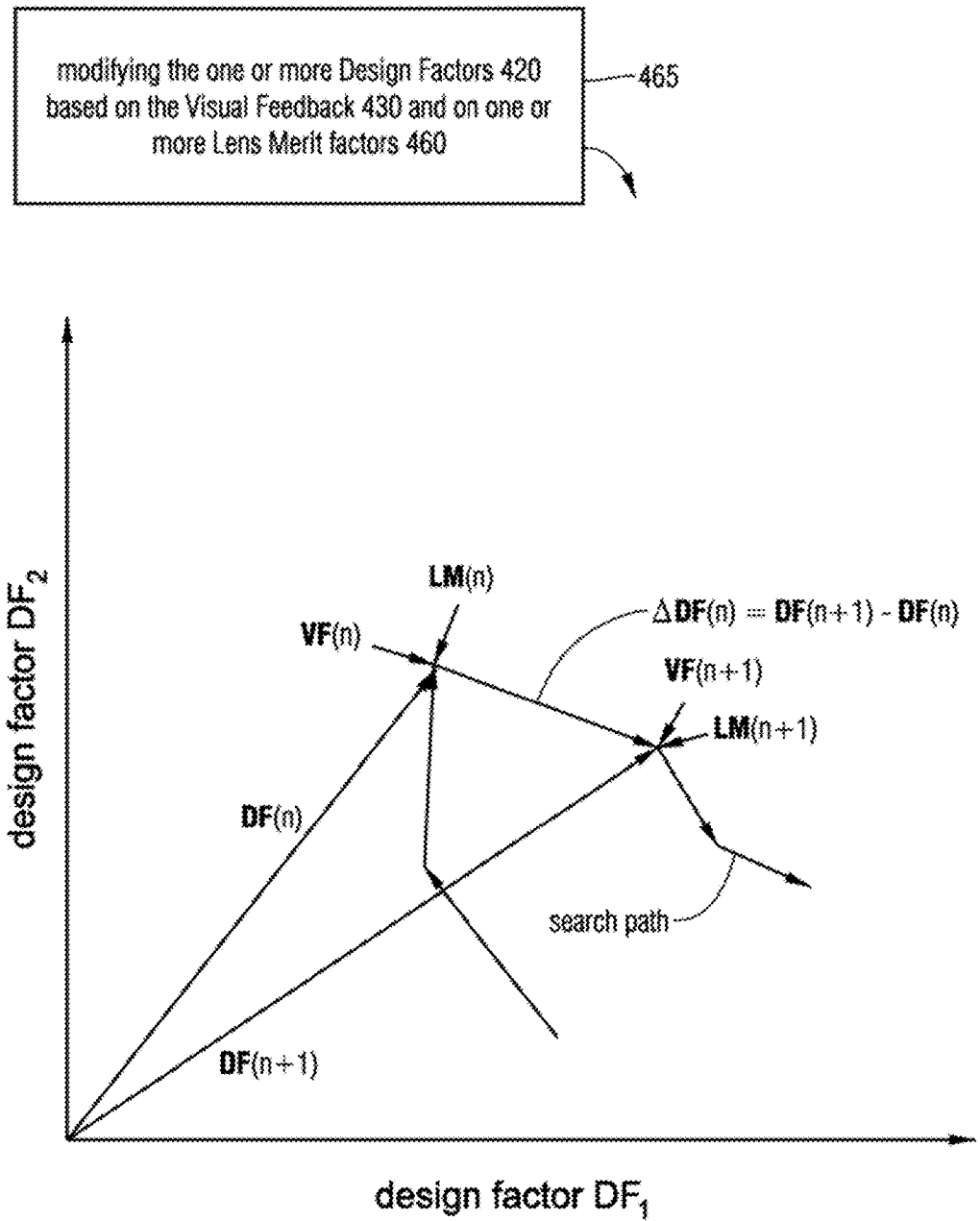
FIG. 25 illustrates a modifying of a Design Factor based on Visual Feedback and Lens Merit factors in the Design Factor space.

FIG. 25 illustrates the impact of introducing the Lens Merit factors into the progressive lens designs as a quantitative metric to assist the exploration of lens designs. In embodiments, the modifying step 440 can be expanded into the modifying the one or more Design Factors step 465, the modifying step 465 being based on the Visual Feedback 430 and on one or more Lens Merit factors 460. In the vector notation, the $n^{th}$ iteration of the Design Factor vector DF(n) gets modified by $\Delta DF(n)=DF(n+1)-DF(n)$, where $\Delta DF(n)$ is computed based on the Visual Feedback vector VF(n) 430 and the Lens Merit factor vector LM(n).

Figure 26:
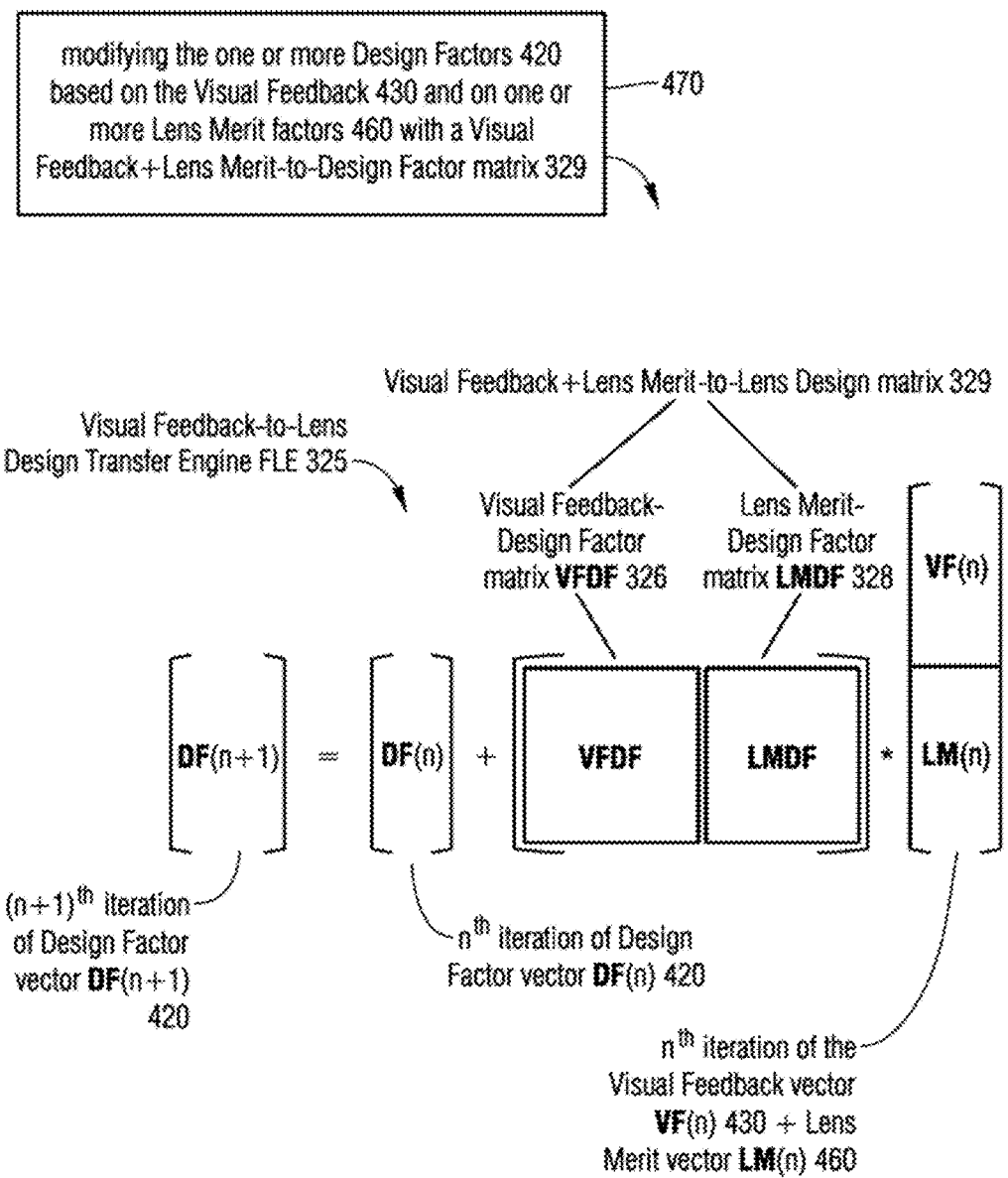
FIG. 26 illustrates a Visual Feedback+Lens Merit-to-Lens Design matrix of a Visual Feedback-to-Lens Design Transfer Engine.

FIG. 26 illustrates that when VF(n) and LM(n) determine $\Delta DF(n)$ approximately linearly, then the modifying step 465 can specifically involve a modifying step 470 that includes performing a Merit-Matrix Method step by modifying the one or more Design Factors DF(n) 420 in relation to the Visual Feedback VF(n) 430 and on one or more Lens Merit factors 460 with a Visual Feedback+Lens Merit-to-Design Factor matrix 329. As illustrated, this method 470 is driven not only by the Visual Feedback VF 430, but also by the objective Lens Merit LM 460. These two vectors VF and LM can be combined into a composite VF+LM vector whose length equals the length of the two vectors separately. Next, the VFDF matrix 326 can be extended by a Lens Merit-Design Factor matrix LMDF 328, the juxtaposition of the two matrices together forming the Visual Feedback+Lens Merit-to-Design Factor matrix 329. Multiplying the extended VF+LM vector with the extended VFDF+LMDF matrix determines $\Delta DF(n)$ in these embodiments.

Figure 27:
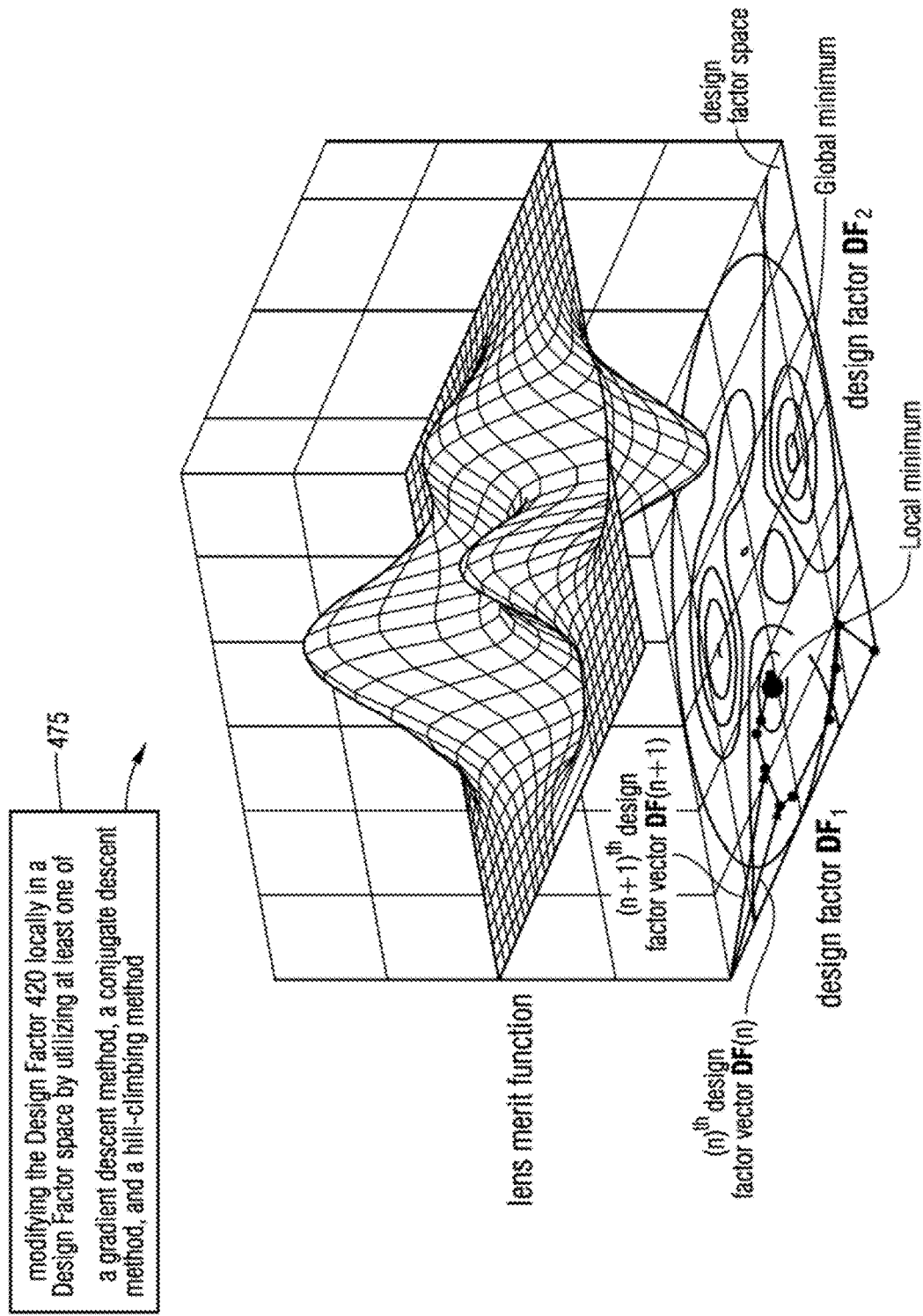
FIG. 27 illustrates a method for modifying the Design Factor locally.

FIG. 27 illustrates some of the benefits of such Lens Merit-computing embodiments. For a specific progressive lens design 123, represented by a Design Factor vector DF, the components of the Lens Merit vector LM can be calculated. FIG. 27 shows only one component of the LM vector. In certain cases, this can be the global Lens Merit $|LM|$, mentioned earlier. In other embodiments, the method 475 described below can be practiced for several of the Lens Merit components simultaneously. By way of example, the shown component of the LM vector, $LM_j$, can be the integrated astigmatism over the near vision region. The lower $LM_j$, the integrated astigmatism, the better the progressive lens design 123. In the context of FIG. 27, this means that the optimal progressive lens design 123 corresponds to the DF=(DF$_1$, DF$_2$) vector 420 that points to the extremum of the Lens Merit function. For a multicomponent Lens Merit vector LM, the individual Lens Merit factors LM$_i$ can be minimized in a coupled, interconnected manner. The issue of the Lens Merit function having more than one extrema (as illustrated in FIG. 27) will be addressed below.

In some existing systems, where the progressive lens design 123 is determined by a lens design code without a Visual Feedback 430, the lens design code optimizes the lens design only by modifying the Design Factors DF$_1$ and DF$_2$ so that the Design Factor vector DF points to the location of the local minimum of the Lens Merit function, shown in FIG. 27. Such local minima indicate that the corresponding combination of the Design Factors DF$_1$ and DF$_2$ optimizes the visual experience according to ray tracing, optical measurements and large number of collected patient experiences, but without a feedback of the specific patient whose progressive lens is being designed. Such optima reflect a compromise between the different design goals.

The methods 465, 470 and 475 transcend previously described systems by modifying the one or more Design Factors 420 based on the Visual Feedback 430 in combination with one or more Lens Merit factors 460. Therefore, the methods 465/470/475 transcend the method 440 that primarily relies on the Visual Feedbacks 430 but does not use the Lens Merit 460. These methods also transcend the present progressive lens design codes that rely only on computing Lens Merit 460, but do not use the Visual Feedback 430. Combining the two design-drivers VF 430 and LM 460 is challenging, for several reasons. First, to be able to combine these design-drivers requires the Visual Feedbacks 430 to be quantified, but the quantification of the various subjective Visual Feedbacks 430 is far from obvious. Second, a lot of thoughtful decisions are needed to select the weight factors that combine the VF and LM factors and components. Further, communicating the contemplated lens design updates to the patient in a relatable manner is also a non-trivial task, among others.

Typically, the patient's Visual Feedback VF 430 may request, or prompt, a modification of the Design Factor vector DF 420 that is different from the DF 420 pointing to the local minimum of LM. This can happen for a variety of reasons including the following. (a) The local minimum of LM in the lens design code was determined by averaging feedback from a large number of patients, and thus may not be optimal for any specific patient. (b) The search may involve optimizing several LM components simultaneously. Compromising between these coupled searches can make a DF 420 optimal for a vector other than the minimum for the coupled search. (c) The exploration uses a combination of the VF 430 and the LM vectors 460 to modify the DF vector 420. The subjective VF 430 inputs may nudge the exploration towards new design goal compromises. Also, in some embodiments, the patient may be offered to shift the mixing and weighing parameters, again moving the local minimum.

In some embodiments, the modifying step 475 may include modifying the Design Factors locally in a Design Factor space by utilizing at least one of a gradient descent method, a conjugate descent method, and a hill-climbing method. In FIG. 27, this can be implemented at any DF(n) vector by, e.g., searching out the locally steepest downhill gradient that promises to move the exploration towards the local minimum in the fastest manner. Since these methods build on local information about how the LM$_i$ components depend on their DF$_j$ coordinates, the method 475 is characterized as a local modification.

However, FIG. 27 also illustrates that such local methods may not reach the global minimum of the Lens Merit function LM 460, if the global minimum is at some distance away from the local minimum in the Design Factor space. In this typical case, the local steepest descent gradient methods often guide the search only into the local minimum, where the methods may get stuck and never reach the global minimum, located a distance apart.

Figure 28A:
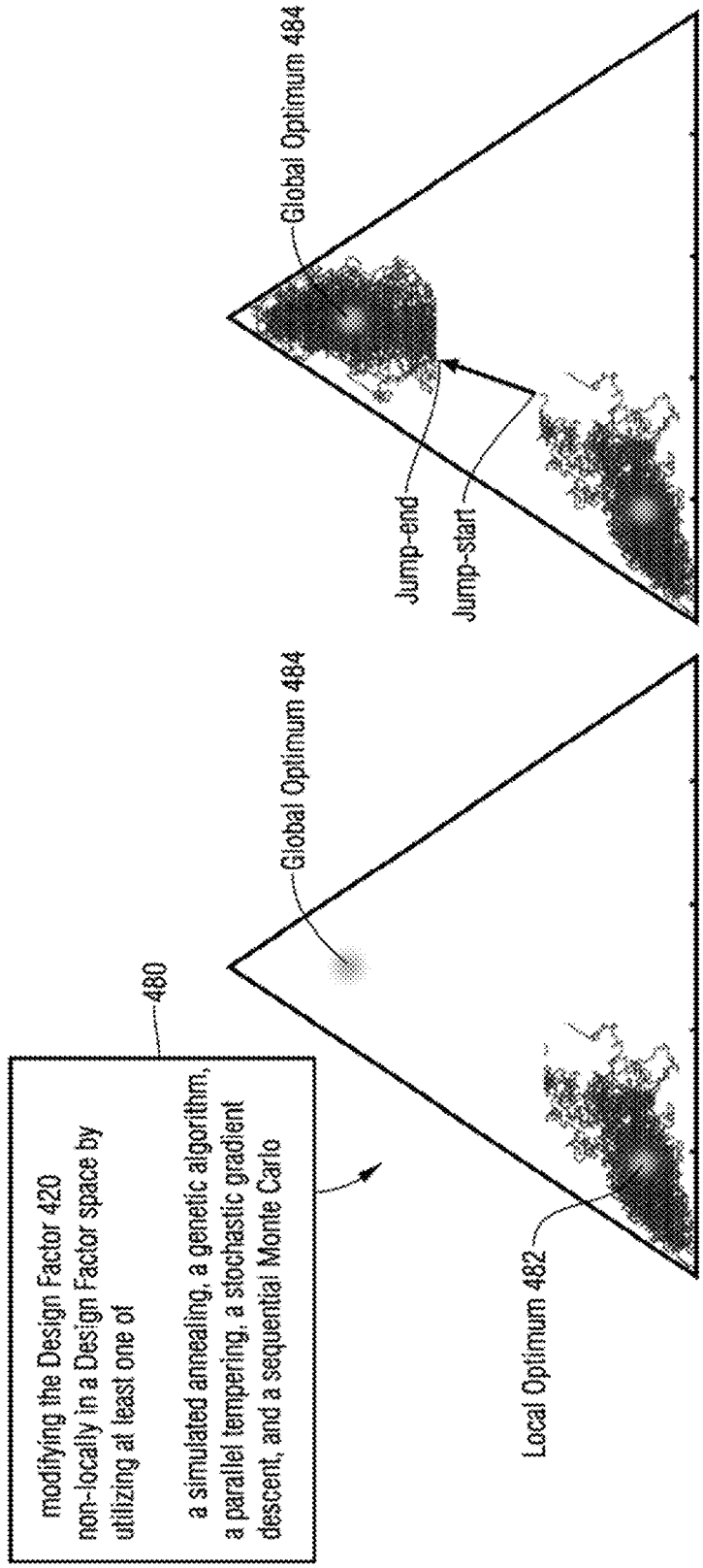
FIGS. 28A-B illustrate a method for modifying the Design Factor non-locally.
Figure 28B:
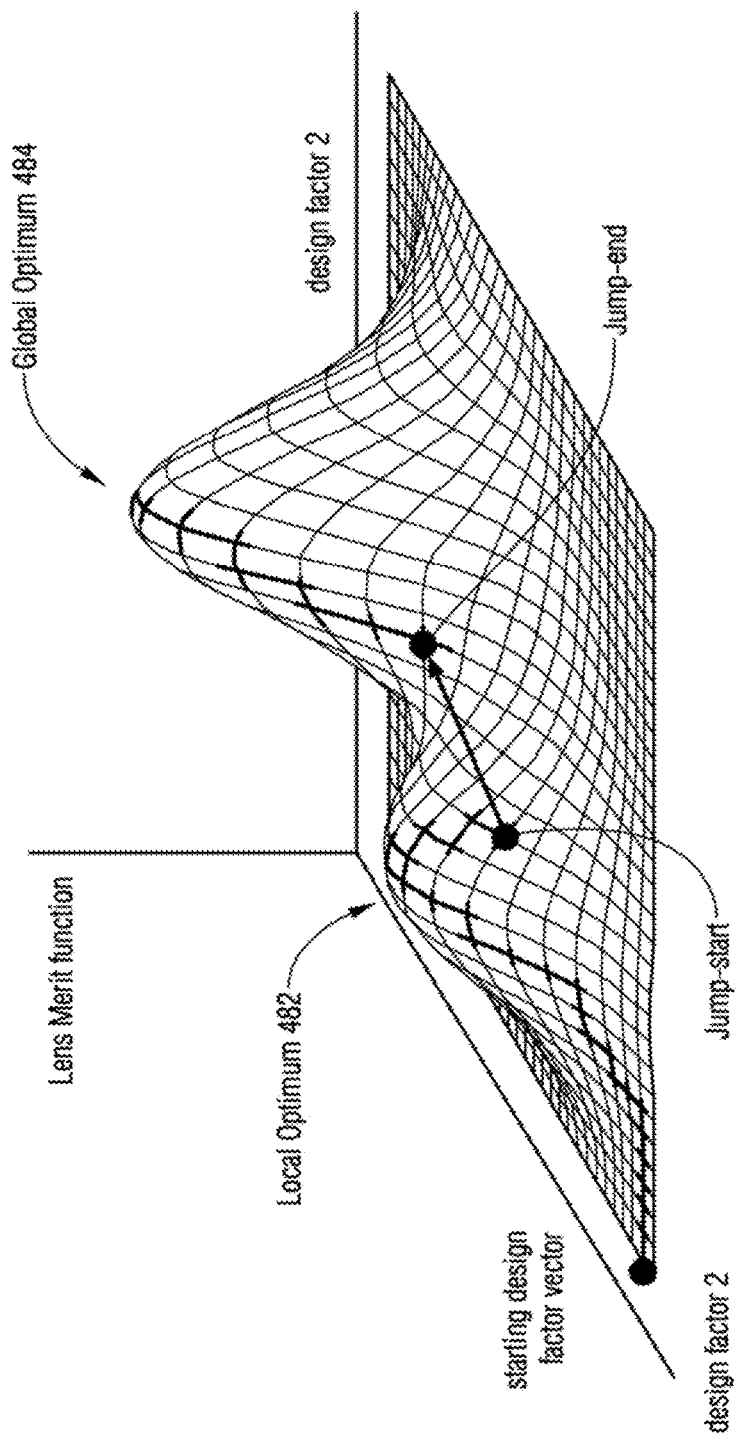

FIGS. 28A-B illustrate that in such cases a modifying 480 of the one or more Design Factors 420 based on the Visual Feedback 430 and on one or more Lens Merit factors 460 may include modifying 480 the Design Factor 420 non-locally in the Design Factor space. This non-local modification 480 may utilize at least one of a simulated annealing, a genetic algorithm, a parallel tempering, a stochastic gradient descent, stochastic jumps, and a sequential Monte Carlo.

In the shown example, the lens design exploration may be getting temporarily stuck around a Local Optimum 482 when only local search methods 475 are utilized. It is noted that the optimum can be either a minimum or a maximum. In FIG. 27, the desired design corresponded to a minimum of the LM function, in FIGS. 28A-B, it corresponds to a maximum. The local modification methods 475 can get stuck in the Local Optimum 482 that is distinctly away from the Global Optimum 484. Embodiments of the method 480 can free the stuck search by employing the above listed non-local methods. A large number of additional non-local modifications are also known in the arts. One such method is to implement large, stochastic jumps, to get a stuck search "unstuck". FIG. 28A illustrates that a search that uses only local techniques may have gotten stuck around the Local Optimum 482, but performing a stochastic jump embodiment of the non-local method 480 can get the search unstuck, and enable it to find the Global Optimum 484. FIG. 28B illustrates the same stochastic jump embodiment of the method 480 from a perspective view. Visibly, the stochastic jump is taking the stuck search from the jump-start to the well-separated jump-end point in the Design Factor space, enabling it to reach the Global Optimum 484.

Figure 29A:
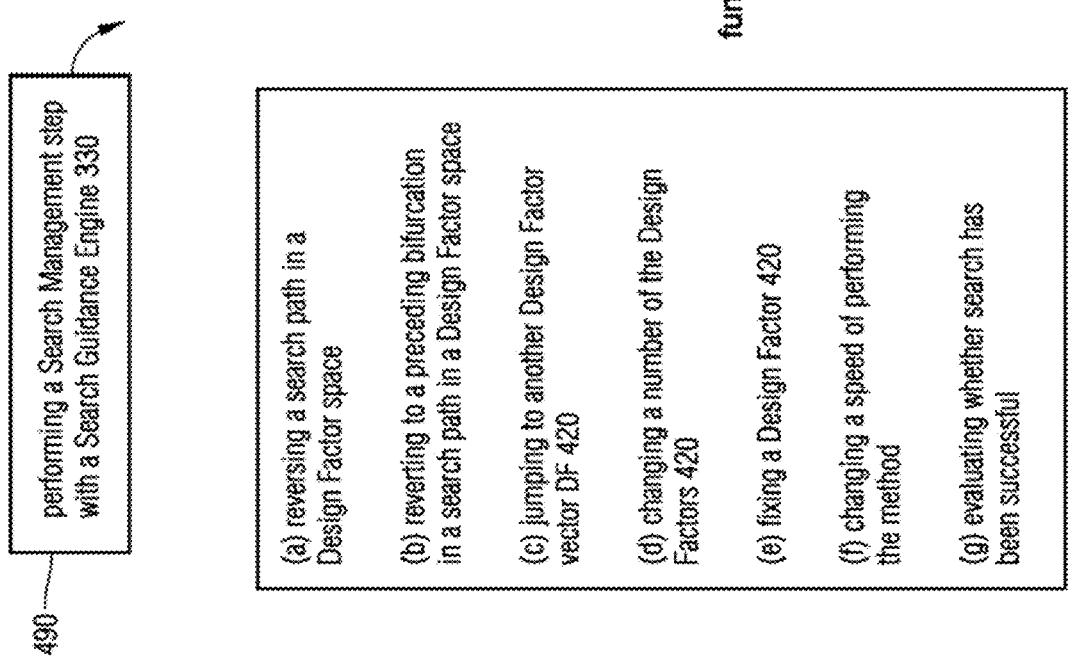
FIGS. 29A-B illustrate performing a Search Management step, in some cases interactively.

FIG. 29A illustrates that—in analogy to method 450 in FIG. 23A—any one of the 465-480 embodiments of the modifying the one or more Design Factors step based on the Visual Feedback 430 in combination with on one or more Lens Merit factors 460 can comprise a Search Management step 490, performed by the Search Guidance Engine 330, that can include at least one of the followings.

(a) Reversing a search path in a Design Factor space;

(b) reverting to a preceding bifurcation in a search path in a Design Factor space;

(c) jumping to another Design Factor vector;

(d) changing a number of the Design Factors;

(e) fixing a Design Factor;

(f) changing a speed of performing the method; and (g) evaluating whether search has been successful.

As discussed in relation to the analogous method 450, such Search Management methods, or steps 490 can be very helpful when the patient's exploration of lens designs becomes disoriented, or stuck. In other embodiments, their primary value can be that they accelerate the progressive lens design exploration, making it much more efficient. In this method 490 the added factor relative to the method 450 is that a quantitative metric is involved in the form of the Lens Merit 460. The introduction of such a quantitative metric greatly narrows down the search. For example, the large number of possible ways of modifying the Design Factors 420 that need to be evaluated when practicing the methods 440 and 450 can be reduced substantially by narrowing the search to paths that the Lens Merit 460 identifies as locally optimal. In the example of FIG. 29A this is demonstrated by a non-merit guided searches 440-455 needing to evaluate all possible Design Factor modifications, whereas the Lens Merit factor guided searches 465-490 needing to evaluate only moves along the narrow ridge, preferred by the Lens Merit 460, or in some vicinity of this ridge.

As before, FIG. 29A shows the search path on the ridge for only one LM component for clarity. As the Search Guidance Engine 330 is monitoring the search and senses that the ridge is getting lower (as shown), i.e. the search by the local modifying method 475 is getting farther from possibly finding a local maximum of the Lens Merit 460, the Search Guidance Engine 330 may activate the method 490(a) and perform a Search Management step to reverse the search path. Here the availability of the quantitative metric of the Lens Merit 460 is quite useful, as the reverse search path in the Design Factor space is a well-defined ridge of the Lens Merit function 460. The availability of a well-defined reverse path can greatly increase the efficiency of the exploration and search.

FIG. 29A also illustrates an embodiment of the method 490(b), reverting to a preceding bifurcation in a search path in the Design Factor space. During the search, or exploration, at some points two choices may appear comparably meritorious. In such instances, the patient, or the Progressive Lens Design Processor 320, needs to choose one of the possibilities. FIG. 29A illustrates such a case, when the search path encountered the locally optimal ridge splitting, or bifurcating, into two, comparable ridges. The search method 465, possibly with its local embodiment 475, chose the left branch and pursued the exploration for a while. However, after monitoring the exploration on the left ridge for a while, the SGE 330 decided that is was time to practice the method 490(a) and reversed the search. Advantageously, the quantitative Lens Merit function 460 provided clear guidance how to pursue the reversed path: by retracing the ridge of the LM 460. Retracing the ridge leads the search back to the bifurcation, where previously the search selected the left ridge. At this junction, the Search Guidance Engine 330 now may choose the right ridge instead and then re-engage the local modifying method 475 to guide the search along the other ridge. Throughout these steps of the methods 475 and 490, the quantitative Lens Merit function 460 provided clear guidance and greatly narrowed the searches to be pursued (from exploring surfaces to exploring ridges), thereby enhancing the efficiency and speed of the overall exploration.

Figure 29B:
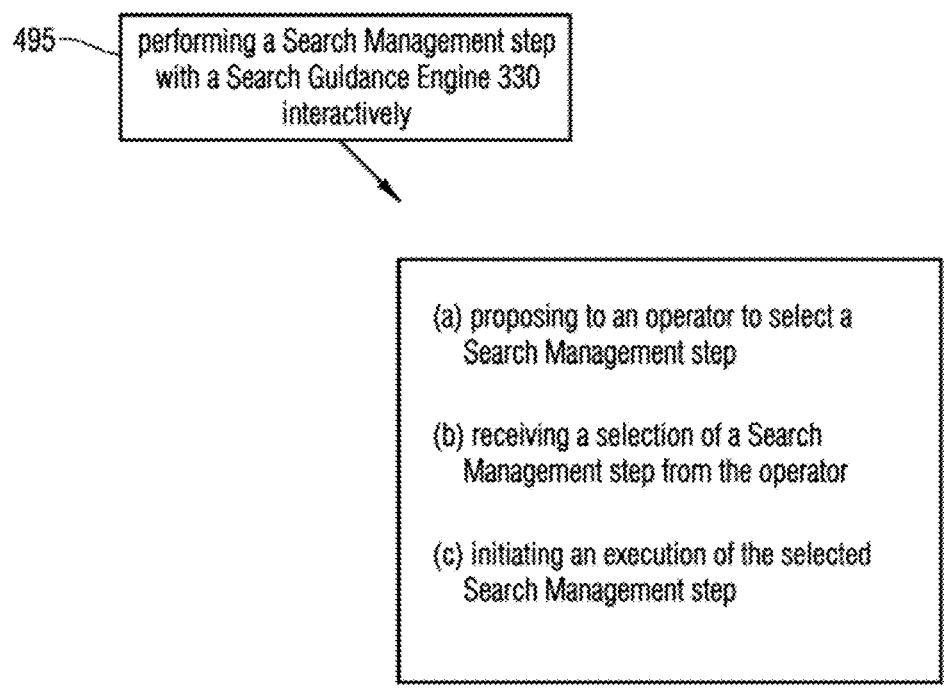

FIG. 29B illustrates that in some embodiments, the method 490 can be expanded to include method 495 that includes performing the Search Management step with a Search Guidance Engine 330 interactively by (a) proposing to an operator to select a Search Management step;

(b) receiving a selection of a Search Management step from the operator; and (c) initiating the execution of the selected Search Management step.

As with the interactive method 455 earlier, the method 490 can also be improved by performing it interactively. Instead of the Progressive Lens Design Processor 320 and the Search Guidance Engine 330 of the LDES 300 making choices by some algorithm, the method 495 prompts the patient, or operator, to provide Visual Feedback 420, command or control signal, and to select a Search Management step, thereby accelerating the lens design exploration via executing steps 495(a)-(b)-(c).

In some further embodiments, the modifying the progressive lens design can include modifying the progressive lens design by the Progressive Lens Design Processor 320 utilizing non-linear Visual Feedback-to-Design Factor functional relations, or non-linear Visual Feedback+Merit-to-Design Factor functional relations. These embodiments can be alternatives and complementary of the Matrix methods 445 and 470, where these relations are dominantly linear.

Some embodiments of the PLS 100+LDES 300 system and the method 400 of its operation can include additional elements and steps that make it essentially certain that the overall method 400 will not deliver inferior results for the patient relative to traditional practices. These additional steps can include determining a second, "traditional" progressive lens design that is based on traditional measurements that do not involve simulating the second progressive lens design for the patient and asking for his/her Visual Feedback. This can be followed by generating a Comprehensive PLS 30 with this second, traditional progressive lens design. In such embodiments, the patient gets to experience the progressive lens design the traditional approach delivers, as well as the lens design identified by method 400 with the help of PLS 100+LDES 300. Generating the two differently designed progressive lenses, one with simulation and feedback, the other with traditional measurements, the patient can compare the Comprehensive PLS of these two designs, and select his/her preference. With this extension of the method 400, the patient cannot end up with a lens worse than the traditional progressive lens, as he/she can elect the traditional progressive lens anytime, even at the very end of the office visit, if he/she is unsatisfied with the lens design determined by the method 400.

In some cases, the generating 402 an image 21 by an Image Generator 121 can be in response to an image selection. This additional step can again improve patient satisfaction, as the patients can select images that are relevant for their activities, instead of the well-known rows of letters which do not capture life-like applications. For example, a team sports person may need extra emphasis on peripheral vision, and thus can select an image 21 that has notable features located peripherally. A long-distance truck driver may select moving images, as she/he may prioritize optimizing her/his vision for moving images. A night guard may select images with low light conditions, as she/he may need to optimize his vision for low light circumstances. Offering to test a patient's vision on use-relevant images can further improve the customization and thereby the satisfactory outcome of the method 400.

7. Deep Learning Method for a Progressive Lens Simulator with an Artificial Intelligence Engine Translating the Visual Feedbacks 430 into the Design Factors 420 most effectively is a substantial challenge. The various methods 400-495 offer promising embodiments. To make these embodiments the most efficient, their many parameters need to be optimized. These include the elements of the Visual Feedback-to-Design Factor matrix 326 and the elements of the Visual Feedback+Lens Merit-to-Lens Design matrix 329. For other embodiments, the possibly non-linear connections between the Visual Feedbacks 430 and the Design Factors 420 need to be tabulated and parameterized. Also, the Search Guidance Engines 330 are best operated on the basis of past experiences. The Search Management methods 450/455 and 490/495 can also be improved by learning from the lessons of the preceding explorations. Finally, performing the local modification steps 475 and non-local modification steps 480 can be done most efficiently by utilizing the lessons of past searches.

Recently, entirely new ways of learning from past experiences have been automated in remarkably effective new ways. In various technical treatises, these ways are called Artificial Intelligence, Deep Learning, Machine Learning, or Neural Networks. Other names are also used to capture roughly the same learning methods. The embodiments in this section integrate Artificial Intelligence-based learning methods and systems into the GPS 10 so as to improve and optimize the many parameters of the matrices 326 and 329, the operations of the SGE 330 and the methods of 450/455 and 490/495, as well as the other areas where learning from past experiences is beneficial.

Figure 30:
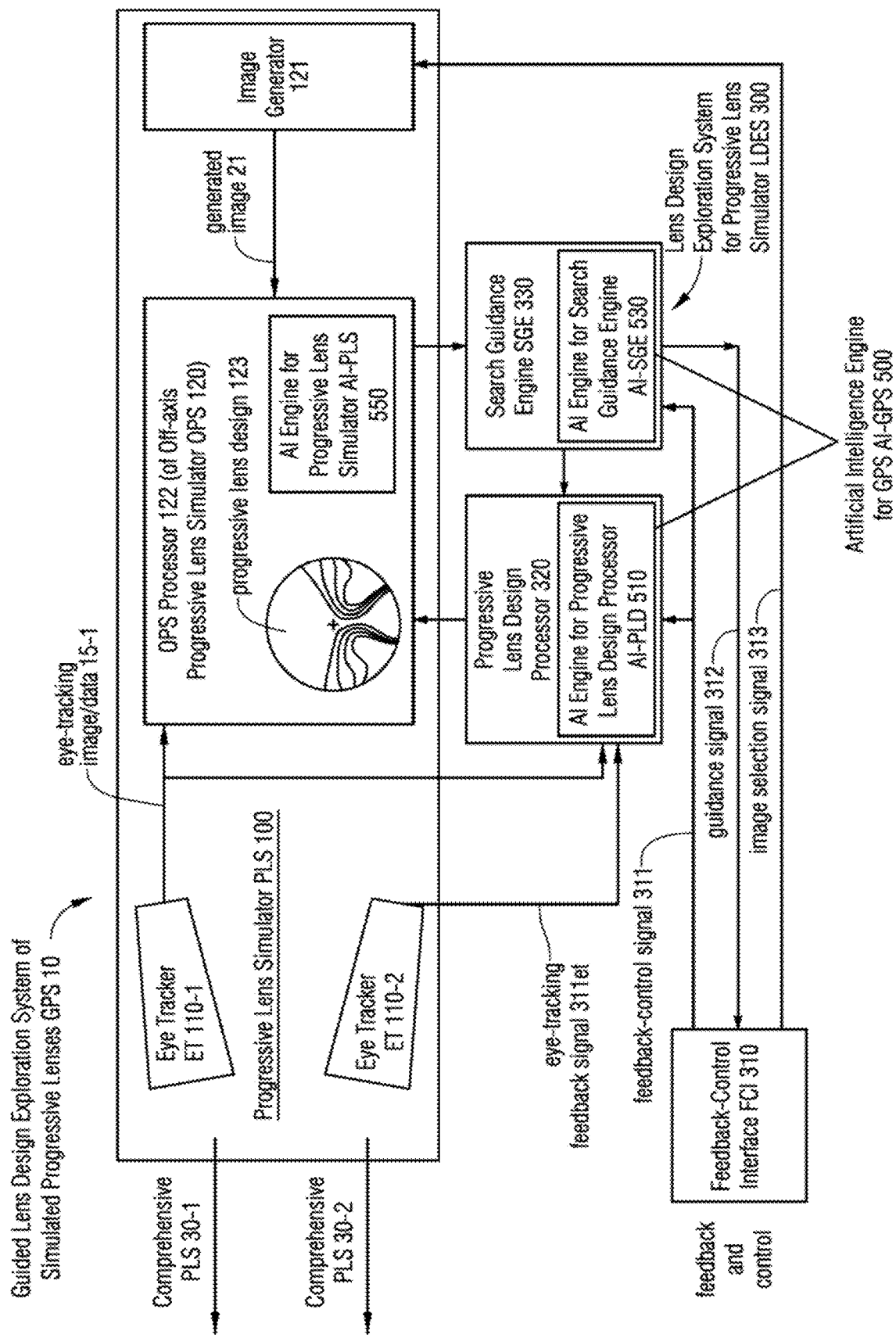
FIG. 30 illustrates a Progressive Lens Simulator with a Guided Lens Design Exploration System and with Artificial Intelligence Engines.

FIG. 30 illustrates such a Guided Lens Design Exploration System of Simulated Progressive Lenses (GPS) 10. This GPS 10 can include any embodiment of the Multistage PLS 100, Integrated PLS 200, or head-mounted PLS 260. FIG. 30 illustrates these possibilities via the multistage PLS 100 embodiment as an example. The PLS 100 can be combined with any, previously described embodiment of the Lens Design Exploration System for the PLS LDES 300. The combination of the PLS 100 and the LDES 300 can be integrated with an Artificial Intelligence (AI) Engine for the GPS (AI-GPS) 500. In this section, the GPS 10 will reference the combination of any embodiment of the PLS 100 with the LDES 300 and the AI-GPS 500.

The AI-GPS 500 can include an AI Engine for the Progressive Lens Design Processor (AI-PLD) 510, integrated into, or at least coupled to the Progressive Lens Design Processor 320. The AI-PLD 510 can carry out most of the functions of the Visual Feedback-to-Lens Design Transfer Engine FLE 325, and thus can be viewed as an embodiment of the FLE 325. A function of the AI-PLD 510 can be to perform any one of the many known Deep Learning methods in order to make translating the Visual Feedbacks 430 into modifications of the Design Factors 420 more efficient. As indicated, these Deep Learning methods can repeatedly update and improve the matrix elements of the Visual Feedback-to-Design Factor matrix 326, and the matrix elements of the Visual Feedback+Lens Merit-to-Lens Design matrix 329.

In some embodiments, the GPS 10 can also include an AI Engine for the Search Guidance Engine (AI-SGE) 530, integrated into, or at least coupled to the Search Guidance Engine SGE 330. A function of the AI-SGE 530 can be to perform any one of the many known Deep Learning methods with the SGE 330 in order to make it more efficient in guiding the exploration of the progressive lens designs 123 by any of the described methods. These methods include method step 450: performing a Search Management step with the SGE 330; method step 455: performing the method step 450 interactively with a patient; performing the method step 490: performing a Search Management step 330 with the SGE 330 that involves a Lens Merit 460; and method step 495—performing the method step 490 interactively with a patient, among others.

Finally, the AI-GPS 500 can also include an AI Engine for the Progressive Lens Simulator (AI-PLS) 550, integrated into, or at least coupled to PLS 100, in some case integrated into its OPS processor 122. Embodiments of the AI-PLS 550 can perform any of the known AI Deep Learning methods with the OPS Processor 122 to simulate the progressive lens designs 123 better, learning from the Visual Feedbacks 430 of the patients.

Figure 31:
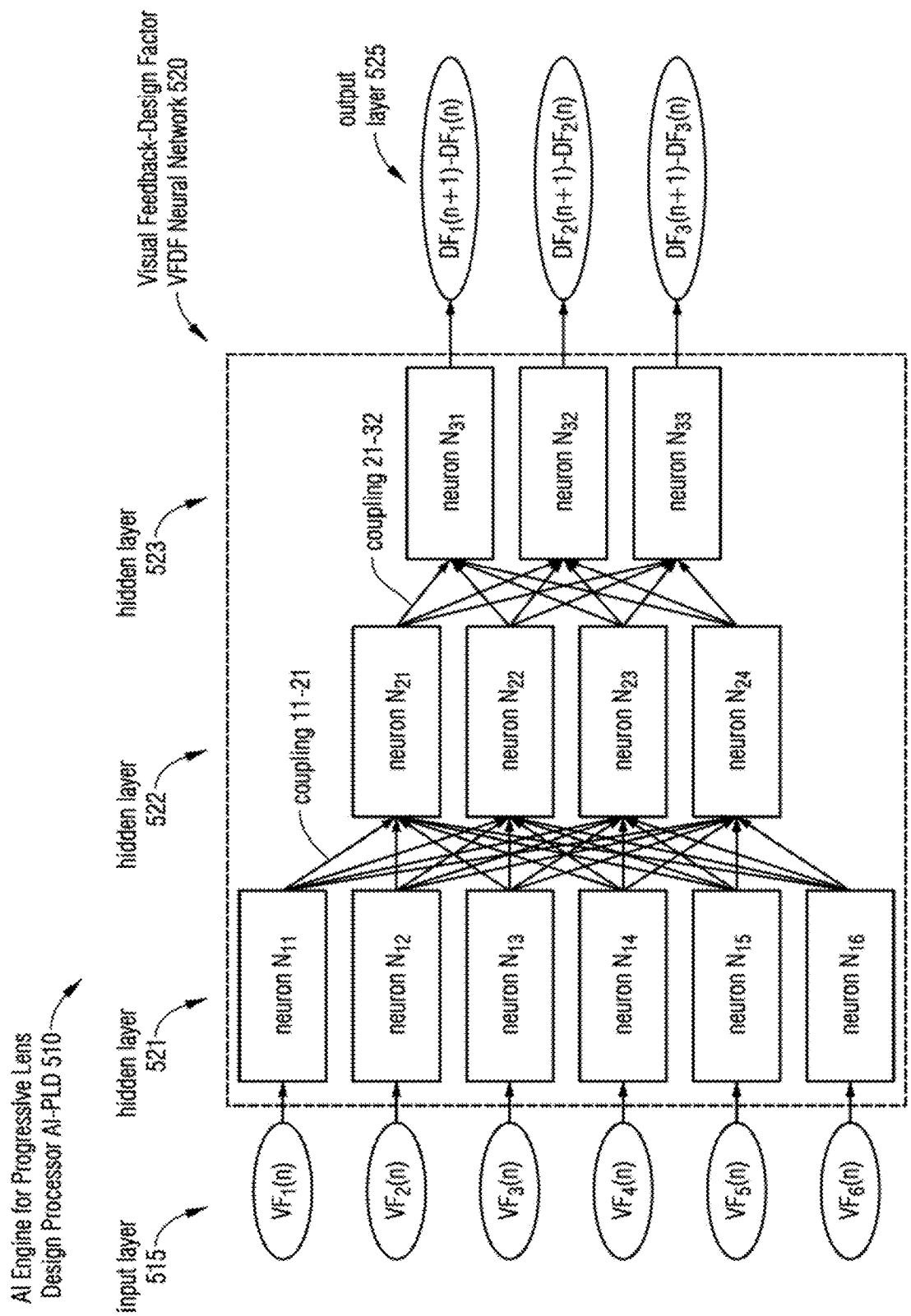
FIG. 31 illustrates a Visual Feedback-Design Factor Neural Network.
Figure 32:
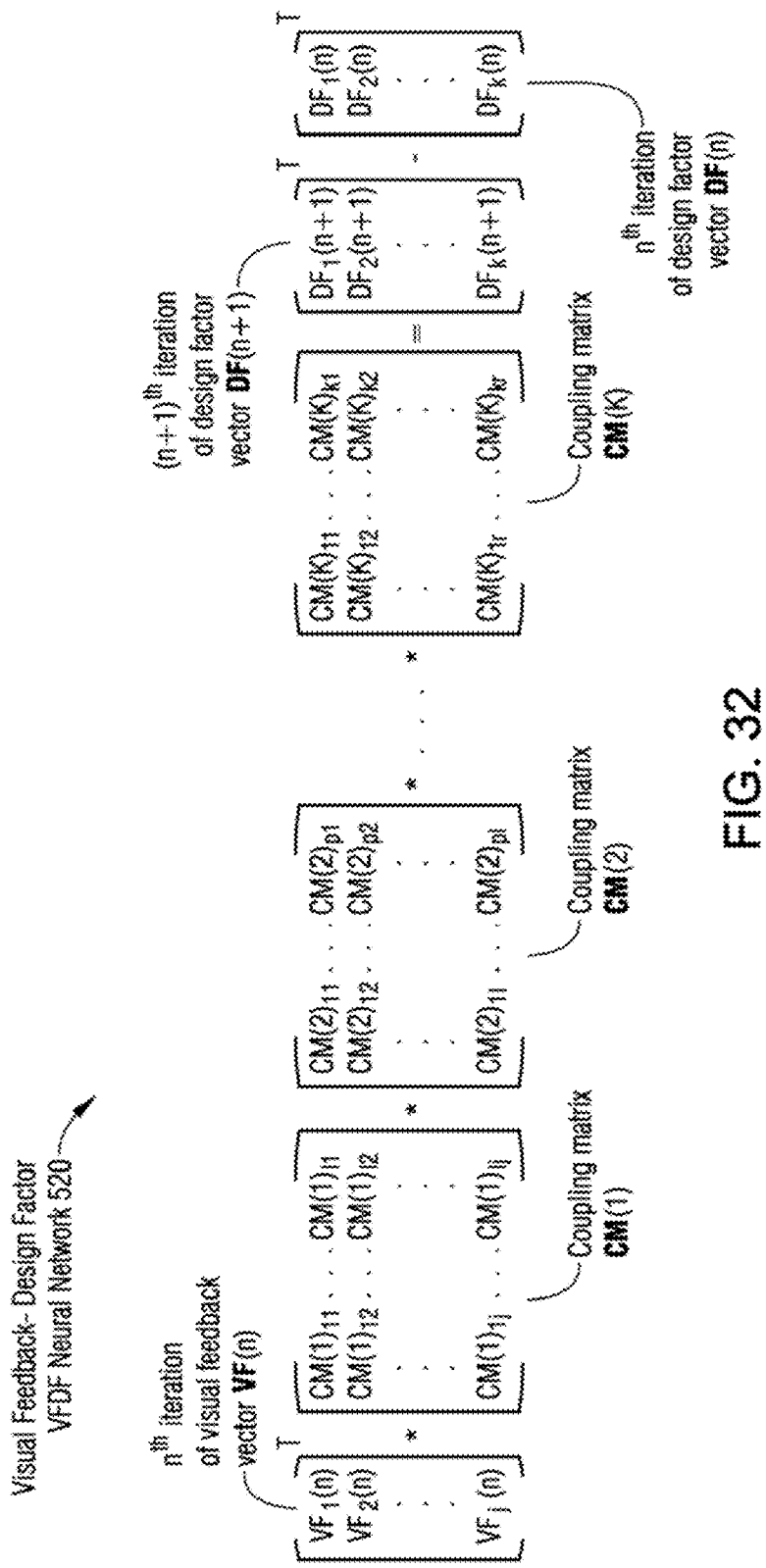
FIG. 32 illustrates an Artificial Intelligence Engine for Progressive Lens Design Processor.
Figure 33:
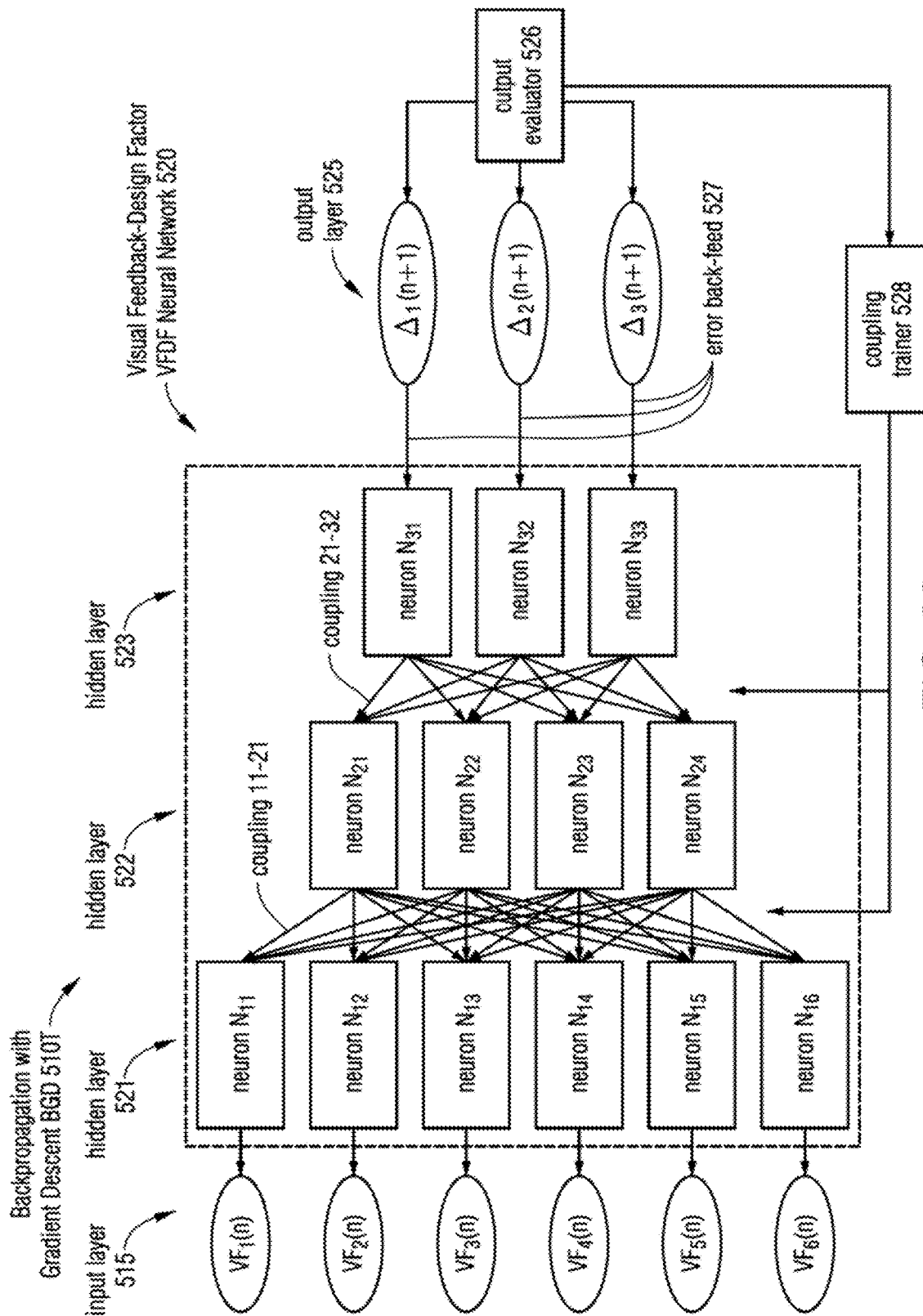
FIG. 33 illustrates a Backpropagation with Gradient Descent.

FIGS. 31-33 illustrate an embodiment of the AI-PLD 510. The AI-SGE 530 and the AI-PLS 550 can have closely analogous designs and will not be expressly described to avoid triplication.

The AI-PLD 510 can include an input layer 515, configured to receive the Visual Feedbacks $VF_i(n)$ as inputs. (In what follows, the label 430 will not always be expressly shown for the Visual Feedbacks 430, and the label 420 for the Design Factors 420, in order to avoid clutter). The patient, the operator or an objective feedback generating system, such as the Eye tracker 110, or any other eye imaging system can input the $VF_i$ elements of the Visual Feedback vector VF(n). As before, "n" references the $n^{th}$ iteration of the lens design exploration method 400. A Visual Feedback-Design Factor VFDF Neural Network 520 can receive the $VF_i(n)$ Visual Feedbacks as inputs. This VFDF Neural Network 520 can be configured to output a proposed update of the Design Factor vector $\Delta DF(n)=DF(n+1)-DF(n)$ at an output layer 525. In this sense, the VFDF Neural Network 520 plays an analogous function as the Visual Feedback-to-Lens Design Factor Engine FLE 325.

One of the differences is that the input VF vector 430 is not connected to the output DF vector 420 by a linear VFDF matrix 326. Instead, it is generated by a series of transformations, performed by a series of hidden layers 521, 522, 523, as shown. Each hidden layer can include a set of neurons. In the shown example, the first hidden layer 521 includes neurons $N_{11}, N_{12}, \ldots, N_{16}$. In this description, the specific number of hidden layers, and the number of neurons in each layer is for illustrational purposes only. Other embodiments may contain any other number of hidden layers and neurons per layer.

The neurons $N_{1i}$ in the first layer can be coupled to the neurons of the second layer $N_{2j}$, with coupling strength $C(1i-2j)$.

FIG. 32 illustrates the operation of the VFDF Neural Network 520. The effect of the Visual Feedback vector elements $VF_i$ getting processed by the neurons of a hidden layer is to multiply the VF vector with a Coupling Matrix CM. Here the notation is used that the (ij) element of the CM(m) matrix is the coupling constant between the neuron $N_{mi}$ and $N_{(m+1)j}$. With this notation, the above referenced coupling constant $C(1i-2j)$ is $CM(1)_{ij}$, the (ij) element of the CM(1) matrix. Thus, the output of a VFDF Neural Network 520 with K hidden layers can be written as:

$$VF(n)^T * CM(1) * CM(2) * \ldots * CM(K) = \Delta DF(n)^T, \quad (2)$$

where the superscripts T in $VF(n)^T$ and $\Delta DF(n)^T$ indicate vector transposition. This is needed, as in FIG. 22A the vectors were multiplied with the matrices from the left, while in FIG. 32 from the right, to represent the left-to-right layer-to-layer processing of the Visual Factor vector VF 430 in FIG. 31. Obviously, these two descriptions are equivalent.

In words, the output vector $\Delta DF$ 420 is related to the input vector VF 430 not by a single linear relation, as in the case of the VFDF matrix 326, but by a product of several bilinear relations. It is noted that the dimensions of the individual coupling matrices can vary in this product, or chain, of coupling matrices. Selecting these dimensions wisely can enhance the efficiency of the lens design exploration. For example, there are AI methods that advocate initially shrinking the dimensions of the CM(i) matrices, then increasing them back up, forming a sort of tunnel, or spool.

The neurons in each layer can be set up to react to their input in a variety of ways. A simple, widely used algorithm is a sharp threshold input-output relation output=$f$(input). The inputs from the preceding layer i to a particular neuron $N_{(i+1)l}$ in the $(i+1)^{th}$ layer can be added up, and if this sum exceeds a threshold T, then the neuron $N_{(i+1)l}$ outputs a value, whereas if the sum does not exceed the threshold T, then the output remains a different, lower number, typically zero. In formula, $$N_{(i+1)l} = f(\Sigma_j N_{ij} CM(i)_{jl} - T), \quad (3)$$

where $f(x)$ is a sharp switching function of its argument x, typically a step function centered at 0, or a somewhat smoothed step function such a tan h(x). A motivation for this switching function $f(x)$ emerged from the operations of neurons: the inputs from several dendrites that bring in the inputs in the form of stimuli are often added up by the electric charging processes of the neuron. As carried out by the ion pumps across the cell membrane. If the sum of these stimuli, often in the form of a total charge, exceeds a threshold, then the output axon of the neuron fires. If the charging does not reach the threshold, the neuron does not produce an output.

One way to set up such a VFDF Neural Network 520 is Google's TensorFlow machine learning framework. This is a convenient sophisticated framework that can be set up with limited preparation. A designer of the VFDF Neural Network 520 can simply enter the number of hidden layers, the number of neurons in each layer, and the switching functions $f(x)$. Then, the initial coupling constants of the VFDF Neural Network 520 can be entered or defined.

After this initialization, the VFDF Neural Network 520 is driven through many teaching, or learning cycles so that the VFDF Neural Network 520 learns from incorrect, or low fidelity results, and the initial coupling constants "learn" and evolve to reduce the incorrect outputs and produce the correct output in a high percentage of the cases.

FIG. 33 illustrates one such teaching, or learning approach, called Back-propagation with Gradient Descent (BGD) 510T. In such a supervised learning method, a Visual Feedback vector VF 430 is inputted where the supervisor knows what output is expected. As an example, if the Visual Feedback 430 is that the image is blurry in the lower nasal quadrant after the refractive power has been increased in this quadrant in the few preceding cycles, then the expected output ΔDF is to keep increasing the refractive power in this quadrant. With this known expectation, this VF is inputted into the input layer 515 and then processed with the VFDF Neural Network 520, resulting in an output at the output layer 525. An output evaluator 526 then can compare the output with the targeted output and send the difference signals $\Delta_i(n+1)$ back through the same VFDF Neural Network 520 as an error-back-feed 527. In the given example, whether the VFDF Neural Network 520 outputted a "Increase the refractive power further in the lower nasal quadrant" ΔDF(n) modification of the Design Factor vector DF 420, and what power increase was outputted specifically. As the difference signal is propagating backwards, a coupling trainer 528 can modify the individual couplings $CM(i)_{kl}$ to reduce the difference. Performing these training cycles a large number of times with a large number of inputted visual feedback vectors VF 430 trains the elements of the Coupling Matrices CM(1), CM(2), . . . , CM(K) so that after the training, when new Visual Feedbacks VFs are inputted for which the outputs are not known, the VFDF Neural Network 520 will still output the most appropriate ΔDF with high reliability.

Training the AI Engine AI-GPS 500 with this Back-propagation with Gradient Descent (BGD) 510T is just one of the many possible methods to train this VFDF Neural Network 520. Also, using this particular Neural Network implementation of the AI-GPS 500 is just one of the many embodiments of the basic idea to utilize Artificial Intelligence systems and methods to improve the GPS 10. All these combinations and alternatives share the following two basic design principles, and can be viewed as embodiments of the GPS 10 system, as long as they do so. These design principles include the followings.

(1) To fine tune the large number of parameters needed to operate the GPS 10 system, such as the elements of the VFDF matrix 326 or the Visual Feedback+Lens Merit-to-Design Factor matrix 329, utilizing the remarkable power of Artificial Intelligence in any suitable AI-GPS engine 500.

(2) To continue developing and improving these GPS 10 systems as a rapidly increasing number of GPS 10s are installed worldwide. It is envisioned that a centralized system may collect the exponentially increasing amount of data on the many-many lens design explorations performed worldwide daily by a rapidly increasing number of patients. This exponentially increasing "big data" can be analyzed by central AI-GPS engines 500. The results of this analysis can be pushed out from the central system to the individual GPS 10 systems in the form of updates for the on-board search software, including the training of the elements of the matrices 326 and 329, the training of the various steps that can be involved in the Search Management 450/455 and 490/495, and the training of the simulation of the progressive lens designs 123 by the PLS 100s. Any embodiment that shares these two basic drivers is an embodiment of the GPS 10.

Figure 34:
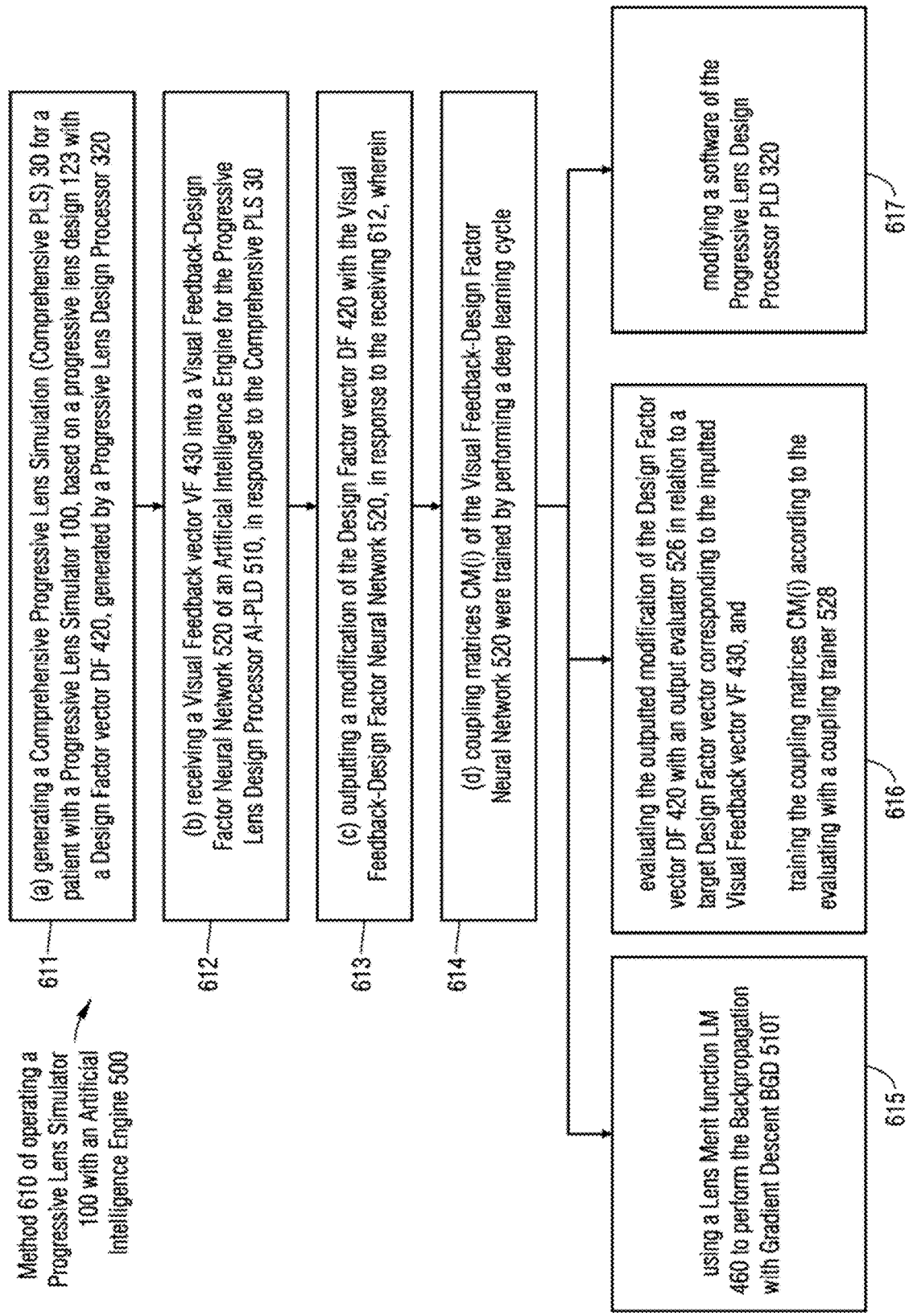
FIG. 34 illustrates a Deep Learning method for an AI Engine for a Progressive Lens Design Processor.
Figure 35:
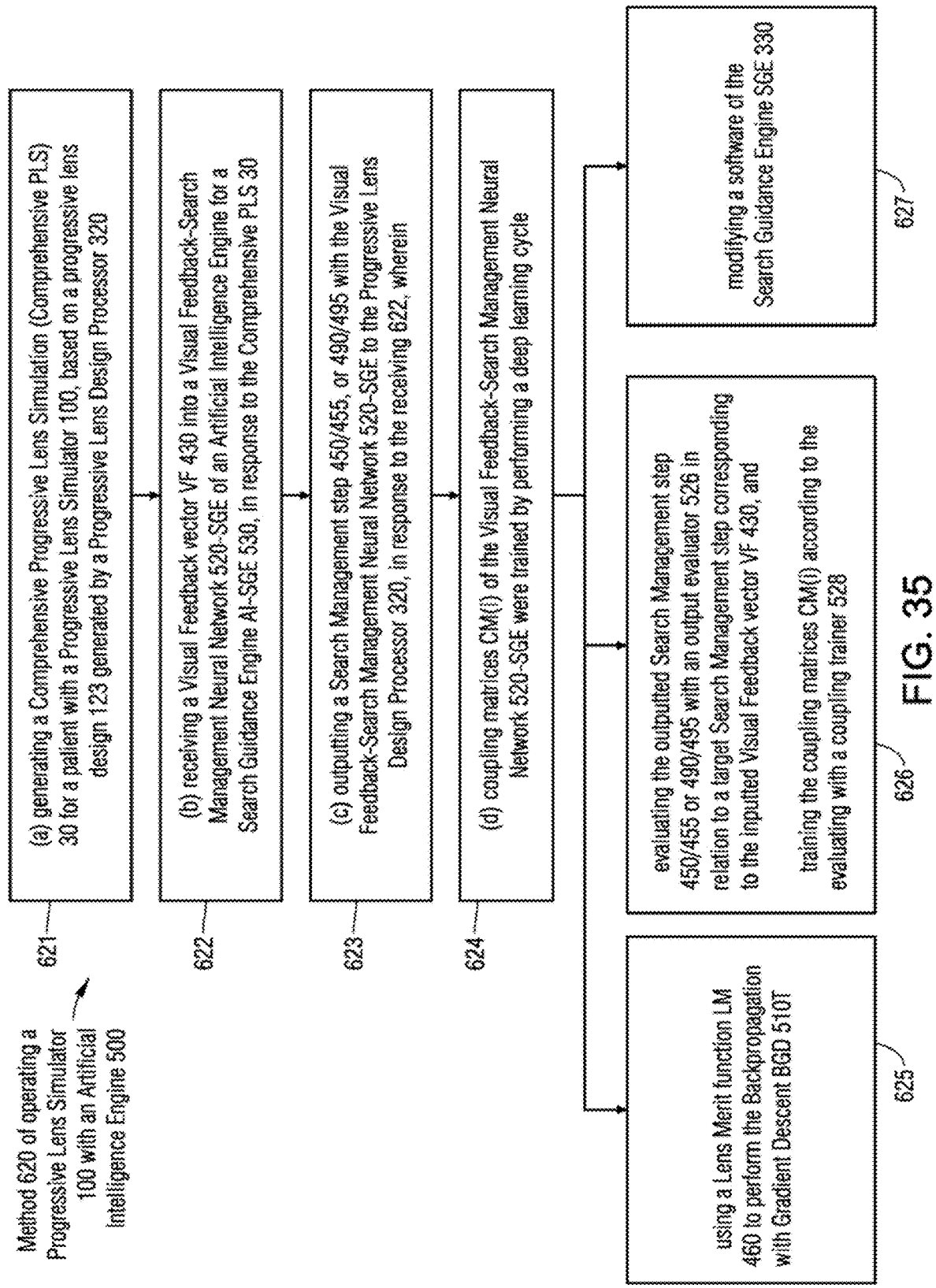
FIG. 35 illustrates a Deep Learning method for an AI Engine for a Search Guidance Engine.

FIGS. 34-35 illustrate methods of operation of the AI-GPS engines 510 and 530. FIG. 34 illustrates a Method 610 of operating a Progressive Lens Simulator 100 with an Artificial Intelligence Engine 500, comprising:

(a) generating 611 a Comprehensive Progressive Lens Simulation (Comprehensive PLS) 30 for a patient with a Progressive Lens Simulator 100, based on a progressive lens design 123 with a Design Factor vector DF 420, generated by a Progressive Lens Design Processor 320;

(b) receiving 612 a Visual Feedback vector VF 430 into a Visual Feedback-Design Factor Neural Network 520 of an Artificial Intelligence Engine for the Progressive Lens Design Processor AI-PLD 510, in response to the Comprehensive PLS 30; and (c) outputting 613 a modification ΔDF of the Design Factor vector DF 420 with the Visual Feedback-Design Factor Neural Network 520, in response to the receiving 612; wherein (d) coupling matrices CM(i) of the Visual Feedback-Design Factor Neural Network 520 were trained by performing 614 a deep learning cycle.

The method 610, further comprising:

(e) modifying the progressive lens design 123 by the Progressive Lens Design Processor 320 using the modified Design Factor vector DF 420; and (f) generating a modified Comprehensive PLS 30 by the Progressive Lens Simulator 100, using the modified progressive lens design 123.

Repeating steps (b)-(f) iteratively can serve as the backbone of the exploration of the progressive lens designs, as described in relation to method 400.

The Visual Feedback-Design Factor Neural Network 520 can include layers of neurons $N_{ij}$, including an input layer 515, one or more hidden layers 521/522/523, and an output layer 525. The neurons $N_{ij}$ can having switching functions $f(x)$, and the neurons $N_{ij}$ can be coupled by the coupling matrices CM(i).

The performing a learning cycle step 614 may include performing the deep learning cycle by Backpropagation with Gradient Descent (BGD) 510T. Performing the deep learning cycle step with BGD 510T can fine tune the elements of the Coupling matrices $CM(i)_{kl}$ to provide the most reliable translation of the Visual Feedbacks 430 into changes of the Design Factor vector 420.

The performing a learning cycle step 614 may also include using 615 a Lens Merit function LM 460. Using a Lens Merit function LM 460 can enable the AI-GPS engine 500 and specifically the AI-PLD 510 to train and improve the Lens Merit based methods 465-495.

The performing a deep learning cycle 614 can also include evaluating 616 the outputted Design Factor vector DF 420 with an output evaluator 526 in relation to a target Design Factor vector DF 420 corresponding to the inputted Visual Feedback vector VF 430; and training the coupling matrices CM(i) according to the evaluating with a coupling trainer 528.

In some embodiments, the performing a deep learning cycle step 614 can include modifying 617 a software of the Progressive Lens Design Processor 320.

FIG. 35 illustrates a Method 620 of operating a Progressive Lens Simulator 100 with an Artificial Intelligence Engine 500, comprising:

(a) generating 621 a Comprehensive Progressive Lens Simulation (Comprehensive PLS) 30 for a patient with a Progressive Lens Simulator 100, based on a progressive lens design 123 generated by a Progressive Lens Design Processor 320;

(b) receiving 622 a Visual Feedback vector VF 430 into a Visual Feedback-Search Management Neural Network 520-SGE of an Artificial Intelligence Engine for a Search Guidance Engine AI-SGE 530, in response to the Comprehensive PLS 30; and (c) outputting 623 a Search Management step 450/455, or 490/495, with the Visual Feedback-Search Management Neural Network 520-SGE to the Progressive Lens Design Processor 320, in response to the receiving 622; wherein (d) coupling matrices CM(i) of the Visual Feedback-Search Management Neural Network 520-SGE were trained by performing a deep learning cycle 624.

Here, and in what follows, the Visual Feedback-Search Management Neural Network 520-SGE will be referenced with the same numerical labels as the Visual Feedback-Design Factor Neural Network 520, only with the sub-label "SGE" appended to it. This is to avoid needless repetition, as the embodiments are largely analogous.

In some embodiments, the method 620 can also include the followings.

(e) modifying the progressive lens design 123 by the Progressive Lens Design Processor 320 prompted by the Search Management step 450/490; and (f) generating a modified Comprehensive PLS 30 by the Progressive Lens Simulator 100, using the modified progressive lens design 123.

Repeating steps (b)-(f) iteratively can serve as the backbone of the exploration of the progressive lens designs, as described in relation to method 400.

The Visual Feedback-Search Management Neural Network 520-SGE of the AI-SGE 530 can include layers of neurons $N_{ij}$, including an input layer 515-SGE, one or more hidden layers 521/522/523-SGE, and an output layer 525-SGE; the neurons $N_{ij}$, having switching functions $f(x)$, and the neurons $N_{ij}$ being coupled by the coupling matrices CM(i).

In some embodiments, the performing the deep learning cycle 624 can include performing the deep learning cycle by Backpropagation with Gradient Descent BGD 510T-SGE.

In some embodiments, the performing a deep learning cycle 624 can include using 625 a Lens Merit function LM 460.

In some embodiments, the performing a deep learning cycle 624 can include evaluating 626 the outputted Search Management step 450/455 or 490/495 with an output evaluator 526 in relation to a target Search Management step corresponding to the inputted Visual Feedback vector VF 430; and training the coupling matrices CM(i) according to the evaluating with a coupling trainer 528.

By way of an example, the Search Management step can be 490(a), the reversing the search path. The decision that at which Visual Feedback VF 430 to reverse the path can be very much a complex decision. For example, referring back to FIG. 29A, it needs to be determined how much does the height of the ridge of the Lens Merit function LM 460 has to drop from its previous maximum for the AI-SGE 530 to activate the Search Management step 490(a). The AI-SGE 530 can be driven through many deep learning cycles to find and learn the optimal value to reverse the search path.

Referring to FIGS. 28A-B is another example: when a search starts to show less and less progress, the AI-SGE 530 needs to decide when to execute a non-local jump, and whether the jump should be entirely random or be driven by some consideration, e.g., the stored memory of an earlier portion of the search remembering the value of the Lens Merit function LM 460. As before, the AI-SGE 530 can be driven through many deep learning cycles to find and learn when to initiate a jump, how big a jump to initiate, and how to relate the jump of data stored from the earlier search path.

In some embodiments, the performing a deep learning cycle 624 can include modifying 627 a software of the Search Guidance Engine 330.

In some embodiments, the AI-GPS 500 system may include a deep learning unit that uses an eye-model, such as the Holladay or Hofer eye model, wherein the AI-GPS 500 can train the parameters of the GPS 10 based of the eye model.

Finally, very analogous methods can be practiced to train and then operate the AI Engine for the Progressive Lens Simulator (AI-PLS) 550. This AI-PLS 550 can include a Visual Feedback-Lens Simulation Neural Network 520-PLS, with components and elements very analogous shown in FIGS. 31-33, and operated analogously to FIGS. 34-35.

As mentioned earlier, the Artificial Intelligence Engine 500 can use any of the known AI methods, and is not narrowed down to neural networks alone. Other AI methods include Supervised learning methods, Non-supervised learning, Regression analysis-based methods, Clustering, Dimensionality reduction, Structured predictions, Anomaly detection and Reinforcement training. Any one of these AI methods can be implemented in the AI-GPS 500.

8. Central Supervision Station System for Progressive Lens Simulators

One of the substantial benefits of the various embodiments of the GPS system 10, for example, the PLS 100, or the PLS 100 combined with the LDES 300, or the PLS 100 and the LDES 300 combined with the Artificial Intelligence Engine for GPS, AI-GPS 500, together referenced as the 100/300/500 embodiments of GPS 10, is that many of the functions previously executed by an optometrist are now carried out by the automated systems of the GPS 10. Therefore, an optometrist does not have to be continuously involved in the exploration of progressive lens designs 123. The patient himself/herself can engage with the 100/300/500 embodiments of the GPS 10 to execute any version of the exploration method 400, and take all the time he/she needs. The patient can go back to previously identified lens designs 123 and compare them with new ones; can chose different images 21 with the Image generator 121; keep performing Search Management steps 450/455 or 490/495 to retrace search paths, explore other choices, fix a Design Factor 420 to narrow the search, slow down the search in some region of the Design Factor space, and so on. All of these can be performed without active involvement by an optometrist.

From a time-management point of view, this aspect of the GPS 10 systems frees up an optometrist to such a degree that she/he can supervise more than one individual GPS systems 10 simultaneously, thereby eliminating the need of manning each optometry station individually with an optometrist. This aspect can substantially reduce the number of personnel required to service a given number of patients, and thus can be greatly helpful for the business model of the overall optometrist office.

Figure 36:
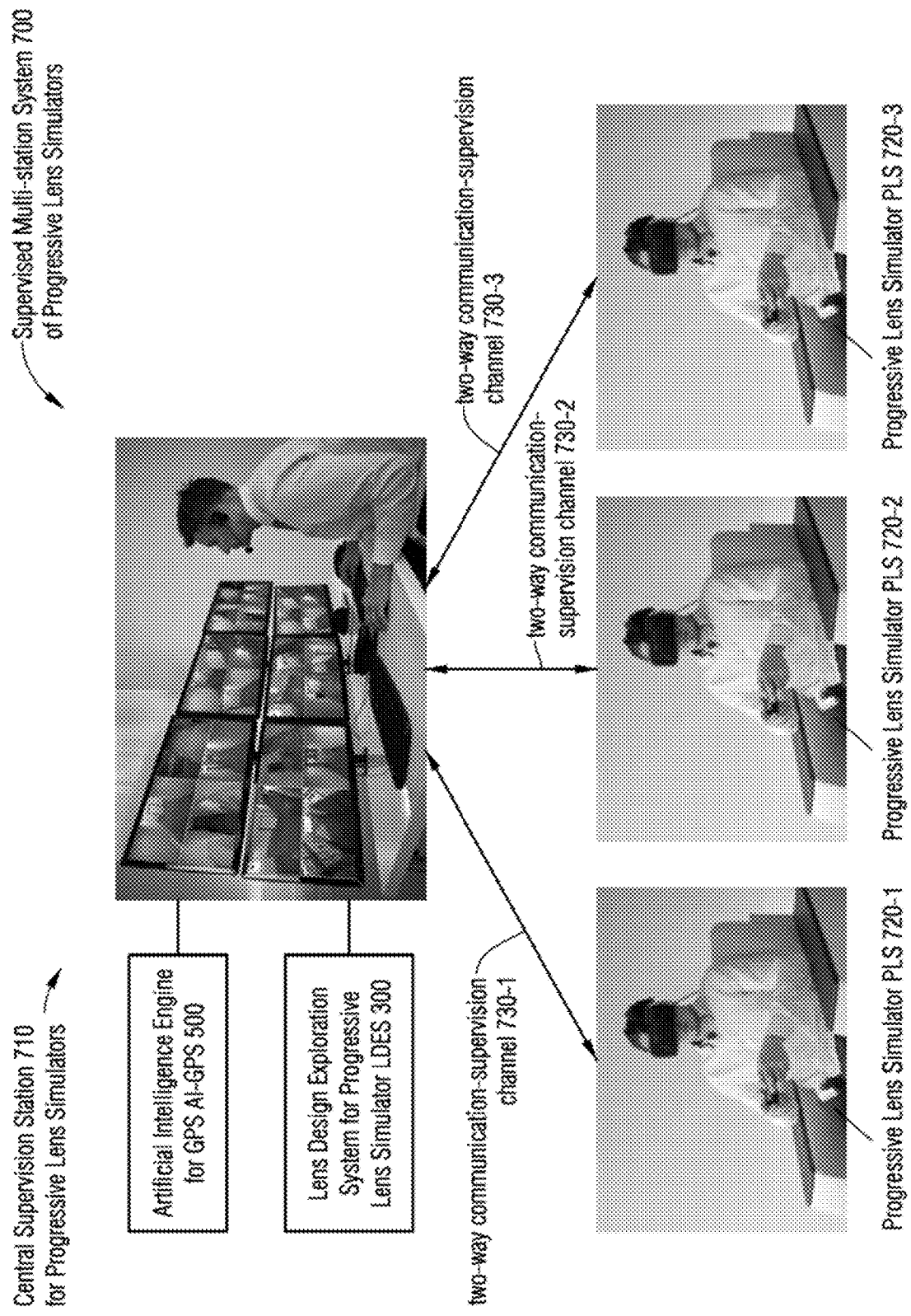
FIG. 36 illustrates a Supervised Multi-station System of Progressive Lens Simulators.

FIG. 36 illustrates this concept in some detail. FIG. 36 illustrates a Supervised Multi-station system 700 of Progressive Lens Simulators 100 that comprises a Central Supervision Station 710; coupled to a set of Progressive Lens Simulators 720-1, 720-2, . . . 720-n, (together referenced as 720-i) by two-way communication-supervision channels 730-1, 730-2, . . . 730-n, together referenced as 730-i. FIG. 36 illustrates a three station (n=3) embodiment.

The individual stations can include the Progressive Lens Simulators 720-i that can be any embodiment described earlier in this application, including the multistage PLS 100, the integrated IPLS 200, a table-top embodiment of a PLS 100, and the head-mounted PLS 260, this latter embodiment being shown in FIG. 36. In the shown embodiment, the PLS 720-i can individually include an Eye Tracker 110, for tracking an eye axis direction to determine a gaze distance; an Off-Axis Progressive Lens Simulator 120, for generating an Off-Axis progressive lens simulation (Off-Axis PLS 20) of a progressive lens design 123; and an Axial Power-Distance Simulator ADS 130, for simulating a progressive lens power in the eye axis direction, thereby creating a Comprehensive Progressive Lens Simulation (PLS) 30 of a progressive lens design 123 from the Off-Axis PLS 20.

Some elements of the PLS 720-i can be implemented in the Central Supervision station 710. The Central Supervision Station 710 can be in communication with the Progressive Lens Simulators 720-i, for providing supervision for an operation of the individual Progressive Lens Simulators 720-i.

This communication can take place via the two-way communication channels 730-i between the individual Progressive Lens Simulators 720-i and the Central Supervision Station 710: the Progressive Lens Simulators 720-i can inform the Central Supervision Station 710 about simulations of progressive lens designs 123; and the Central Supervision Station 710 supervising the simulation by the Progressive Lens Simulators 720-i. The communication channels 730-i can be wired communication channels or wireless communication channels.

In some embodiments, the Progressive Lens Simulators 720-i can individually comprise Lens Design Exploration Systems LDES 300, for guiding an exploration of progressive lens designs 123.

In other embodiments, the Central Supervision Station 710 can comprise a centralized Lens Design Exploration System LDES 300, for guiding an exploration of progressive lens designs, and communicating corresponding guidance signals to the individual Progressive Lens Simulators 720-i.

In some embodiments, the individual Progressive Lens Simulators 720-i can include dedicated individual Artificial Intelligence (AI) Engines for executing a deep learning method for Progressive Lens Design Processors 320-i of the Progressive Lens Simulators 720-i. These AI Engines can be embodiments of the AI Engines for the Progressive Lens Design Processors (AI-PLD) 510.

In other embodiments, the Central Supervision Station 710 can comprise a centralized Artificial Intelligence Engine 500, for executing a deep learning method for the Progressive Lens Design Processors 320 of the Progressive Lens Simulators 720-i, and communicating corresponding training signals to the individual Progressive Lens Simulators 720-i.

In some embodiments, the Progressive Lens Simulators 720-i can individually comprise Artificial Intelligence Engines, for executing a deep learning method for Search Guidance Engines 330 of the Progressive Lens Simulators 720-i. These AI Engines can be embodiments of the AI Engines for the Search Guidance Engines (AI-SGE) 520.

In other embodiments, the Central Supervision Station 720-i can comprise a centralized Artificial Intelligence Engine 500, for executing a deep learning method for a centralized Search Guidance Engine, and communicating corresponding guiding signals to the individual Progressive Lens Simulators 720-i. The Search Guidance Engine can be also centralized, or can reside in the individual PLS 720-i as individual SGEs 330-i.

Similarly, an AI Engine can be included for executing a deep learning method for the Off-Axis PLS 120. As before, this AI Engine can be centralized, or can reside with the individual PLS 720-i.

While this document contains many specifics, these should not be construed as limitations on the scope of an invention or of what may be claimed, but rather as descriptions of features specific to particular embodiments of the invention. Certain features that are described in this document in the context of separate embodiments can also be implemented in combination in a single embodiment. For example, to structure the presentation more clearly, the description of the embodiments was organized into eight sections. However, the features of the embodiments in any one of these sections can be combined with features and limitations of any embodiments from the other seven sections. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or a variation of a subcombination.

The invention claimed is:

1. A Progressive Lens Simulator, comprising:
an Eye Tracker, for tracking an eye axis direction to determine a gaze distance;

an Off-Axis Progressive Lens Simulator, for generating an Off-Axis Progressive Lens Simulation (Off-Axis PLS) according to a progressive lens design, including
an Image Generator, for generating an image;
an Off-Axis Progressive Lens Simulator Processor, for transforming the generated image into an Off-Axis PLS signal according to the progressive lens design by
receiving the generated image from the Image Generator; and
transforming the generated image into the Off-Axis PLS signal by introducing a locally varying curvature, representative of the progressive lens design; and
an Off-Axis Progressive Lens Simulator Display for displaying the Off-Axis PLS according to the Off-Axis PLS signal; and
an Axial Power-Distance Simulator, for simulating a progressive lens power of the progressive lens design in the eye axis direction, thereby creating a Comprehensive Progressive Lens Simulation (Comprehensive PLS) from the Off-Axis PLS.

2. The Progressive Lens Simulator of claim 1, the Off-Axis Progressive Lens Simulator Display comprising:
a pair of Off-Axis Progressive Lens Simulator Screens, each displaying an Off-Axis PLS, for providing a stereoscopic Off-Axis PLS for a first eye and for a second eye.

3. The Progressive Lens Simulator of claim 1, the Off-Axis Progressive Lens Simulator Display comprising:
a stereoscopic alternating Off-Axis Progressive Lens Simulator Screen, controlled by an image-alternator, for alternating the displaying the Off-Axis PLS for the first eye, and subsequently for the second eye, with suitable stereoscopic adjustments.

4. The Progressive Lens Simulator of claim 1, wherein:
the Off-Axis Progressive Lens Simulator Processor is configured
to receive the generated image from the Image Generator; and
to transform the generated image into the Off-Axis PLS signal by introducing a locally varying blur, representative of the progressive lens design.

5. The Progressive Lens Simulator of claim 1, wherein:
at least two of the Image Generator, the Off-Axis Progressive Lens Simulator Processor, and the Off-Axis Progressive Lens Simulator Display are integrated.

6. The Progressive Lens Simulator of claim 1, comprising:
a Vergence-Distance Simulator, for, simulating a vergence for the displayed Off-Axis PLS at the gaze distance.

7. The Progressive Lens Simulator of claim 6, wherein:
the Vergence-Distance Simulator is configured to simulate a vergence for the displayed Off-Axis PLS at the distance by at least one of
moving a screen of the Off-Axis Progressive Lens Simulator Display dominantly laterally, and
shifting the displayed Off-Axis PLS on the Off-Axis Progressive Lens Simulator Display dominantly laterally.

8. The Progressive Lens Simulator of claim 1, comprising:
a Zoom-Distance Simulator, for zooming the comprehensive PLS to represent a change in the gaze distance.

9. The Progressive Lens Simulator of claim 1, wherein:
at least one of the Off-Axis Progressive Lens Simulator Processor, the Off-Axis Progressive Lens Simulator Display, and the Axial Power-Distance Simulator include at least one of a Vergence-Distance Simulator and a Zoom-Distance Simulator.

10. The Progressive Lens Simulator of claim 1, the Axial Power-Distance Simulator comprising:
an adjustable optical power system, having an adjustable optical refractive power.

11. The Progressive Lens Simulator of claim 10, wherein:
the optical refractive power of the Axial Power-Distance Simulator is adjustable to be consistent with one of the determined gaze distance and an intended gaze distance.

12. The Progressive Lens Simulator of claim 10, wherein:
the Axial Power-Distance Simulator is adjustable to simulate a vergence corresponding to the eye axis direction.

13. The Progressive Lens Simulator of claim 10, the adjustable optical power system comprising:
an Alvarez lens system, including
at least two lenses for an eye, at least one of the two lenses having laterally varying curvature; and
one or more actuators, for sliding at least one of the lenses laterally relative to the other lens, thereby changing an optical refractive power of the Alvarez lens system in a central region.

14. The Progressive Lens Simulator of claim 10, the adjustable optical power system comprising:
an adjustable fluid lens system, including
a pair of adjustable fluid lenses, with optical refractive power that is controlled by an amount of fluid in the fluid lenses;
a fluid-management system, for adjusting the amount of fluid in the fluid lenses; and
lens-adjusting electronics, for controlling the pair of adjustable fluid lenses and the fluid-management system to adjust the optical refractive power of the adjustable optical power system.

15. The Progressive Lens Simulator of claim 10, wherein:
the adjustable optical power system is selected from the group consisting of
a shape-changing lens, an index-of-refraction-changing lens, a variable mirror, a deformable optic, an aspheric lens with adjustable aperture, a liquid crystal optical element, an adjustable reflective optical element, an adjustable opto-electronic element, and an optical system with an optical component with adjustable relative position.

16. A Progressive Lens Simulator, comprising:
an Eye Tracker, for tracking an eye axis direction to determine a gaze distance;
an Off-Axis Progressive Lens Simulator, for generating an Off-Axis Progressive Lens Simulation (Off-Axis PLS) according to a progressive lens design, including
an Image Generator, for generating an image;
an Off-Axis Progressive Lens Simulator Processor, for transforming the generated image into an Off-Axis PLS signal according to the progressive lens design; and
an Off-Axis Progressive Lens Simulator Display, for displaying the Off-Axis PLS according to the Off-Axis PLS signal, including
a pair of Off-Axis Progressive Lens Simulator Screens, each displaying an Off-Axis PLS, for providing a stereoscopic Off-Axis PLS for a first eye and for a second eye; and
an Axial Power-Distance Simulator, for simulating a progressive lens power of the progressive lens design in the eye axis direction, thereby creating a Comprehensive Progressive Lens Simulation (Comprehensive PLS) from the Off-Axis PLS.

17. A Progressive Lens Simulator, comprising:
an Eye Tracker, for tracking an eye axis direction to determine a gaze distance;
an Off-Axis Progressive Lens Simulator, for generating an Off-Axis Progressive Lens Simulation (Off-Axis PLS) according to a progressive lens design, including
   an Image Generator, for generating an image;
   an Off-Axis Progressive Lens Simulator Processor, for transforming the generated image into an Off-Axis PLS signal according to the progressive lens design; and
   an Off-Axis Progressive Lens Simulator Display, for displaying the Off-Axis PLS according to the Off-Axis PLS signal; and
an Axial Power-Distance Simulator, for simulating a progressive lens power of the progressive lens design in the eye axis direction, thereby creating a Comprehensive Progressive Lens Simulation (Comprehensive PLS) from the Off-Axis PLS; and
a Vergence-Distance Simulator, for simulating a vergence for the displayed Off-Axis PLS at the gaze distance.

* * * * *